US008153787B2

(12) United States Patent
Holy et al.

(10) Patent No.: US 8,153,787 B2
(45) Date of Patent: Apr. 10, 2012

(54) AZACYTOSINE DERIVATIVES USEFUL AS ANTIVIRAL AGENTS

(75) Inventors: Antonin Holy, Prague (CZ); Marcela Krecmerova, Prague (CZ); Alois Piskala, Prague (CZ); Graciela Andrei, Sint-Lambrechts-Woluwe (BE); Robert Snoeck, Sint-Lambrechts-Woluwe (BE); Erik De Clercq, Bierbeek (BE); Johan Neyts, Kessel-Lo (BE); Lieve Naesens, Puurs (BE)

(73) Assignees: K.U. Leuven Research & Development, Leuven (BE); Institute of Organic Chemistry and Biochemistry Academy of Sciences of the Czech Republic, Prague (CZ)

( * ) Notice: Subject to any disclaimer, the term of this patent is extended or adjusted under 35 U.S.C. 154(b) by 662 days.

(21) Appl. No.: 12/096,738
(22) PCT Filed: Dec. 8, 2006
(86) PCT No.: PCT/BE2006/000130
§ 371 (c)(1),
(2), (4) Date: Jun. 9, 2008

(87) PCT Pub. No.: WO2007/065231
PCT Pub. Date: Jun. 14, 2007

(65) Prior Publication Data
US 2009/0005346 A1    Jan. 1, 2009

(30) Foreign Application Priority Data

Dec. 8, 2005 (GB) .................................. 0525033.7
Dec. 9, 2005 (GB) .................................. 0526668.9
Jun. 9, 2006 (GB) .................................. 0611440.9

(51) Int. Cl.
*C07F 9/38* (2006.01)
*C07F 9/40* (2006.01)
*C07F 9/42* (2006.01)
*A61K 31/675* (2006.01)
*A61P 31/20* (2006.01)
*A61P 31/22* (2006.01)
*C07D 251/46* (2006.01)
*C07D 251/52* (2006.01)

(52) U.S. Cl. .................. 544/195; 536/26.11; 536/26.12; 536/28.3; 514/245; 544/214; 544/220

(58) Field of Classification Search .................. 544/195, 544/214, 220; 514/241, 245; 536/28.3, 26.11, 536/26.12
See application file for complete search history.

(56) References Cited

U.S. PATENT DOCUMENTS 4,347,360 A    8/1982   Ogilvie
2004/0138170 A1  7/2004   Montgomery et al.

FOREIGN PATENT DOCUMENTS

EP    0 243 670    11/1987

OTHER PUBLICATIONS

West, Anthony R., Solid State Chemistry and its Applications, Wiley, New York, 1988, pp. 358 & 365.*
Vippagunta et al., Advanced Drug Delivery Reviews 48: 3-26, 2001.*
Cecil Textbook of Medicine, edited by Bennet, J.C., and Plum F., 20th edition,vol. 1, 1004-1010, 1996.*
Freshney et al.,Culture of Animal Cells, A Manual of Basic Technique, Alan R. Liss, Inc., 1983, New York, p4.*
Dermer et al., Bio/Technology, 1994, 12:320.*
Golub et al., Science, 286, 531-537, 1999.*
Daifuku Biodrugs17(3); 169-177, 2003.*
Griffiths, P.A. Journal of Virology, 46, 3-8, 2009.*
Hayden , F. G., Review in Medical Virology, 14, 17-31, 2004.*
Baker et al., "Potential Antiviral Therapeutics for Smallpox, Monkeypox and Other Orthopox Virus Infections," Antiviral Res. 57(1-2):13-23 (2003).
Holý et al., "Structure-Antiviral Activity Relationship in the Series of Pyrimidine and Purine N-[2-(2-Phosphonomethoxy)ethyl] Nucleotide Analogues. 1. Derivatives Substituted at the Carbon Atoms of the Base," J. Med. Chem. 42(12):2064-2086 (1999).
Krecmerová et al., "Antiviral Activity of Triazine Analogues of 1-(S)-[3-Hydroxy-2-(phosphonomethoxy)propyl]cytosine (Cidofovir) and Related Compounds." J. Med. Chem. 50(5):1069-1077 (2007).
International Search Report for International Application PCT/BE2006/000130, mailed May 23, 2007.
Written Opinion of the International Searching Authority for International Application PCT/BE2006/000130, mailed May 23, 2007.
Reply to Written Opinion of the International Searching Authority for International Application PCT/BE2006/000130, dated Oct. 8, 2007.
International Preliminary Report on Patentability for International Application PCT/BE2006/000130, dated May 13, 2008.
Office Action for European Application EP 06 828 083.3, dated Jul. 6, 2009.
Krečmerová et al., "Antiviral activity of triazine analogues of 1-(S)-[3-hydroxy-2-(phosphonomethoxy)propyl]cytosine (cidofovir) and related compounds," J. Med. Chem. 50:1069-1077, 2007.
Krečmerová et al., "Ester prodrugs of cyclic 1-(S)-[3-hydroxy-2-(phosphonomethoxy)propyl]-5-azacytosine: synthesis and antiviral activity," J. Med. Chem. 50:5765-5772, 2007.
Naesens et al., "Intracellular metabolism of the new antiviral compound 1-(S)-[3-hydroxy-2-(phosphonomethoxy)propyl]-5-azacytosine," Biochem. Pharmacol. 76:997-1005, 2008.
Duraffour et al., "Activities of several classes of acyclic nucleoside phosphonates against camelpox virus replication in different cell culture models," Antimicrob Agents Chemother. 51:4410-9, 2007.
Gammon et al., "Mechanism of antiviral drug resistance of vaccinia virus: identification of residues in the viral DNA polymerase conferring differential resistance to antipoxvirus drugs," J Virol. 82:12520-34, 2008.
Lebeau et al., "Inhibitory activities of three classes of acyclic nucleoside phosphonates against murine polyomavirus and primate simian virus 40 strains," Antimicrob Agents Chemother. 51:2268-73, 2007.
Topalis et al., "Activity of different classes of acyclic nucleoside phosphonates against BK virus in primary human renal cells," Antimicrob Agents Chemother. pp. 1-28, Epub Feb. 22, 2011.

* cited by examiner

Primary Examiner — Venkataraman Balasubramanian
(74) Attorney, Agent, or Firm — Clark & Elbing LLP

(57) ABSTRACT

The present invention provides 5-azacytosine derivatives with antiviral activity, specifically having viral replication inhibiting properties, more particularly in DNA viruses such as pox-, papilloma- and herpes viruses in humans. The invention also provides pharmaceutical compositions comprising such 5-azacytosine derivatives as active ingredients in combination with pharmaceutically acceptable carriers, which are useful for the treatment of subjects suffering from viral infections.

13 Claims, 13 Drawing Sheets

A

B

A

B

A

B

A

B

AZACYTOSINE DERIVATIVES USEFUL AS ANTIVIRAL AGENTS

FIELD OF THE INVENTION

The present invention relates to novel nucleoside phosphonate analogs. The invention further relates to compounds having viral replication inhibiting and virus-induced cell proliferation inhibiting activity. The invention also relates to methods for preparation of all such compounds and pharmaceutical compositions comprising them. The invention further relates to the use of said compounds as a medicine and for the manufacture of a medicament useful for the treatment of subjects suffering from a viral infection and to the treatment of mammals suffering from a viral infection. The invention also provides methods of treatment or prevention of a viral infection or a viral-induced cell proliferative disease in a mammal.

BACKGROUND OF THE INVENTION

Viral infections remain a major medical problem worldwide because of a lack of therapy, prevention or vaccination strategy and because of the rapid development of resistance. Viruses can be divided into two big groups, RNA-viruses and DNA-viruses, according to their genetic composition, which can then further be subdivided. Human pathogens include Adenovirus, Cytomegalovirus, Dengue virus, Ebola virus, Enterovirus, Epstein Barr Virus, Hantavirus, Hepatitis A virus, Hepatitis B virus, Hepatitis C virus, Herpes Simplex virus, Human Herpes Virus 6, 7 and 8, Human Immunodeficiency Virus, Human Metapneumovirus, Human Papilloma Virus, Influenza virus, Marburg virus, Nipah virus, Parvovirus B19, Polyoma BK virus, Polyoma JC virus, Respiratory Syncytial Virus, Varicella-Zoster virus, Variola, Coxsackie virus and others.

Human Papilloma Virus and other viruses are known to induce, or increase the predisposition to, cell proliferation disorders such as e.g. cancer tumours in human beings.

HIV-I (human immunodeficiency virus-1) is one of the problematic viral infections with an estimated 40 million people infected worldwide. However, many other viruses and virus families causing problematic disorders can be identified.

As an example, the family of the Herpesviridae includes important human pathogens like Herpes simplex virus (HSV) type 1 and 2, Varicella-Zoster virus (VZV), Cytomegalovirus (CMV), Epstein Barr virus (EBV) and human Herpes virus type 6, 7 and 8 (i.e. HHV-6, -7 and -8). These viruses cause disorders like Herpes Labialis, Herpes Genitalis, Herpes Encephalitis, Kaposi's sarcoma, Varicella, Zona, lymfomas and others. Current treatments consist of Acyclovir, Ganciclovir, Brivudin, Cidofovir and some other products.

Acyclic nucleoside phosphonates (ANPs), such as cidofovir (HPMPC) and adefovir (PMEA), were shown to inhibit the replication of HSV. Cidofovir (Vistide—Gilead Sciences) is used for the treatment of Cytomegalovirus (CMV) retinitis infection, which can cause blindness. However, it has been established that Cidofovir can be harmful to the kidneys. If someone is taking cidofovir, doctors need to watch for early signs of kidney problems using blood and urine tests. Decreased urination, increased thirst, or light-headedness after standing up can also be early warning signs of kidney problems. If a person already has kidney problems, cidofovir may not be an appropriate treatment for them. Furthermore, Cidofovir is given by intravenous infusion, directly into a vein in the arm. The infusion is given once a week for the first two weeks—this is called the induction treatment. The infusion is then given once every other week to keep the CMV infection under control. Long-term maintenance therapy is necessary. To try and prevent kidney damage, cidofovir is given with fluids. Probenecid, a drug that helps protect the kidneys, must also be given with cidofovir. Unfortunately, probenecid contains a sulfonyl group and can cause allergic reactions. Side effects caused by reactions to sulfonyl group-containing drugs can include rash and fever.

Also the Poxviruses comprise human and animal pathogens. The most important human pathogen in this family, the Variola virus (smallpox) has been the first human virus to be definitely eradicated, after mass vaccination under the control of the WHO. The last (natural) case of variola was described in October 1977 and the vaccination was definitely ceased in 1978. Meanwhile several strains of both variola major and variola minor were kept in reference centers in United States and Russia (formerly USSR), where they had to be destroyed after a decision of the World Health Assembly (WHO). However, in the last years, researchers were stimulated to develop new therapies as well as novel approaches for the prophylaxis or treatment of poxvirus infections due to the increased concern on the possible release of such viruses as mass destruction weapons by bioterrorists. Based on the possible release of infectious agents from repositories, variola among many other viruses and bacteria, is considered as one of the possible threats in a world population with a majority of people non immunized and lack of immunity that had not been boosted for several decades. Therefore, it was decided to intensify the development of better diagnostic tools, to generate new classes of vaccines responding to the actual rules of safety, and finally, to search for new and potent antiviral drugs. In order to reach these objectives, the destruction of variola stocks was postponed to allow the characterization of the different strains and to establish and validate different surrogate models using other (ortho)poxviruses for diagnostics, vaccines and antiviral drugs. In the mean time, other poxviruses for which no particular treatment is currently available have been recognized as of importance for human health, such as Monkeypox or Orf. Similarly, some poxviruses specific for animals, such as Camelpox, Cowpox or Orf could be of economical importance for some regions of the world.

As a conclusion, for many pathogenic viral infections, no efficient treatment is currently available and, moreover, the available anti-viral therapies or preventive measures are not sufficient in order to be able to cure, prevent or ameliorate the respective viral infections due to many reasons, like the occurrence of resistance and unfavorable pharmacokinetics or safety profiles.

Therefore, there is a clear need to enlarge the arsenal of antiviral molecules, especially against herpes viruses and poxviruses, and more especially against human herpesvirus 6, by developing new classes of compounds with better activity, a better resistance profile, a different and original mechanism of action, or improved pharmacokinetics or safety profiles to allow an optimal prevention or therapy of virus infections, as an example, in case of an extended spread of one or another poxvirus.

The present invention provides novel compounds that satisfy this need. More specifically, the current invention provides novel compounds which inhibit viral replication and which possess a higher activity, more specifically also against resistant viruses as compared to the compound HPMPC (Cidofovir) or which are less toxic such as for the kidney.

SUMMARY OF THE INVENTION

In the present invention, novel compounds are provided. It is an advantage of the present invention to provide compounds with a better activity against viruses, more in particular against viruses showing resistance against currently used drugs such as HPMPC. It is also an advantage of the invention to provide chain terminating antiviral nucleoside analogs. It is also an advantage to provide compounds with a better activity against human herpes virus 6 compared to HPMPC. It is furthermore an advantage of the present invention to provide antiviral compounds with a lower toxicity on human renal cells than HPMPC. Compounds of the invention are novel azacytosine derivatives. It has been shown that they possess antiviral activity, more specifically against DNA viruses. They are also active against virus-induced cell proliferative disorders. The present invention demonstrates that the compounds inhibit the replication of DNA viruses such as pox- and herpesviruses and that the compound is more active against HPMPC resistant virus strains than HPMPC. Compounds of the invention furthermore are chain terminators. Therefore, these compounds constitute a new potent class of antiviral agents that can be used in the treatment and prevention of viral infections in animals, mammals and humans, more specifically for the treatment and prevention of viral infections.

The present invention relates to novel azacytosine derivatives. The invention further relates to compounds having antiviral activity, more specifically to novel 5-azacytosine derivatives having viral replication inhibiting properties, more in particular of DNA viruses such as pox- and herpesviruses in humans, and consequently may be useful for the treatment of individuals infected by such viruses. Present invention furthermore relates to the use of the compounds as a medicine and more specifically to the use of the compounds as an antiviral agent. The invention also relates to methods for preparation of all such compounds and pharmaceutical compositions comprising them. The invention further relates to the use of said compounds in the manufacture of a medicament useful for the treatment of subjects suffering from a viral infection, as well as for treatment of tumours or cancers. The present invention also relates to a method of treatment or prevention of viral infections, by using said compounds.

One aspect of the present invention is the provision of 5-azacytosine derivatives, said new 5-azacytosine derivatives being a phosphonate, more in particular comprising 3-hydroxy-2-phosphonomethoxypropyl coupled to the $N^1$-position of 5-azacytosine.

The present invention relates to 5-azacytosine derivatives and 6-azacytosine derivatives according to the structural formula (I) or formula (III), a stereochemically isomeric form, a solvate, a salt, a 5,6-dihydro derivative or a prodrug thereof:

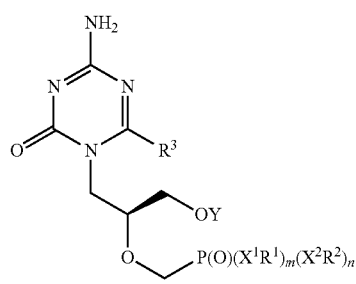

(I)

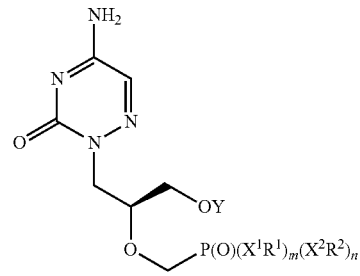

(III)

wherein
$R^1$ and $R^2$ are independently selected from the group consisting of hydrogen, $C_{1-30}$ alkyl, $C_{2-30}$ alkenyl, $C_{2-30}$ alkynyl, aryl, $C_{1-30}$ alkylphenyl and aryl-$C_{1-30}$ alkyl wherein each of said $C_{1-30}$ alkyl, $C_{2-30}$ alkenyl or $C_{2-30}$ alkynyl optionally contains one or more heteroatoms selected from the group consisting of oxygen, nitrogen and sulphur in the main chain and/or is optionally substituted with one or more substituents selected from the group consisting of hydroxy, oxo and halogen or $R^1$ and $R^2$ are linked by one or more bonds to form a five, six or seven members ring comprising P, $X^1$ and $X^2$, said ring being optionally fused with a phenyl ring;

$X^1$ is selected from the group consisting of $NR^4$ and oxygen;

$X^2$ is selected from the group consisting of $NR^5$ and oxygen;

$R^4$ and $R^5$ are independently selected from the group consisting of hydrogen, $C_{1-30}$ alkyl, $C_{2-30}$ alkenyl and $C_{2-30}$ alkynyl, wherein each of said $C_{1-30}$ alkyl, $C_{2-30}$ alkenyl or $C_{2-30}$ alkynyl optionally contains one or more heteroatoms selected from the group consisting of oxygen, nitrogen and sulphur in the main chain and/or is optionally substituted with one or more substituents selected from the group consisting of hydroxy and halogen;

Y is hydrogen or is a bond linking oxygen to phosphorous to form a six-membered cyclic phosphonic acid ester;

each of m and n is 1 when Y is hydrogen, or one of m and n is 1 and the other one of m and n is 0 when Y is a bond linking oxygen to phosphorous to form a 6-membered cyclic phosphonic acid ester;

$R^3$ is a hydrogen, a $C_{1-4}$ alkyl, aryl, aryl-$C_{1-4}$alkyl, amino, hydroxy, $CO_2H$, $CO_2R$, $CONH_2$, $NR_2$, $CONR_2$; and R is $C_{1-30}$ alkyl.

A particular embodiment of this aspect of the invention relates to (S)-1-[3-hydroxy-2-phosphonomethoxypropyl]-5-azacytosine of formula (II), and the salts, esters, amidates and esteramidates thereof:

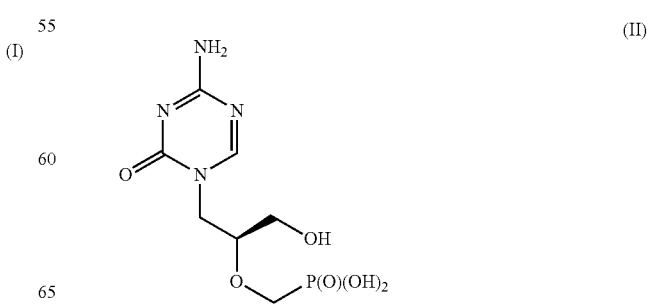

(II)

The present invention relates in a particular embodiment to individual compounds selected from the group consisting of:

(S)-1-[3-hydroxy-2-phosphonomethoxypropyl)-5-azacytosine;

3-formyl-2-{[(2S)-3-hydroxy-2-(phosphonomethoxy)propyl]carbamoyl}guanidine; and

1-{[(5S)-2-Hydroxy-2-oxido-1,4,2-dioxaphosphinan-5-yl]methyl}-5-azacytosine (hereinafter referred as "cyclic HPMP-5-azacytosine");

and esters thereof as described herein.

The present invention relates in another particular embodiment to 5,6-dihydro derivatives of 5-azacytosine derivatives according to the formulae (I) or (II).

According to a second aspect, the invention relates to the use of 5-azacytosine derivatives of the formulas (I) or (II) as antiviral compounds, more particularly as compounds active against DNA viruses and as compounds active against cancer. The invention also relates to the use of 5-azacytosine derivatives of the formula (I) or (II), more in particular of (S)-1-[3-hydroxy-2-phosphonomethoxypropyl)-5-azacytosine for the manufacture of a medicine or as a pharmaceutically active ingredient, especially as a virus replication inhibitor, preferably a DNA-virus replication inhibitor, for instance for the manufacture of a medicament or pharmaceutical composition having anticancer or antiviral activity for the prevention and/or treatment of cancer or viral, preferably DNA-viral infections in humans or mammals.

In a particular embodiment, said DNA-viral infection is selected from an infection with a virus from the Herpesviridae such as Herpes simplex virus, Varicella-Zoster virus (VZV), Cytomegalovirus (CMV), from the Poxviridae such as Vaccinia virus, Variola virus (smallpox), Cowpox, Monkeypox, Camelpox or Orf and from the family of the Papillomaviridae such as Human papilloma virus.

Another aspect of the present invention relates to a method of treatment of cancer or a viral infection, preferably an infection with a DNA-virus in a mammal, including a human, comprising administering to the mammal in need of such treatment a therapeutically effective amount of a compound of formula (I) or (II) as an active ingredient, preferably in admixture with at least a pharmaceutically acceptable carrier. The invention provides for a method of treatment or prevention of a viral infection in a mammal, comprising administering to the mammal in need of such treatment a therapeutically effective amount of a 5-azacytosine derivatives of the invention.

Yet another aspect of the present invention relates to methods or processes for the preparation of compounds of formula (I) or (II), in a particular embodiment of (S)-1-[3-hydroxy-2-phosphonomethoxypropyl)-5-azacytosine. Said method or process comprises the steps of (i) heating (S)-trityloxymethyloxirane with 5-azacytosine in the presence of alkali, preferentially sodium or potassium hydroxide or cesium carbonate, (ii) treatment of thus obtained intermediate with dialkyl-, preferentially diisopropyl bromomethylphosphonate and 1-1.5 molar equivalents of alkali, preferentially sodium or potassium tert butoxide, or sodium hydride at temperatures 10-60° C. in aprotic solvent, preferentially dimethylformamide, dimethylsulfoxide or tetrahydrofurane and (iii) reacting thus obtained protected intermediate with halotrimethylsilane, preferentially bromotrimethylsilane in acetonitrile, dimethylformamide, tetrahydrofurane, dioxane or chlorinated aprotic solvents followed by hydrolysis in water.

In another embodiment, the process for the preparation of compounds of formula (I) or (II), in a particular embodiment of (S)-1-[3-hydroxy-2-phosphonomethoxypropyl)-5-azacytosine comprises the steps of (i) heating the sodium salt of 5-azacytosine with 3-hydroxy-2-(dialkoxyphosphonylmethoxy)propyl, preferentially 3-hydroxy-diisopropyloxymethoxy)propyl p-tolylsulfonate and (ii) reacting thus obtained protected intermediate with halotrimethylsilane, preferentially bromotrimethylsilane in acetonitrile, dimethylformamide, tetrahydrofurane, dioxane or chlorinated aprotic solvents followed by hydrolysis in water.

A further aspect of the invention relates to pharmaceutical compositions comprising the compounds of the invention according to formula (I) or (II) in admixture with at least a pharmaceutically acceptable carrier, the active ingredient preferably being in a concentration range of about 0.1 to 100% by weight, and to the use of these derivatives namely as drugs useful for the treatment of subjects, more in particular humans, suffering from cancer or a viral infection.

The invention further relates to the use of a composition comprising (a) one or more derivatives of formula (I) or (II), and (b) one or more viral inhibitors as biologically active agents in respective proportions, for instance in the form of a combined preparation for simultaneous, separate or sequential use in viral infection therapy. Within the framework of this embodiment of the invention, the viral replication inhibitors used as a therapeutically active ingredients (b) may belong to categories already known in the art and include, among others, Acyclovir and its prodrug valacyclovir (e.g. active against alpha-herpesviruses HSV and VZV), Ganciclovir and its prodrug valganciclovir (e.g. active against beta-herpesviruses HHV-6 and HCMV and alpha herpesviruses HSV and VZV), Foscavir (e.g. active against alpha- and beta-herpesviruses), Brivudin (e.g. active against HSV-1 and VZV), Cidofovir (e.g. active against all DNA viruses except hepatitis B), Adefovir (e.g. active against all herpesviruses and hepatitis B) and Lamivudine (e.g. active against hepatitis B).

More generally, the invention relates to the compounds of formula (I) or (II) or embodiments thereof being useful as agents having biological activity (preferably antiviral or antitumoral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal or being non-animal cells.

Figure 1:
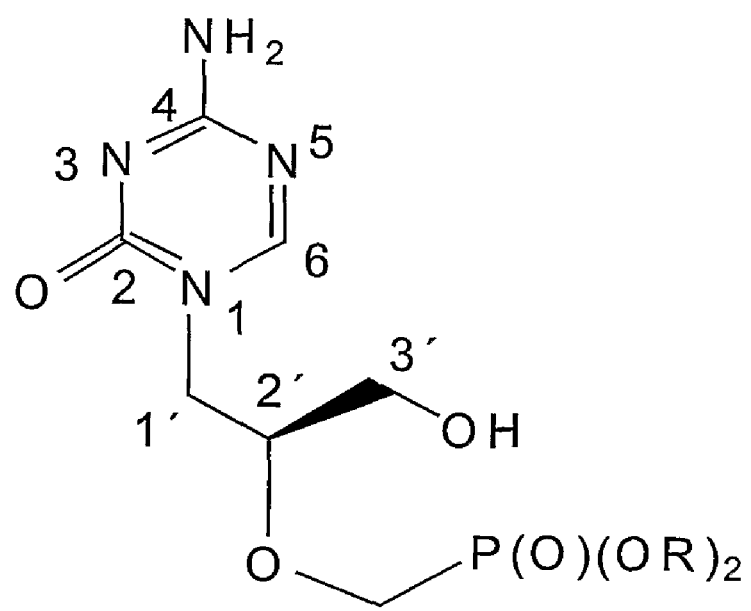
FIG. 1 shows the structure of (S)-1-[3-hydroxy-2-(phosphonomethoxy)propyl]-5-azacytosine together with the numbering scheme for assignment of NMR signals.
Figure 2:
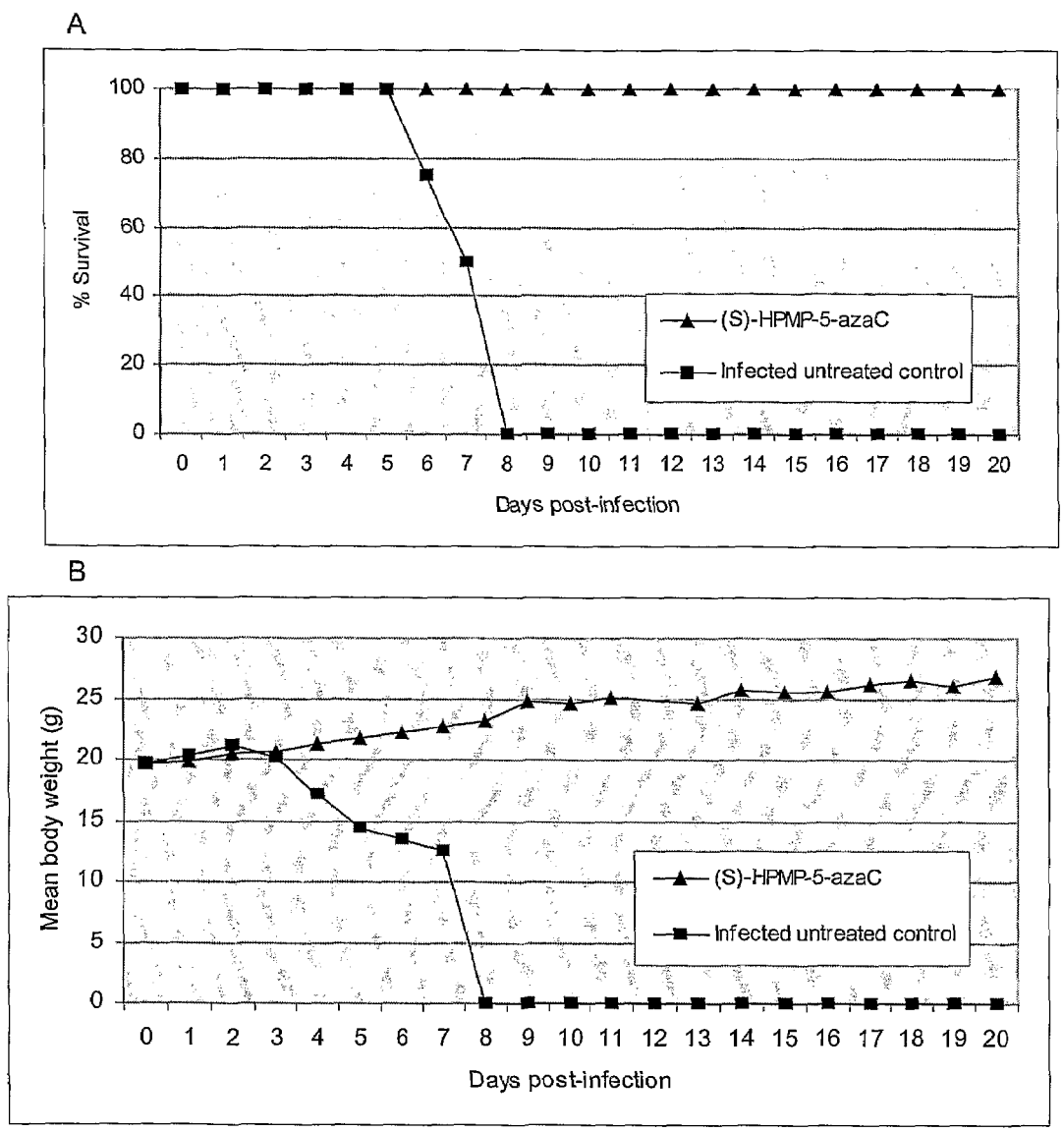
FIGS. 2 A and B show the results of an in vivo experiment for treatment of vaccinia virus infection with (S)-1-[3-hydroxy-2-(phosphonomethoxy)propyl]-5-azacytosine. Adult NMRI mice (18-20 grams) were infected with $4.0 \times 10^3$ PFU of vaccinia virus (Western Reserve strain) intranasally in a volume of 20 μL. Treatment with the compounds (dissolved in phosphate buffer saline, PBS) was started the day of infection. Compounds were administered subcutaneously once a day for a total of 5 days, at a dose of 50 mg/kg per day. Body weight (FIG. 2 B) and mortality (FIG. 2A) were registered for a period of 20 days. Four animals per experimental group were used.
Figure 3:
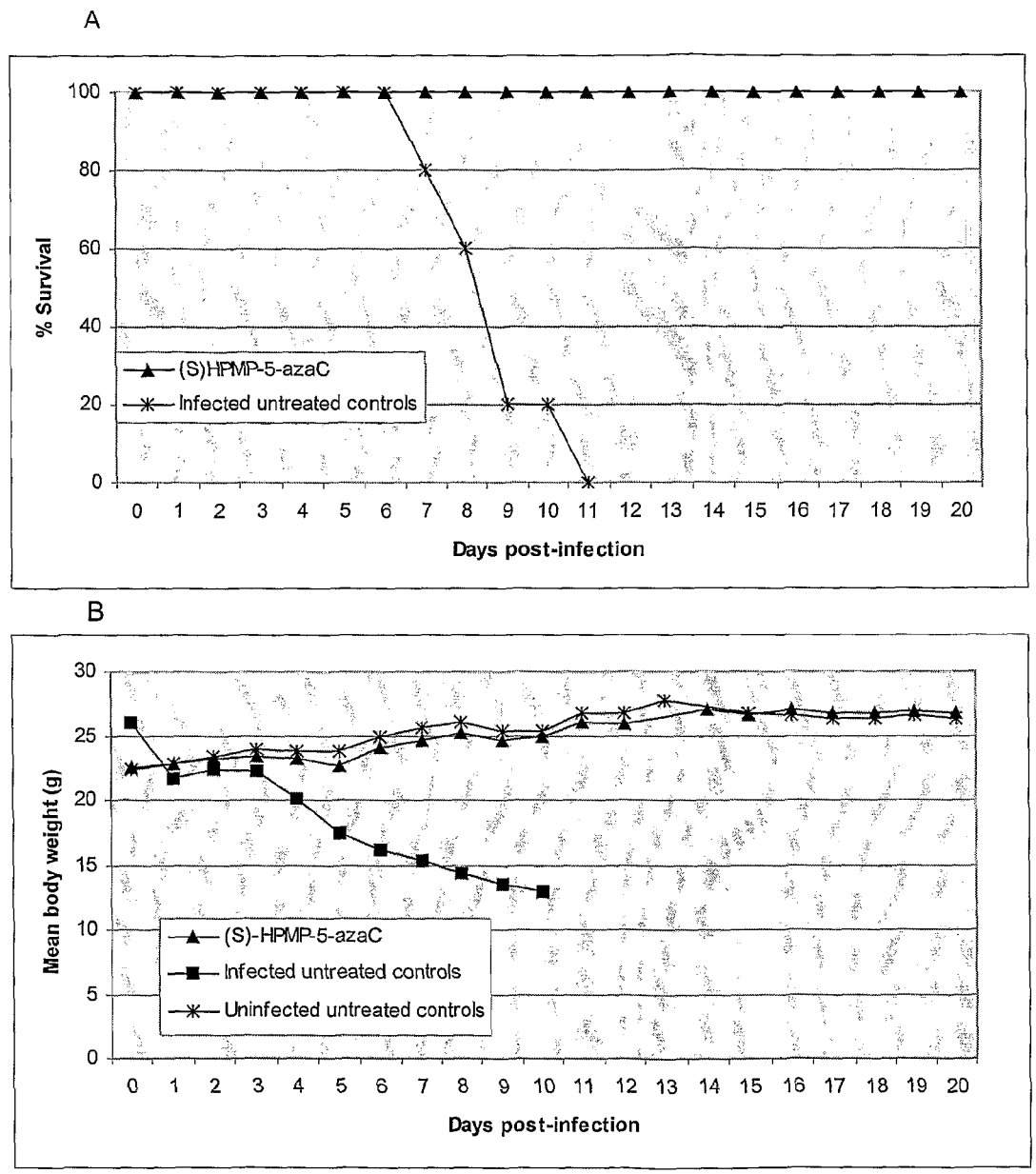
FIGS. 3 A and B show the results of an in vivo experiment for treatment of cowpox virus infection with (S)-1-[3-hydroxy-2-(phosphonomethoxy)propyl]-5-azacytosine. Adult NMRI mice (18-20 grams) were infected with $4.0 \times 10^3$ PFU of cowpox virus (Brighton strain) intranasally in a volume of 20 μL. Treatment with the compounds (dissolved in phosphate buffer saline, PBS) was started the day of infection.

Compounds were administered subcutaneously once a day for a total of 5 days, at a dose of 50 mg/kg per day. Body weight (FIG. 3 B) and mortality (FIG. 3 A) were registered for a period of 20 days. Five animals per experimental group were used.

Figure 4:
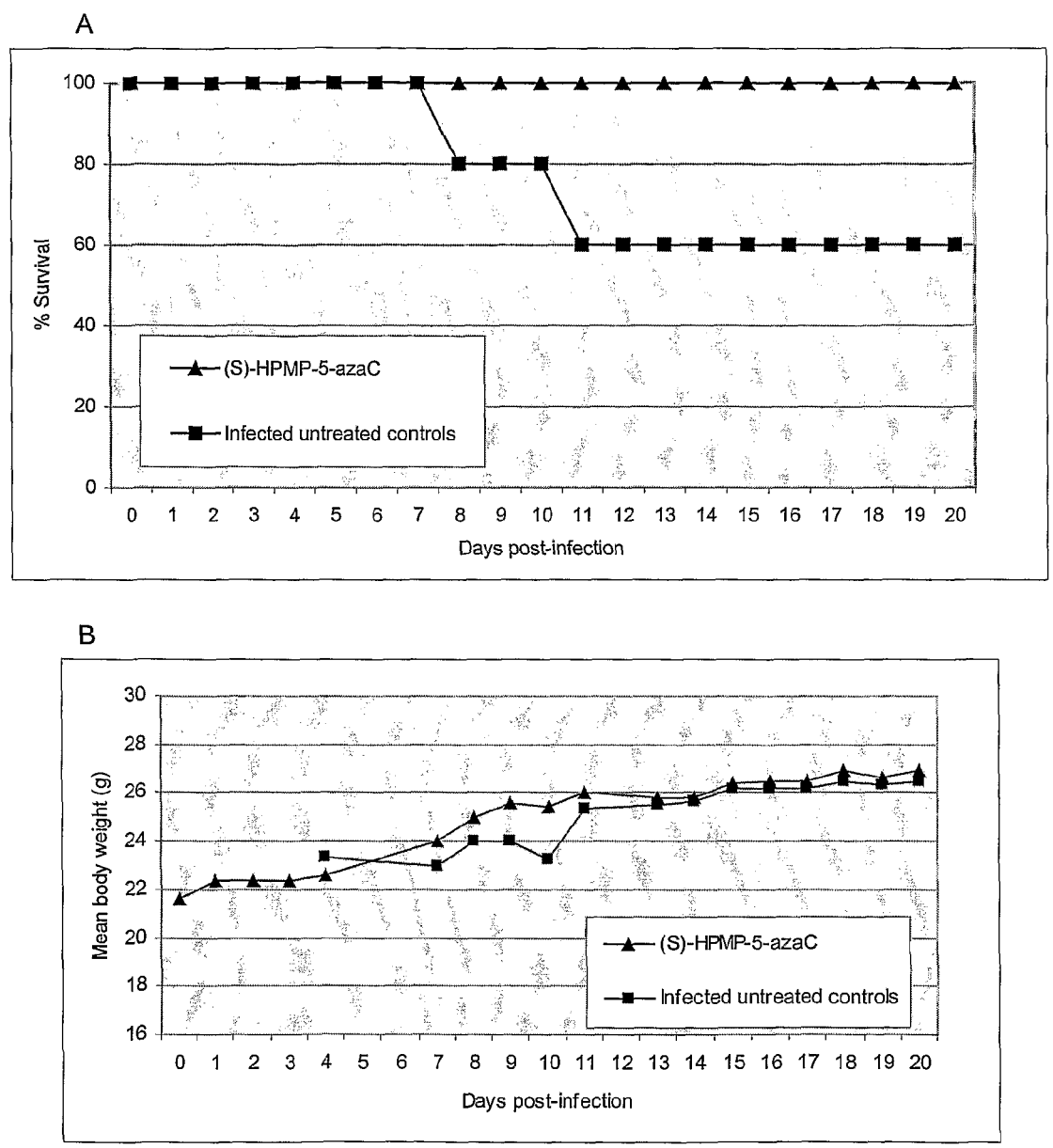

FIGS. 4 A and B show the results of an in vivo experiment for treatment of herpes simplex virus type 1 infection with (S)-1-[3-hydroxy-2-(phosphonomethoxy)propyl]-5-azacytosine. Adult NMRI mice (18-20 grams) were infected with approximately $1 \times 10^3$ PFU of HSV-1 (Kos strain) intraperitoneally in a volume of 200 µL. Treatment with the compounds (dissolved in phosphate buffer saline, PBS) was started the day of infection. Compounds were administered subcutaneously once a day for a total of 5 days, at a dose of 50 mg/kg per day. Body weight (FIG. 4 B) and mortality (FIG. 4 A) were registered for a period of 20 days. Five animals per experimental group were used.

Figure 5:
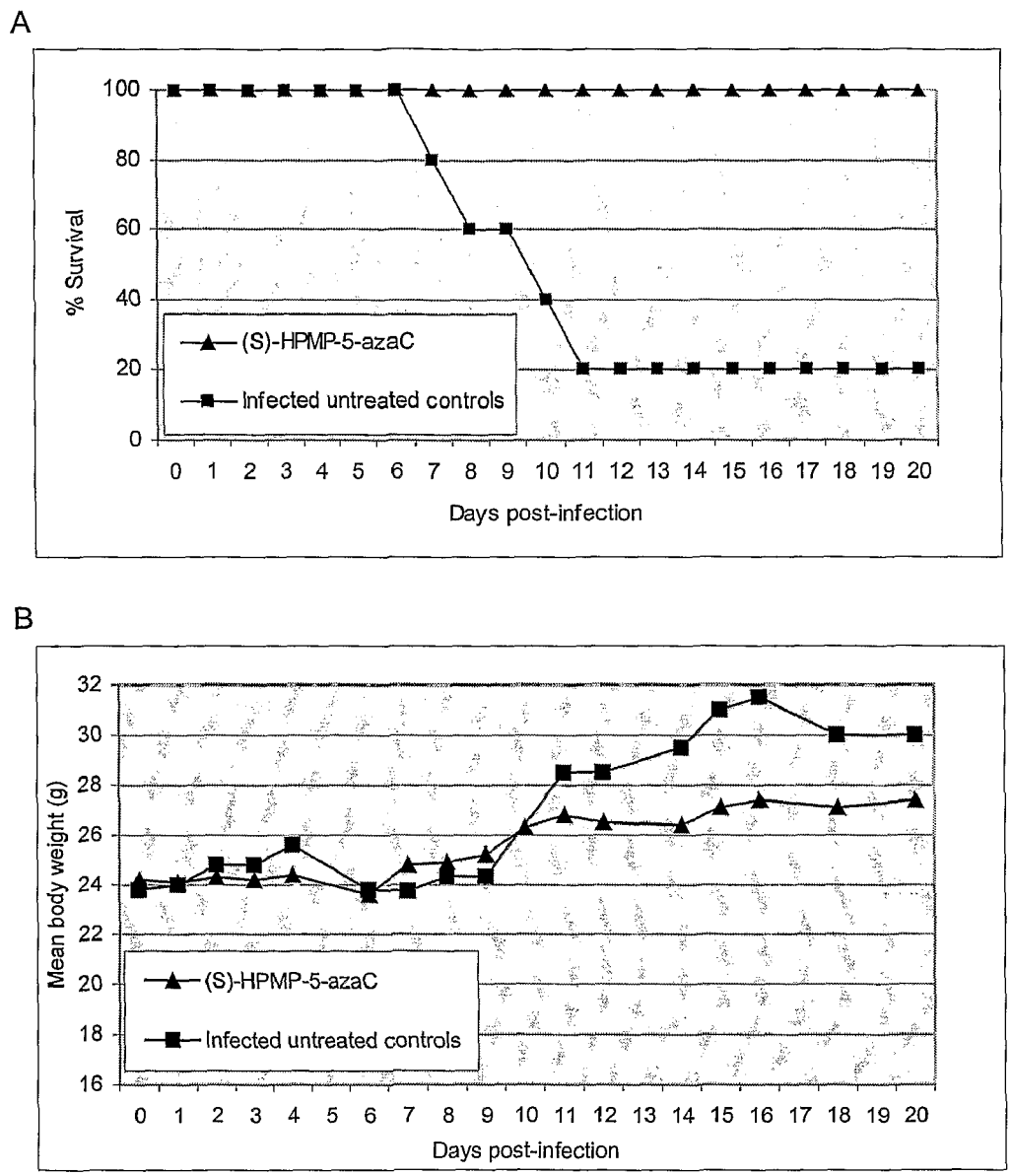

FIGS. 5 A and B show the results of an in vivo experiment for treatment of herpes simplex virus type 1 infection with (S)-1-[3-hydroxy-2-(phosphonomethoxy)propyl]-5-azacytosine. Adult NMRI mice (18-20 grams) were infected with approximately $2.5 \times 10^3$ PFU of HSV-1 (Kos strain) intraperitoneally in a volume of 200 µL. Treatment with the compounds (dissolved in phosphate buffer saline, PBS) was started the day of infection. Compounds were administered subcutaneously once a day for a total of 5 days, at a dose of 50 mg/kg per day. Body weight (FIG. 5 B) and mortality (FIG. 5 A) were registered for a period of 20 days. Five animals per experimental group were used.

Figure 6:
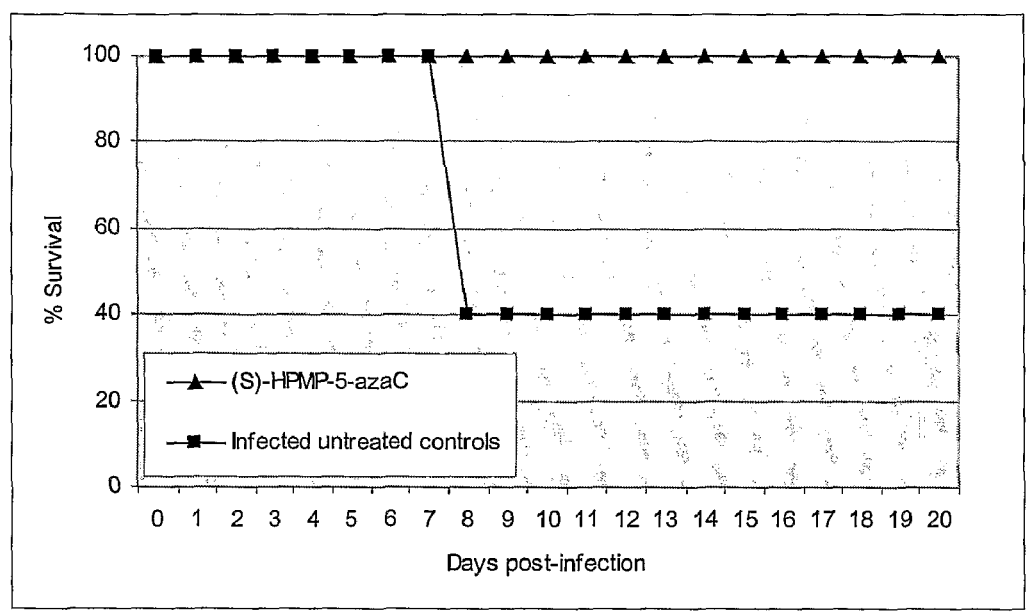

FIG. 6 shows the results of an in vivo experiment for treatment of herpes simplex virus type 2 infection with (S)-1-[3-hydroxy-2-(phosphonomethoxy)propyl]-5-azacytosine. Adult NMRI mice (18-20 grams) were infected with approximately $1 \times 10^3$ PFU of HSV-2 (Lyons strain) intraperitoneally in a volume of 200 µL. Treatment with the compounds (dissolved in phosphate buffer saline, PBS) was started the day of infection. Compounds were administered subcutaneously once a day for a total of 5 days, at a dose of 50 mg/kg per day. Body weight and mortality were registered for a period of 20 days. Five animals per experimental group were used.

Figure 7:
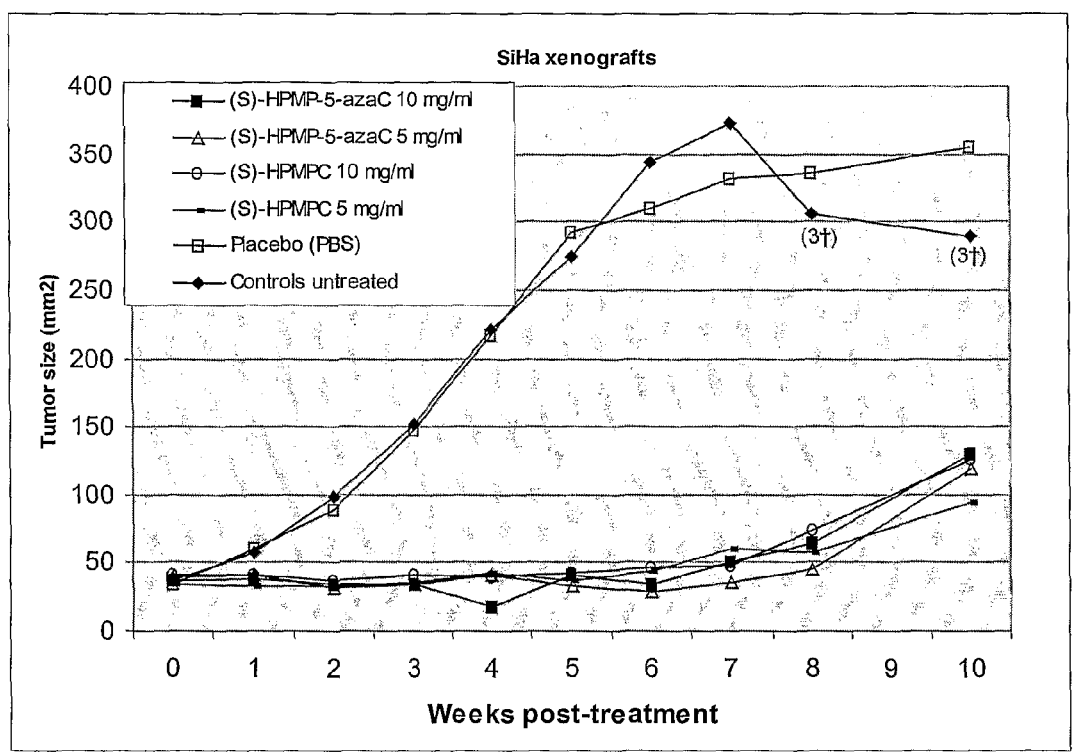

FIG. 7 shows the activity of (S)-1-[3-hydroxy-2-(phosphonomethoxy)propyl]-5-azacytosine compared to (S)-HPMPC against human papillomavirus in human cervical carcinoma (SiHa) xenografts in athymic nude mice. Adult animals were injected subcutaneously with $5 \times 10^6$ SiHa cells, a human cervical carcinoma cell line which harbors integrated human papillomavirus (HPV-16). Once the tumors were established (approximately after 1 week), the mice were divided in several groups, the tumor size for each mouse was determined, and treatment with placebo (PBS) or the test compounds was started. The test solutions were administered intratumorally at a volume of 50 µl. Mice were treated once a day, 5 times a week for a period of 5 weeks. Every week, the tumor size for each animal was measured with a caliper in two perpendicular dimensions and tumor size was calculated by multiplying the two measured diameters.

Figure 8:
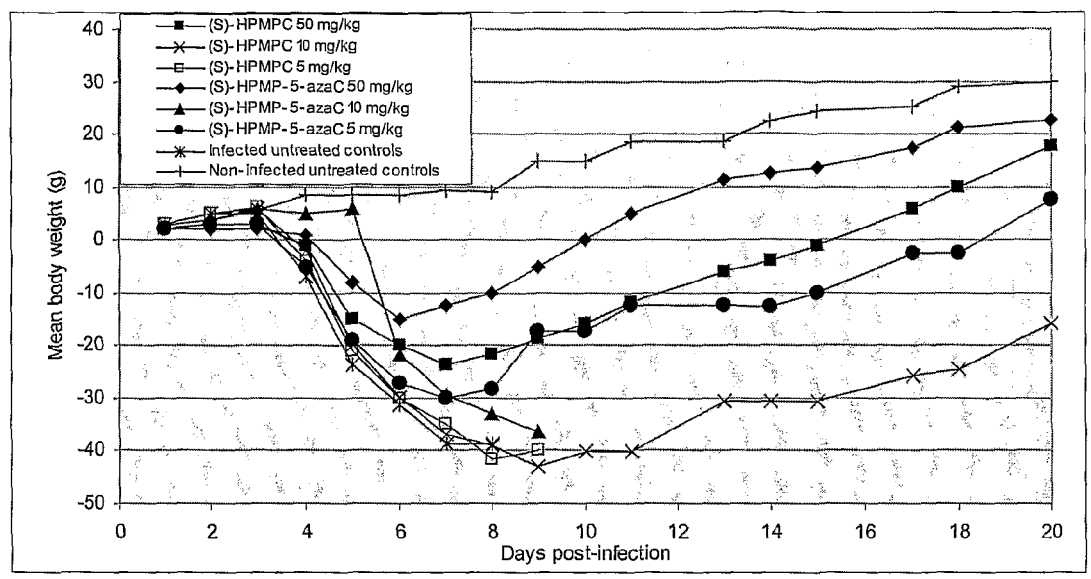
Figure 8:
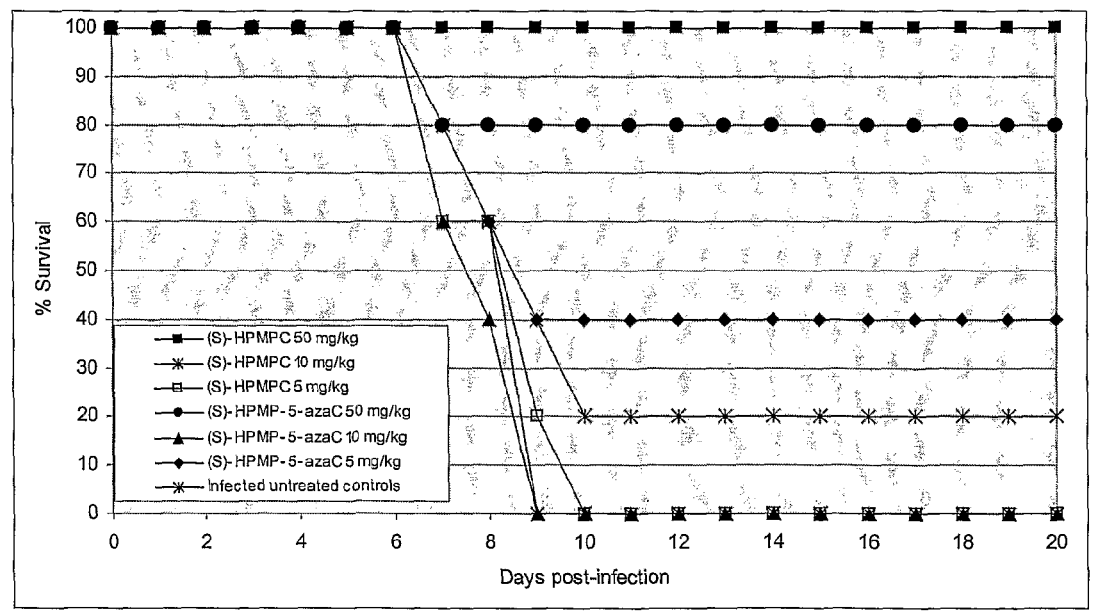

FIGS. 8 A and B show the activity of (S)-HPMP-5-azacytosine compared to (S)-HPMPC against poxviruses in a lethal intranasal model of infection in mice. Adult NMRI mice (18-20 grams) were infected with $4.0 \times 10^3$ PFU of vaccinia virus (Western Reserve strain) intranasally in a volume of 20 µL. Treatment with the compounds (dissolved in phosphate buffer saline, PBS) was started the day of infection. Compounds were administered orally once a day for a total of 5 days at the indicated doses. Body weight (FIG. 8 A) and mortality (FIG. 8 B) were registered for a period of 20 days. Five animals per experimental group were used.

Figure 9:
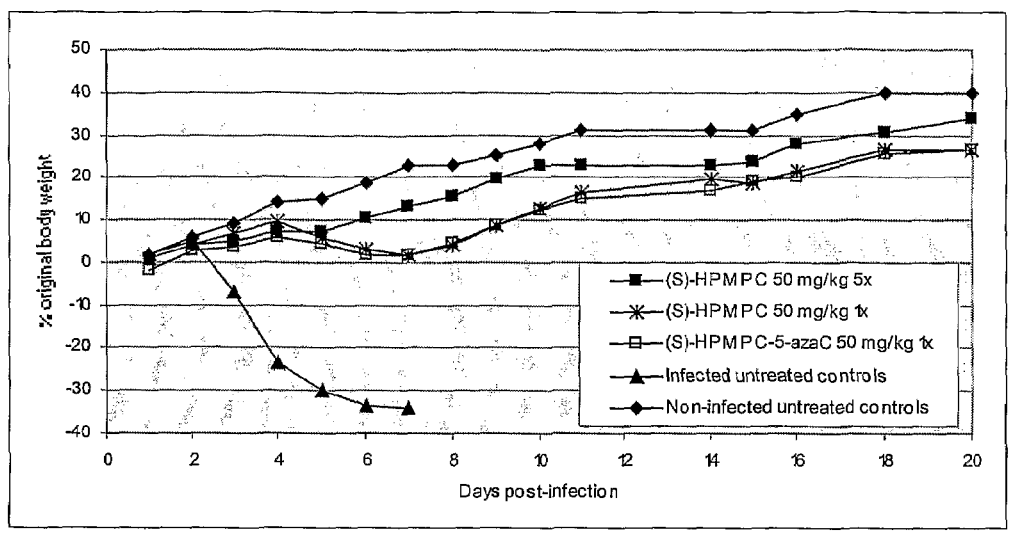
Figure 9:
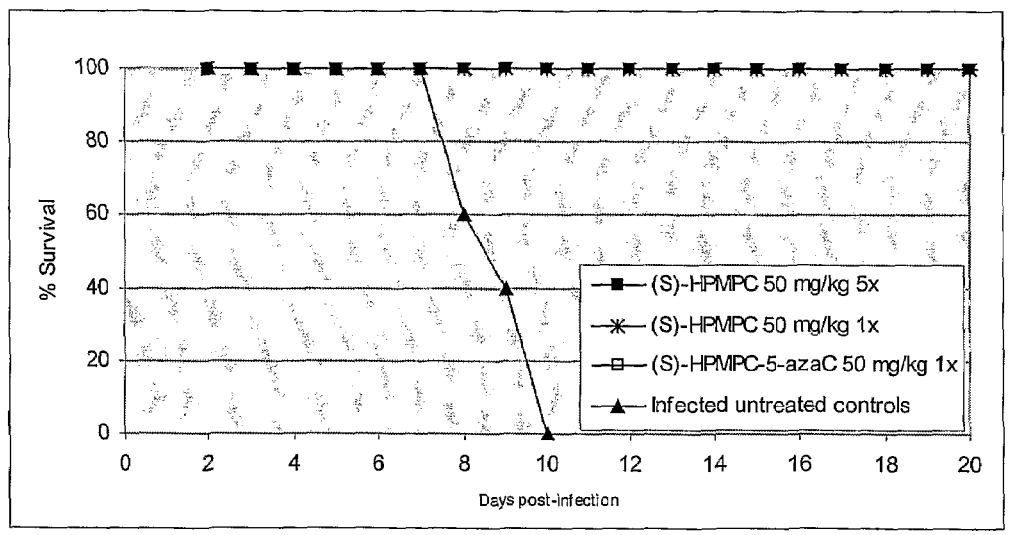

FIGS. 9 A and B show the activity of (S)-HPMP-5-azacytosine compared to (S)-HPMPC against poxviruses in a lethal intranasal model of infection in mice. Adult NMRI mice (18-20 grams) were infected with $4.0 \times 10^3$ PFU of vaccinia virus (Western Reserve strain) intranasally in a volume of 20 µL. Treatment with the compounds (dissolved in phosphate buffer saline, PBS) was started the day of infection. Compounds were administered subcutaneously once a day for only one day (1×) or for a total of 5 days (5×), at a dose of 50 mg/kg per day. Body weight (FIG. 9 A) and mortality (FIG. 9 B) were registered for a period of 20 days. Five animals per experimental group were used.

Figure 10:
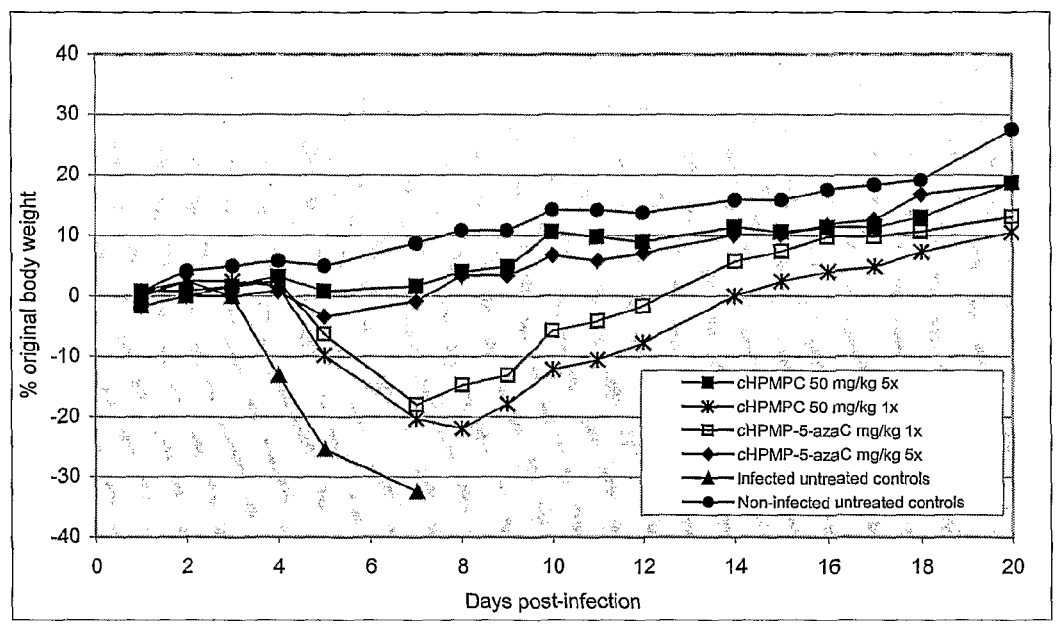
Figure 10:
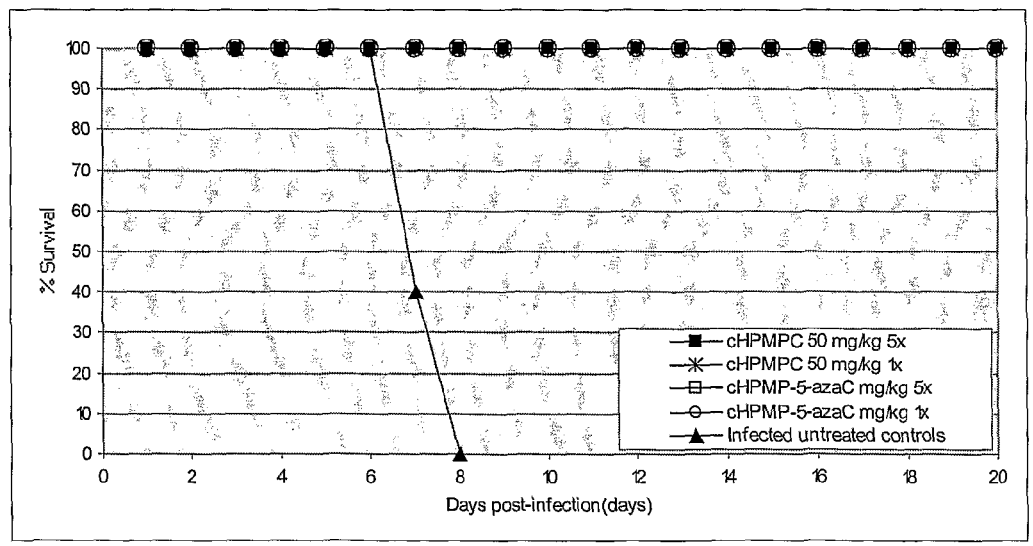

FIGS. 10 A and B show the activity of cHPMP-5-azacytosine compared to cHPMPC against poxviruses in a lethal intranasal model of infection in mice. Adult NMRI mice (18-20 grams) were infected with $4.0 \times 10^3$ PFU of vaccinia virus (Western Reserve strain) intranasally in a volume of 20 µL. Treatment with the compounds (dissolved in phosphate buffer saline, PBS) was started the day of infection. Compounds were administered subcutaneously once a day for only one day (1×) or for a total of 5 days (5×), at a dose of 50 mg/kg per day. Body weight (FIG. 10 A) and mortality (FIG. 10 B) were registered for a period of 20 days. Five animals per experimental group were used.

Figure 11:
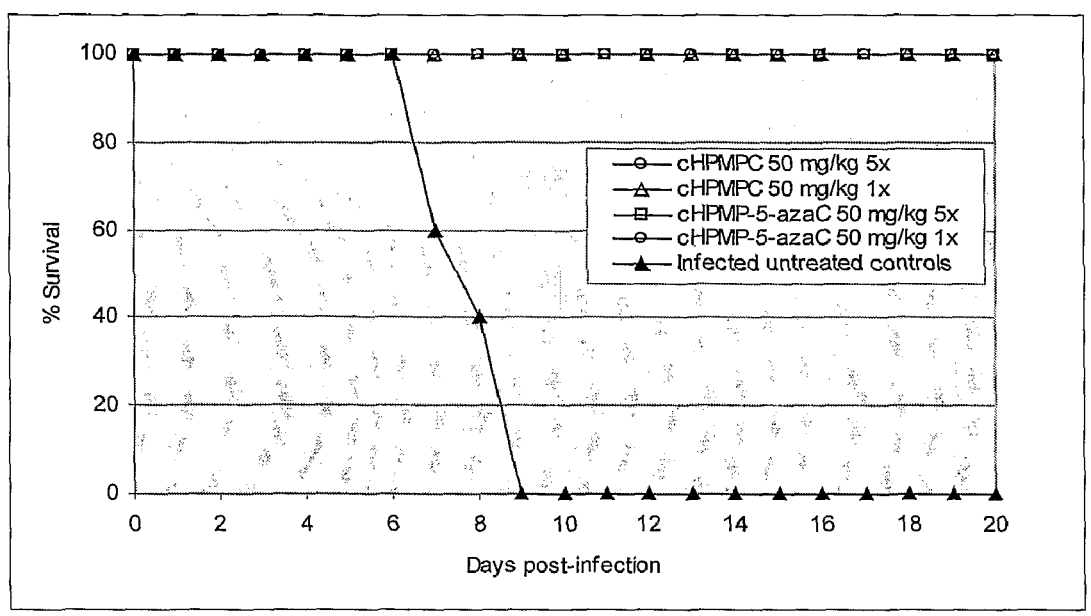

FIG. 11 shows the activity of cHPMP-5-azacytosine compared to cHPMPC against herpes simplex virus type 1 (HSV-1 in a lethal intraperitoneal model of infection in mice. Adult NMRI mice (18-20 grams) were infected with approximately $1 \times 10^3$ PFU of HSV-1 (Kos strain) intraperitoneally in a volume of 200 µL. Treatment with the compounds (dissolved in phosphate buffer saline, PBS) was started the day of infection. Compounds were administered subcutaneously once a day for a total of 5 days, at a dose of 50 mg/kg per day. Body weight and mortality were registered for a period of 20 days. Five animals per experimental group were used.

Figure 12:
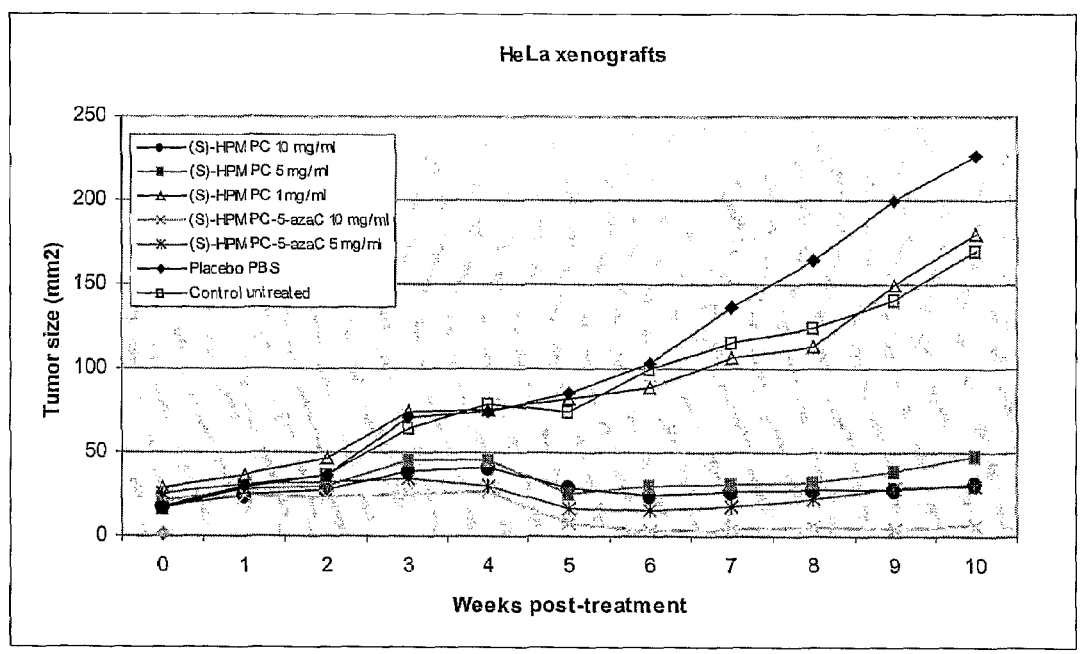
Figure 12:
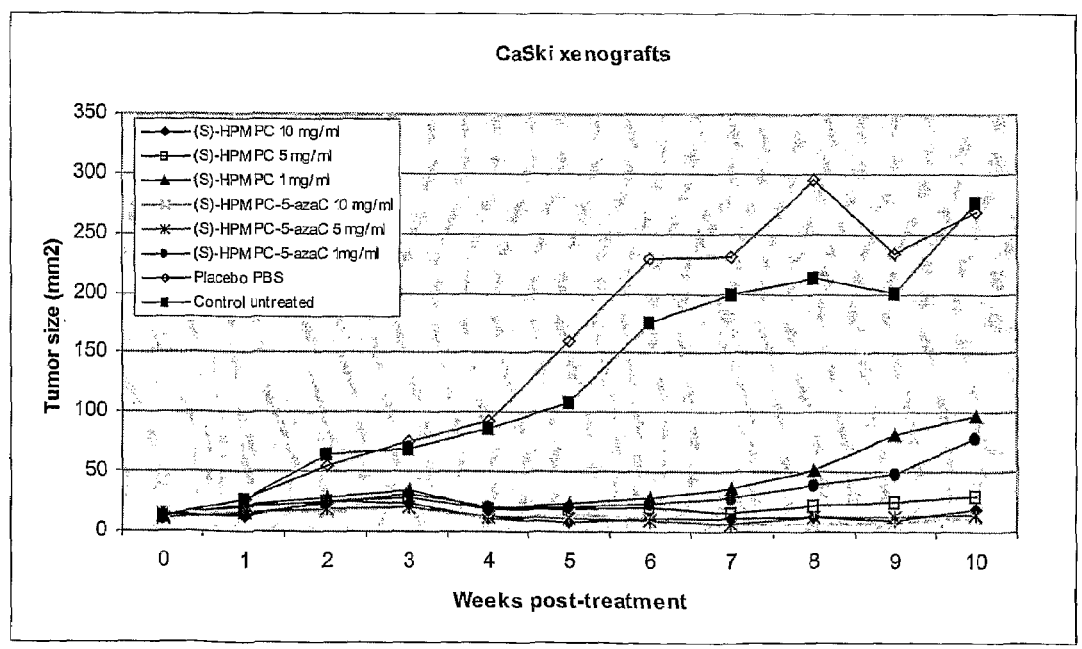

FIGS. 12 A and B show the activity of (S)-HPMP-5-azacytosine compared to (S)-HPMPC against human papillomavirus in human cervical carcinoma xenografts in athymic nude mice. (A) Adult animals were injected subcutaneously with $5 \times 10^6$ HeLa cells, a human cervical carcinoma cell line which harbors integrated human papillomavirus (HPV-16). Once the tumors were established (approximately after 1 week), the mice were divided in several groups, the tumor size for each mouse was determined, and treatment with placebo (PBS) or the test compounds was started. The test solutions were administered intratumorally at a volume of 50 µl. Mice were treated once a day, 5 times a week for a period of 5 weeks. Every week, the tumor size for each animal was measured with a caliper in two perpendicular dimensions and tumor size was calculated by multiplying the two measured diameters. (B) Adult animals were injected subcutaneously with $5 \times 10^6$ CaSki cells, a human cervical carcinoma cell line which harbors integrated human papillomavirus (HPV-16). Once the tumors were established (approximately after 1 week), the mice were divided in several groups, the tumor size for each mouse was determined, and treatment with placebo (PBS) or the test compounds was started. The test solutions were administered intratumorally at a volume of 50 µl. Mice were treated once a day, 5 times a week for a period of 5 weeks. Every week, the tumor size for each animal was measured with a caliper in two perpendicular dimensions and tumor size was calculated by multiplying the two measured diameters.

Figure 13:
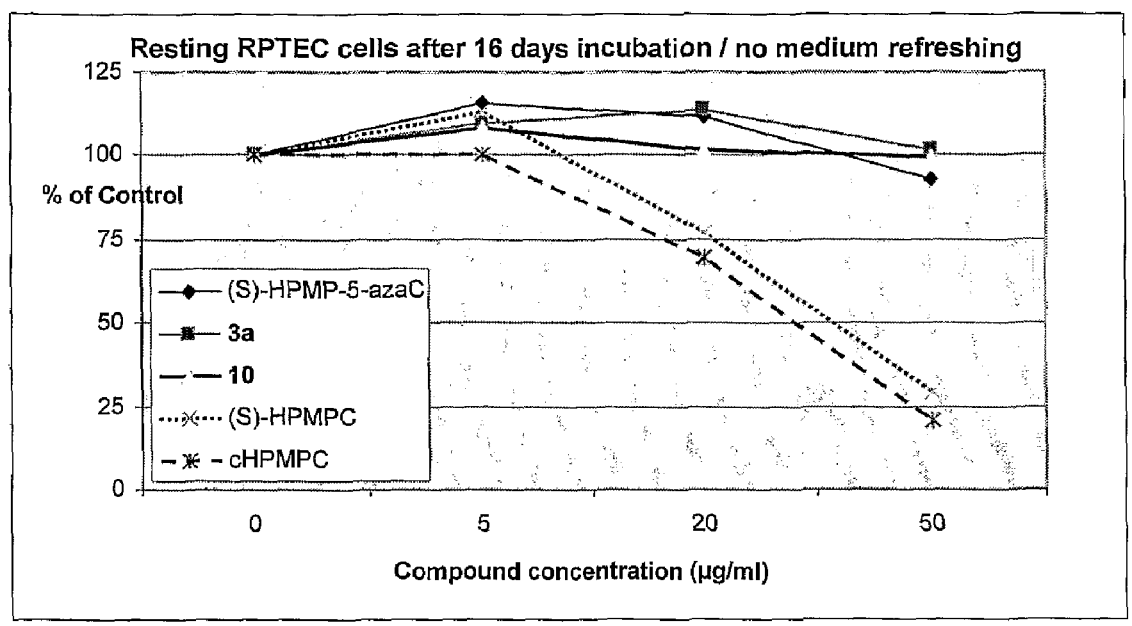

FIG. 13 shows the cytostatic activity of (S)-HPMP-5-azaC and cHPMP-5-azaC for primary cultures of human renal cells. Cytostatic activity for resting human renal proximal tubule epithelial cells (RPTEC) #4 after 16 days of incubation without medium refreshing.

DETAILED DESCRIPTION OF THE INVENTION

In each of the following definitions, the number of carbon atoms represents the maximum number of carbon atoms generally optimally present in the substituent or linker; it is understood that where otherwise indicated in the present application, the number of carbon atoms represents the optimal maximum number of carbon atoms for that particular substituent or linker.

The term "alkyl" as used herein refers to $C_1$-$C_{30}$ normal, secondary, or tertiary aliphatic saturated hydrocarbon chains. Examples are methyl, ethyl, 1-propyl, 2-propyl, 1-butyl, 2-methyl-1-propyl(i-Bu), 2-butyl (s-Bu) 2-methyl-2-propyl (t-Bu), 1-pentyl (n-pentyl), 2-pentyl, 3-pentyl, 2-methyl-2-butyl, 3-methyl-2-butyl, 3-methyl-1-butyl, 2-methyl-1-butyl, 1-hexyl, 2-hexyl, 3-hexyl, 2-methyl-2-pentyl, 3-methyl-2-pentyl, 4-methyl-2-pentyl, 3-methyl-3-pentyl, 2-methyl-3-pentyl, 2,3-dimethyl-2-butyl, 3,3-dimethyl-2-butyl, n-pentyl, n-hexyl, n-heptyl, n-octyl, n-nonyl, n-decyl, n-undecyl, n-dodecyl, n-tridecyl, n-tetradecyl, n-pentadecyl, n-hexadecyl, n-heptadecyl, n-octadecyl, n-nonadecyl and n-icosyl.

The term "alkenyl" as used herein is $C_2$-$C_{30}$ normal, secondary or tertiary ethylenically unsaturated hydrocarbon with at least one site (usually 1 to 3, preferably 1) of unsaturation, i.e. a carbon-carbon, sp2 double bond. Examples include, but are not limited to: ethylene or vinyl (—CH=$CH_2$), allyl (—$CH_2$CH=$CH_2$), cyclopentenyl (—$C_5H_7$), and 5-hexenyl (—$CH_2CH_2CH_2CH$=$CH_2$). The double bond may be in the cis or trans configuration.

The term "alkynyl" as used herein refer respectively $C_2$-$C_{30}$ normal, secondary, tertiary acetylenically unsaturated hydrocarbon with at least one site (usually 1 to 3, preferably 1) of unsaturation, i.e. a carbon-carbon, sp triple bond. Examples include, but are not limited to: ethynyl (—C≡CH) and propargyl (—$CH_2$—C≡CH). In a particular embodiment, alkyl, alkenyl or alkynyl can be divided in $C_1$-$C_{16}$ and $C_{17}$-$C_{30}$.

As used herein and unless otherwise stated, the term "halogen" means any atom selected from the group consisting of fluorine (F), chlorine (Cl), bromine (Br) and iodine. As used herein with respect to a substituting group, and unless otherwise stated, the term "aryl" designate any mono- or polycyclic aromatic monovalent hydrocarbon radical having from 6 up to 30 carbon atoms such as but not limited to phenyl, naphthyl, anthracenyl, phenantracyl, fluoranthenyl, chrysenyl, pyrenyl, biphenylyl, terphenyl, picenyl, indenyl, biphenyl, indacenyl, benzocyclobutenyl, benzocyclooctenyl and the like, including fused benzo-$C_{4-8}$ cycloalkyl groups such as, for instance, indanyl, tetrahydronaphtyl, fluorenyl and the like, all of the said groups being optionally substituted with one or more substituents independently selected from the group consisting of halogen, amino, trifluoromethyl, hydroxyl, sulfhydryl and nitro, such as for instance 4-fluorophenyl, 4-chlorophenyl, 3,4-dichlorophenyl, 4-cyanophenyl, 2,6-dichlorophenyl, 2-fluorophenyl, 3-chlorophenyl, 3,5-dichlorophenyl and the like.

The term "DNA virus" is used as known by a person skilled in the art. DNA viruses are normally classified as following (non-limiting examples of virus member genus or species are given together with some non-limiting examples of the diseases caused by said viruses):

Parvoviridae: e.g. parvoviruses (roseola, fetal death, gastroenteritis);

Papillomaviridae: e.g. human papilloma viruses ("HPV"—benign warts and genital warts, epithelial cell proliferation such as in genital and rectal cancers);

Adenoviridae: e.g. adenoviruses (respiratory infections, gastroenteritis, infectious pinkeye, rashes, meningoencephalitis)

Poxviridae: e.g. variola virus (smallpox), vaccinia virus, molluscipox virus (molluscum contagiosum-wartlike skin lesions).

Herpesviridae: e.g. herpes simplex 1 virus ("HSV-1"; most oral herpes), herpes simplex 2 virus ("HSV-2"; most genital herpes), herpes simplex 6 virus (HSV-6; roseola), varicella-zoster virus ("VZV"; chickenpox and shingles), Epstein-Barr virus ("EBV"; infectious mononucleosis and lymphomas), cytomegalovirus ("CMV"; birth defects and infections of a variety of body systems in immunosuppressed individuals);

Polyomaviridae: e.g. polyomavirus JC and BK (demyelinitazing disorders, nephritis in immunosuppressed individuals).

The term DNA virus also includes the family of the Hepadnaviridae to which Hepatitis B virus belongs.

The term "cell proliferative disorders" as used herein refers to disorders in which there is an abnormal or hyperproliferation of cells compared to physiological circumstances. Cell proliferative disorders comprises, but is not limited to, cancer, tumor formation or psoriasis, in a particular embodiment when the causative agent or agent contributing to the disorder is a DNA virus. When the cell proliferative disorders is induced by a virus, the term "virus-induced cell proliferative disorders" will be used.

The terminology used to denote the compounds of the invention is based on well known abbreviations in the prior art. As an example, HPMPC refers to cidofovir or [(S)-1-(3-hydroxy-2-phosphonylmethoxypropyl)cytosine, the active component of Vistide®. In this way, the 5-aza-cytosine derivatives of the present invention are referred to with analoguous abbreviations. As an example, (S)-1-(3-hydroxy-2-phosphonyl-methoxypropyl)-5-azacytosine is referred to as 5-aza-HPMPC, HPMP-5-azaC, HPMP-5-azacytosine and analoguous ways. For denoting phosphonate cytosine derivatives which have a cyclic phosphonate ester, the term "cyclic" or "c" can be used before the abbreviation, such as in cyclic HPMPC or cHPMPC.

In the present invention, new compounds are provided. The compounds are novel 5-azacytosine derivatives and it has been shown that they possess antiviral activity, more specifically against DNA viruses and that they are active against virus-induced cell proliferative disorders. The present invention demonstrates that the compounds inhibit the replication of DNA viruses in vitro and in vivo such a pox-, herpes- and papilloma-viruses. Therefore, these compounds constitute a new potent class of medicines that can be used in the treatment and prevention of virus-induced cell proliferative disorders or viral infections in animals, mammals and humans. The present invention furthermore shows that, compared to HPMPC, the novel 5-azacytosine derivatives are more active against most DNA-viruses and are less toxic. The compounds are 5-azacytosine derivatives according to the formula hereunder presented:

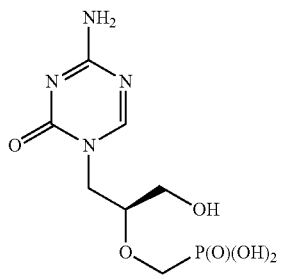

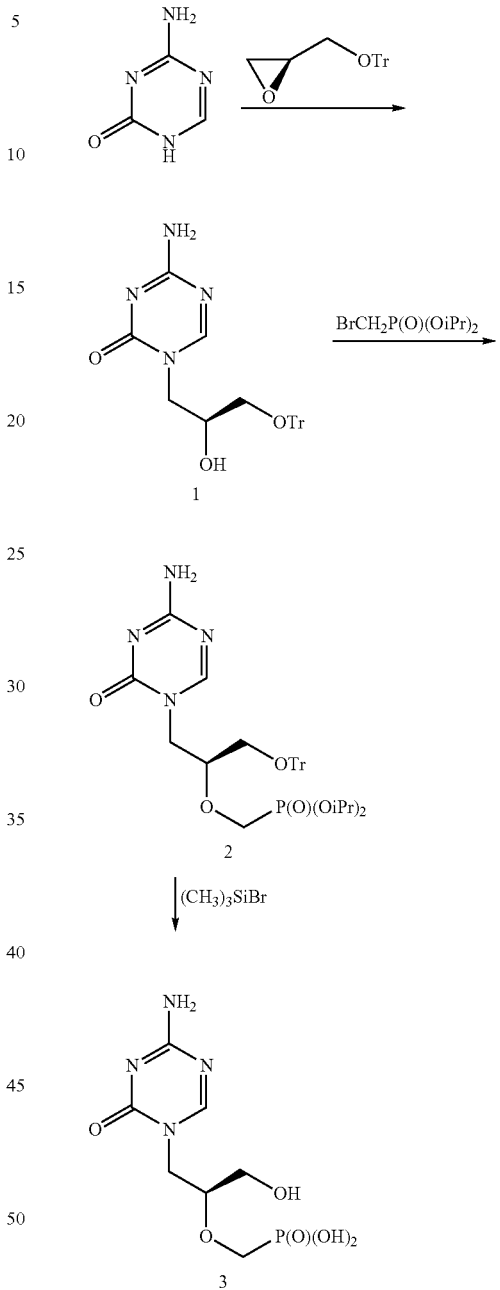

The invention relates also to isomers, solvates, tautomers, salts, esters, amidates, esteramidates or pharmaceutically acceptable salts of the compound of the formula hereabove or to compounds in equilibrium with the compound of the formula hereabove. It is known in the art that the phosphonate function of nucleoside analogs can be derivatized in order to increase the activity, the pharmacokinetic or -dynamic profile or other reasons. Therefore, the present invention also relates to the phosphonate esters, amidates or esteramidates, wherein the phosphonate can be mono- or disubstituted. Examples of such esters comprise alkyl esters, alkenyl esters, alkynyl esters, alkoxyalkyl esters, alkoxyalkenyl esters such as octyl, tetracosyl, hexadecyloxypropyl, octadecyloxyethyl, oleyloxypropyl, tetradecyloxypropyl, octadecyloxypropyl, oleyloxyethyl, 1-O-octadecyl-2-O-benzyl-glyceryl and the like as described in the prior art (i.e. Keith K. A. et al. Antimicrobial agents and chemotherapy 2004, 1869-1871; Ciesla, S. L. et al Antiviral Research 2003, 59, 163-171 and are incorporated herein by reference). In a particular embodiment the esters have at least 16-carbon atoms.

Also conversion to the cyclic ester with a lower polarity or neutral hydrophobic cyclic diester are possible.

The compounds according to invention can be prepared by different methods. For example, suspension of 5-azacytosine heated with (2S)-2-[(trityloxy)methyl]oxirane in dipolar aprotic solvent as e.g. dry dimethylsulfoxide (to 120° C. in the presence of alkaline catalyst (e.g. solid sodium hydroxide) gives the trityl intermediate 1 which affords on treatment with dialkyl (preferably diisopropyl) bromomethylphosphonate in an aprotic solvent (dimethylformamide, dioxane, dimethylsulfoxide, tetrahydrofuran, etc.), and a strong base, eg, sodium hydride, sodium or potassium alkoxide (preferably t-butoxide), DBU (Diaza(1,3)bicyclo[5.4.0]undecane) and the like the fully protected phosphonate diester 2 which can be easily isolated preferably by silica gel chromatography. In the above steps, the trityl group may be replaced with any O-protecting group well known in the art. The diester 2 is then deprotected by cleavage of both the phosphonate ester and trityl groups. It can be performed simultaneously by treatment with iodotrimethylsilane, bromotrimethylsilane or the mixture of chlorotrimethylsilane and potassium iodide in an inert solvent, preferably acetonitrile, dimethylformamide, chlorinated solvents and the like. The further procedure involves hydrolysis, product isolation and purification.

An alternative method (as shown in scheme 3), based on milder conditions more suitable for the chemically sensitive triazine heterocycle, affords a compound of identical physico-chemical and biological characteristics. This alternative comprises the condensation of 5-azacytosine sodium salt, generated preferably in situ by treatment of 5-azacytosine with one equivalent of sodium hydride in dimethylformamide with the so-called "HPMP-synthon" 8, i.e. 2(S)-2-[(diisopropyloxyphosphoryl)methoxy]-3-hydroxypropyl p-tolylsulfonate. This affords the diester 9 of 5-azacytosine which is ultimately treated with bromotrimethylsilane and worked-up as in the first procedure.

Scheme 2: Synthesis of the HPMP-synthon.

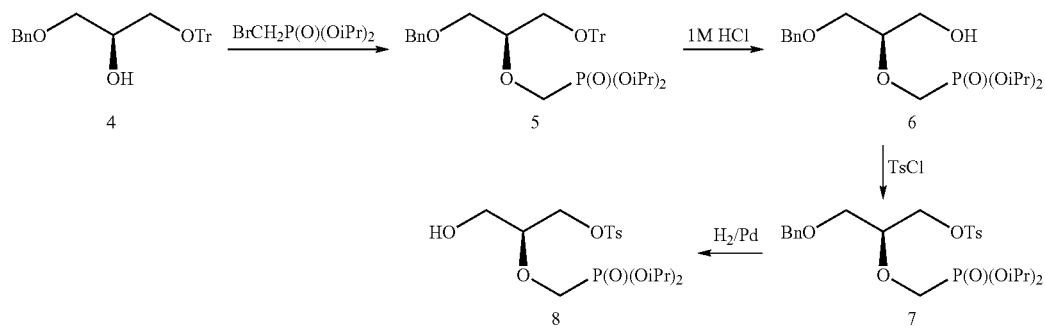

Scheme 3: Synthesis of (S)-1-[3-hydroxy-2-(phosphonomethoxy)propyl]-5-azacytosine from the HPMP-synthon

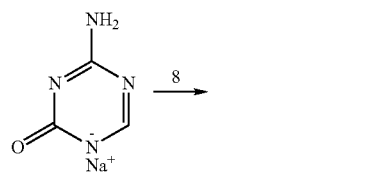

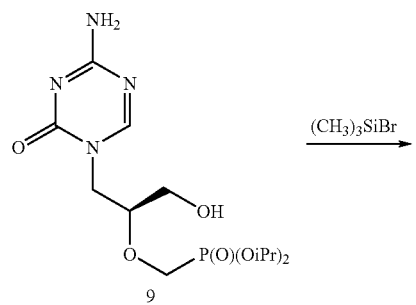

with benzyl halogenide and a base (preferably sodium hydride or potassium hydroxide) followed by acid treatment to the optically active 1-O-benzylglycerol (also available commercially) which is, in turn, converted to the 3-O-trityl derivative. Condensation of this compound with disopropyl bromomethylphosphonate as described above, detritylation, tosylation of the free hydroxyl at the position 1 by treatment with p-tolylsulfonylchloride in pyridine or in a chlorinated solvent in the presence of tertiary amine (preferably triethylamine or diisopropylethylamine) and hydrogenolysis of the benzyl protecting group, preferably over palladium-on-carbon catalyst affords the HPMP-synthon.

6-alkyl derivatives can be synthesised according to any of the three methods described below if the alkyl in position 6 is a $C_{1-4}$ alkyl.

Method I

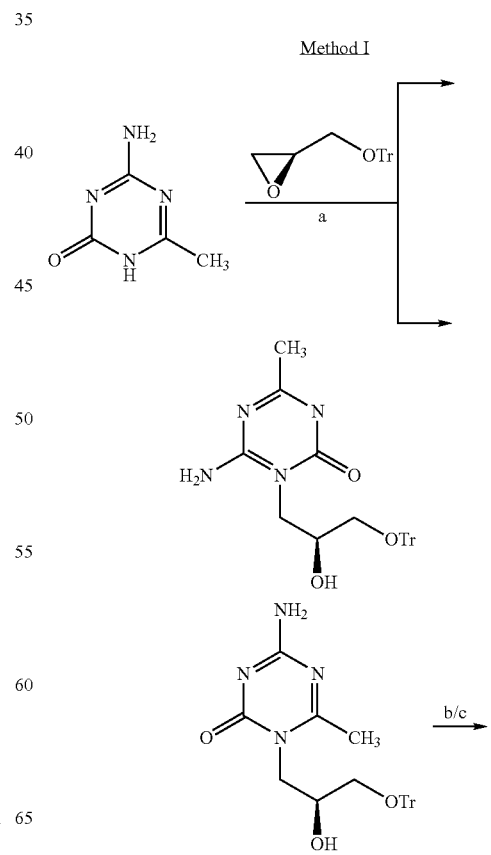

The HPMP-synthon is preferably prepared prior to the alkylation of 5-azacytosine by the earlier described procedure starting from commercially available optically active 2,3-O-isopropylideneglycerol (or also named 2,2-dimethyl-4-hydroxymethyl-1,3-dioxolane) as described in accordance with Holy A. et al. Nucleosides & Nucleotides 1995, 14, 695-702. Briefly, the starting material is transformed by benzylation

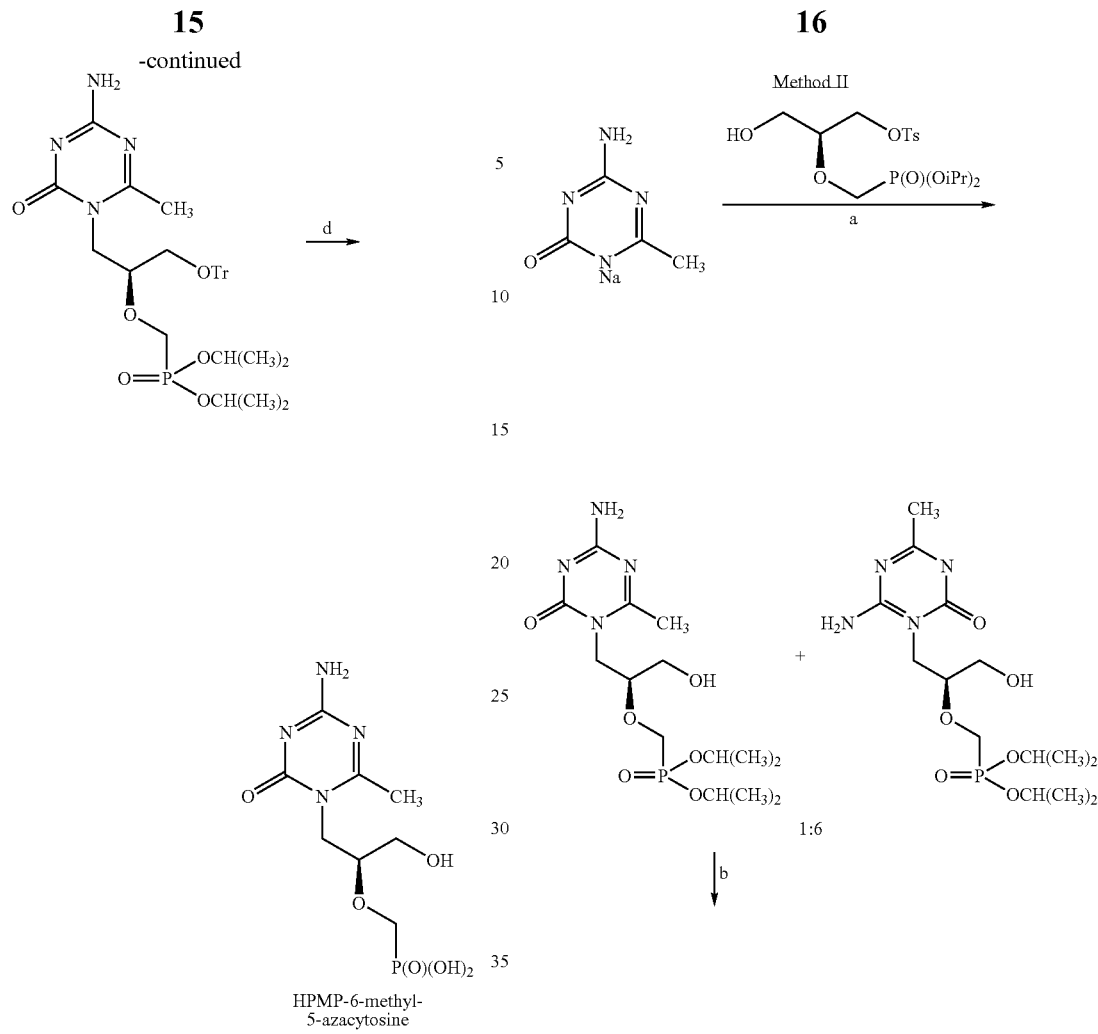

HPMP-6-methyl-5-azacytosine

Conditions: (a) DMSO, NaOH, 120° C., 6 h; (b) BrCH$_2$P(O)(OiPr)$_2$, sodium t-butoxide, dioxane, 100° C., 4 h/or: (c) TsOCH$_2$P(O)(OiPr)$_2$, NaH, DMF, r.t., 20 h; (d) (CH$_3$)$_3$SiBr, CH$_3$CN, r.t., 24 h The general procedure of method I consists in a first step in heating up to about 120° C. a suspension of 4-amino-6-alkyl-1,3,5-triazin-2(1H)-one and (2S)-2-[(trityloxy)methyl]oxirane in dipolar aprotic solvent such as e.g. dry dimethylsulfoxide in presence of an alkaline catalyst (e.g. solid sodium hydroxide). This first step gives as a main product the trityl intermediate. In a second step, this trityl intermediate is reacted with a dialkyl (preferably diisopropyl) bromomethylphosphonate or a dialkyl (tosyloxy)methylphosphonate in an aprotic solvent (dimethylformamide, dioxane, dimethylsulfoxide, tetrahydrofuran, etc.) in presence of a strong base (such as e.g. sodium hydride, sodium or potassium alkoxide (preferably t-butoxide), DBU (Diaza(1,3)bicyclo[5.4.0]undecane) and the like) to give the fully protected phosphonate diester which can be easily isolated preferably by silica gel chromatography.

In the above steps, the trityl group may be replaced with any O-protecting group well known in the art. The diester is then deprotected by cleavage of both the phosphonate ester and trityl groups. It can be performed simultaneously by treatment with iodotrimethylsilane, bromotrimethylsilane or the mixture of chlorotrimethylsilane and potassium iodide in an inert solvent, preferably acetonitrile, dimethylformamide, chlorinated solvents and the like. The further procedure involves hydrolysis, product isolation and purification.

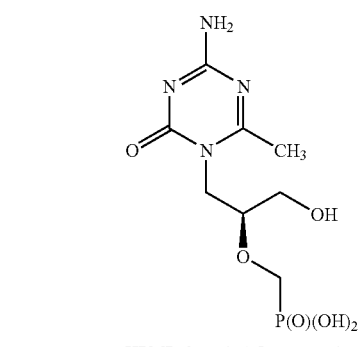

HPMP-6-methyl-5-azacytosine

Conditions: (a) DMF, 120° C., 5 h; (b) (CH$_3$)$_3$SiBr, CH$_3$CN, r.t., 24 h

This second method comprises the condensation of 4-amino-6-alkyl-1,3,5-triazin-2(1H)-one sodium salt, generated preferably in situ by treatment of 4-amino-6-alkyl-1,3,5-triazin-2(1H)-one with one equivalent of sodium hydride in dimethylformamide with the so-called "HPMP-synthon" 8, i.e. 2(S)-2-[(diisopropyloxyphosphoryl)methoxy]-3-hydroxypropyl p-tolylsulfonate. This affords the diester of 4-amino-6-alkyl-1,3,5-triazin-2(1H)-one which is ultimately treated with bromotrimethylsilane and worked-up as in the first method.

Method III

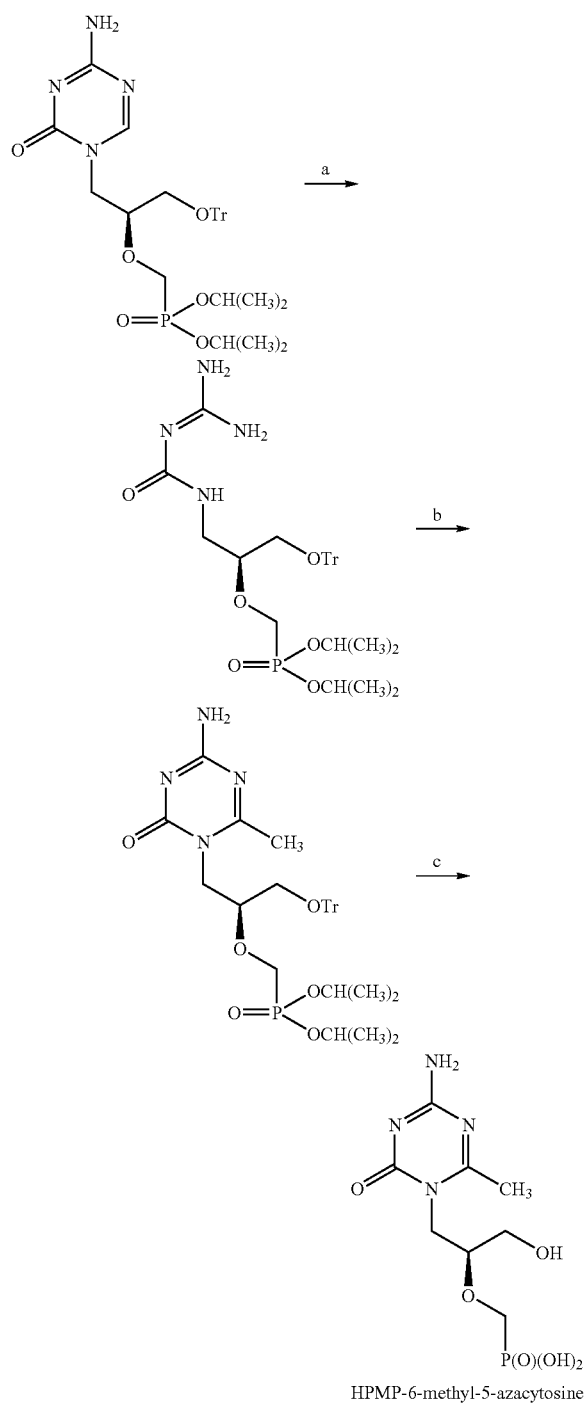

Conditions: (a) 25% aq. NH$_4$OH+CH$_3$OH 1:1, r.t., 5 days; (b) Triethyl orthoacetate, DMF, 150° C., 3 h; (c) (CH$_3$)$_3$SiBr, CH$_3$CN, r.t., 24 h Generally, a mixture of 2 with aqueous ammonia in methanol is stirred at room temperature for a few days. The mixture is evaporated and the residue coevaporated with absolute ethanol to give an oily residue of an intermediate product. This material is then dissolved in DMF and heated with appropriate orthoester at about 150° C. for a few hours. The mixture is then evaporated, the residue chromatographed on a column of silica gel. Deprotection performed by the same procedure as described for HPMP-5-azaC leads to final 6-alkyl HPMP-5-azaC.

Alternatively, and for longer alkyl chains, the 6-alkyl derivatives can be prepared as exemplified in example 16.

Similarly as the other N$^1$-substituted 5-azacytosine derivatives (riboside, 2-deoxyriboside, arabinoside, . . . ), also the 5-aza analogue of HPMPC undergoes in aqueous solution slow decomposition which proceeds according to scheme 4 hereunder.

Scheme 4: Equilibrium with sodium 3-Formyl-2-{[(2S)-3-Hydroxy-2-(phosphonomethoxy)propyl]carbamoyl}guanidine (3a) and degradation thereof

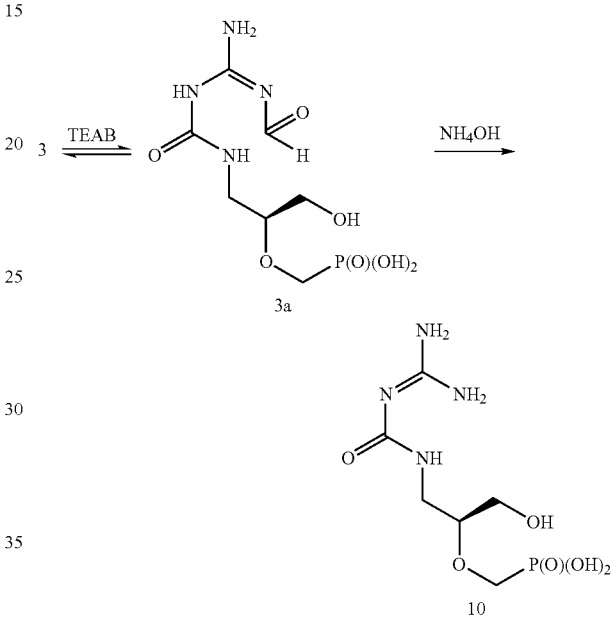

The first step is a reversible opening of the sym-triazine ring to the N-formylguanidine derivative which can close back to the cyclic structure. This step occurs in presence of a trialkylammonium buffer, e.g. triethylammonium hydrogenocarbonate (TEAB), triethylammonium hydroxide or triethylammonium acetate. This hydrolytic reaction is slow and reaches equilibrium within several days. It is accompanied by loss of UV-absorption which allows to determine its course. The ring-open product 3a when applied to the biological systems thus possesses activity identical with that of 5-aza-HPMPC itself.

However, this reversible ring-opening hydrolysis is accompanied by irreversible deformylation reaction of the formyl derivative that gives rise to the antivirally inactive 2-{[(2S)-3-hydroxy-2-(phosphonomethoxy)propyl]carbamoyl}guanidine (10). Though this reaction is generally controlled by acidobasic catalysis, it could be eventually speeded up (or slowed down) in vivo by the action of enzymes.

As in HPMPC and nucleotides with antiviral or anticancer activity, the polar character of the phosphonate group interferes with the transport of the compound into the cell and, specifically, it limits the use for oral application of the drug. Equally as it is in the former cases, this obstacle can be overcome by conversion to the cyclic ester with a lower polarity, neutral hydrophobic diester or cyclic diester, esteramidates, bisamidates and the like. The methods for their preparation are identical to those described in the prior art.

Esters of compound 3 such as cyclic esters, alkyl esters or alkoxyalkyl esters, can be prepared according to the following scheme:

Alternatively, esters of compound 3 can also be prepared according to scheme 6:

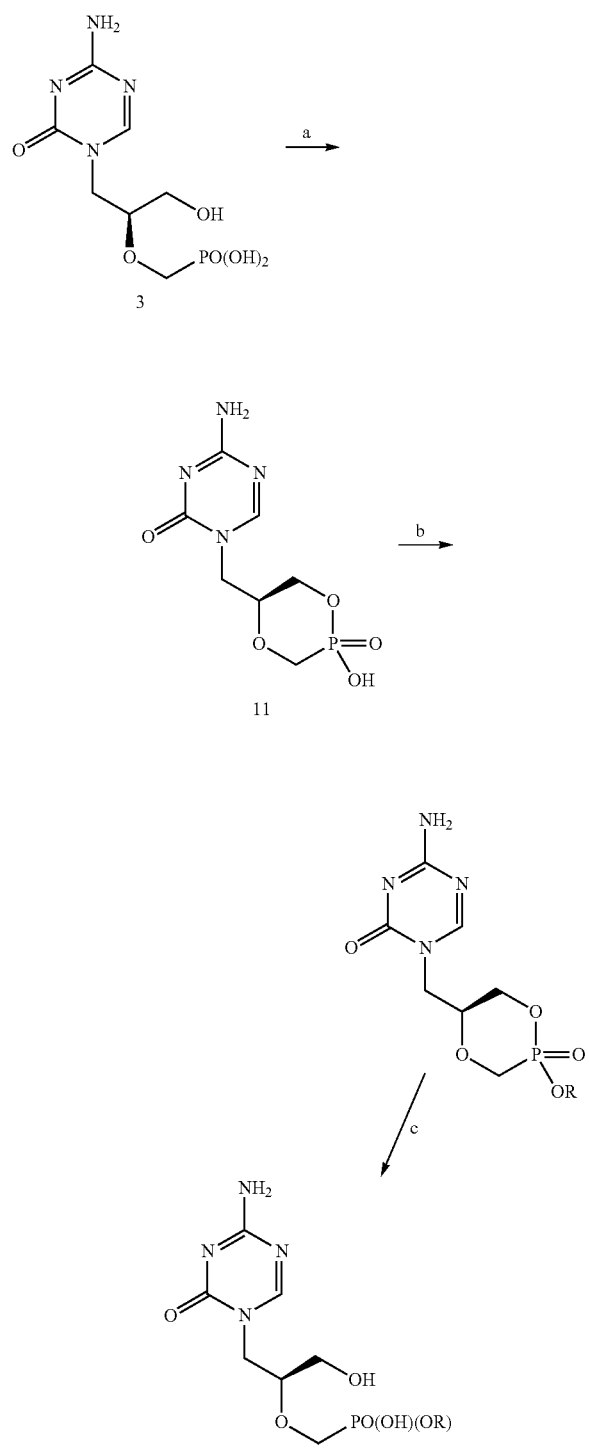

Reagents: a. N,N-dicyclohexyl-4-morpholinocarboxamidine, 1,3-dicyclohexylcarbodiimide in DMF at elevated temperature; b. (i) R—OH, 1,3-dicyclohexylcarbodiimide and dimethylaminopyridine in DMF at elevated temperature or (ii) R-halogenide such as R-halogen (such as RBr) in DMF at elevated temperature; c. 0.5 M NaOh (i.e. as described in Beadle, J.R. et al. Antimicrob. Agents Chemother. 2002, 2381-2386)

Reagents: a. N,N-dicyclohexyl-4-morpholinocarboxamidine, R-halogen (such as RCl) in DMF. Separation of the products is possible with standard techniques known to the skilled person in the art.

The synthesis of bis-phosphoramidates, mono-phosphoroamidates or mixed amidate-ester analogs of the nucleotide analog phosphonates according to the invention can be prepared according to procedures known in the art, for example as described in U.S. Pat. No. 5,798,340. For the creation of phosphoroamidates, amino acids or other molecules bearing a free amine (not tertiary amines) can be used.

Synthesis of the bis-phosphoramidates can be accomplished by directly converting the free nucleotide analog such as (S)-1-[3-hydroxy-2-(phosphonomethoxy)propyl]-5-azacytosine to the corresponding bis-phosphoroamidate compound. The synthesis comprises the mixing of the free nucleotide analog in a solvent such as dry DMF with approximately 2 equivalents of free amines or amino acids, optionally further containing a non-nucleophilic organic base such as triethylamine (3 to 10 equivalents). The dehydration step is accomplished by adding to the previous mixture a 1:1 mixture of triphenylphosphine and 2,2'-dipyridyl disulfide (2 to 4 equivalents) and (a) stirring at RT for about 4 to 16 h or (b) heating to 60° C. to 100° C. for about 4 to 16 hours. The final bis-amidate product is recovered and purified by conventional methods.

An alternative reaction for synthesising some phosphoroamidates is converting a nucleotide analog phosphonate to the corresponding chloridate by reaction with thionyl chloride in a solvent as described in EP481214. An amino acid or other molecule bearing a free amine is then reacted with the chloridate to yield the corresponding bis-amidate. Mono-phosphoramidates or mixed ester-phosphoramidates can be synthesised as follow: For example, a bis-ester can be converted to a mixed ester-phosphoramidate by first converting the bis-ester to a mono-ester by treatment with a weak base to remove one ester group and in a second step to convert it to the amidate. Also esters of the cyclic HPMP-5-azaC can be converted to phosphoramidates of the cyclic HPMP-5-azaC, by first removing the ester in weak base (such as 0.5M NaOH) and than converting it to the amidate.
The conversion to the amidate can be performed as described for Bis-phosphoramidates.

In a particular embodiment, formula (I) corresponds to the following compound.

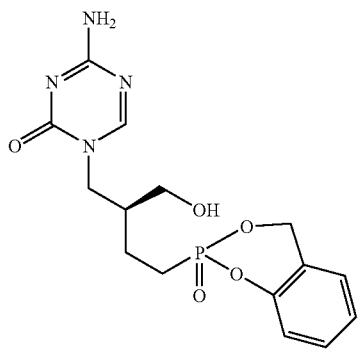

This compound can be synthesised by following a procedure analog to these described in "*cycloSal-PMEA and cycloAmb-PMEA: Potentially New Phosphonate Prodrugs Based on the cycloSal-Pro-nucleotide Approach. Journal of Medicinal Chemistry* (2005), 48, (25), 8079-8086."

In another particular embodiment of the present invention, 6-azacytosine derivatives analogues can be prepared as follow. The synthesis of 6-azacytosine congener is based on the 6-azacytosine reaction with trityloxymethyl-(2S)-oxirane; subsequent N[4]-benzoylation of the base moiety gives an intermediate product. Its reaction with diisopropyl p-tolylsulfonyloxymethylphosphonate gives the fully protected phosphonate derivative. Using standard deprotection techniques, the 6-aza analogue of cidofovir can be obtained from this intermediate.

The compounds of the invention have been found to inhibit viral replication, especially of DNA viruses, and to inhibit virus-induced cell proliferative disorders such as cancer in vitro and in vivo. The compounds have shown a potent activity against different viruses of the families of the Herpesviridae, the Orthopoxviridae and the Papillomaviridae. They have been shown to inhibit the replication of different strains of Herpes simplex virus, Cytomegalovirus, Varicella-Zoster Virus, Vaccinia virus, Cowpox virus, Orf virus and Human Papilloma virus amongst others. The compounds have also been shown to inhibit virus-induced cell proliferative disorders such as tumor formation and cancer. In a particular embodiment, the compounds of the invention can also be used for the prevention or treatment of infections caused by viruses of the Retroviridae such as HIV (Human immunodeficiency virus).

Thus, 5-aza-HPMPC combines in its structure both the strong antineoplastic activity and antiviral effects aimed at the DNA viruses (specifically pox- and herpesviruses) which often occur in immunosuppressed patients and cause complications in the cancer chemotherapy.

Thereby, the present invention provides compounds that can be used as a medicine and can be used for the manufacture of a medicament for the prevention or treatment of viral infections or virus-induced cell proliferative disorders in mammals, more specifically humans. The present invention further provides a method for preventing or treating a viral infection or a virus-induced cell proliferative disorder in a subject or patient by administering to the patient in need thereof a therapeutically effective amount of 5-azacytosine derivative of the present invention.

The compounds of the invention are employed for the treatment or prophylaxis of viral infections, more particularly DNA virus infections. When using one or more compounds according to the formulas of the application like (I) or (II) as defined herein:

the active ingredients of the compound(s) may be administered to the mammal (including a human) to be treated by any means well known in the art, i.e. orally, intranasally, subcutaneously, intramuscularly, intradermally, intravenously, intra-arterially, parenterally or by catheterization.

the therapeutically effective amount of the preparation of the compound(s), especially for the treatment of viral infections in humans and other mammals, preferably is a DNA viral enzyme inhibiting amount. More preferably, the DNA-viral replication inhibiting amount or a DNA-viral enzyme inhibiting amount of the derivative(s) of formula (I) or (II) as defined herein corresponds to an amount which ensures a plasma level of between 1 pg/ml and 100 mg/ml. This can be achieved by administration of the required dosage to obtain such plasma levels, thereby depending upon the pathologic condition to be treated and the patient's condition, the said effective amount may be divided into several sub-units per day or may be administered at more than one day intervals.

As is conventional in the art, the evaluation of a synergistic effect in a drug combination may be made by analyzing the quantification of the interactions between individual drugs, using the median effect principle described by Chou et al. in *Adv. Enzyme Reg.* (1984) 22:27. Briefly, this principle states that interactions (synergism, additivity, antagonism) between two drugs can be quantified using the combination index (hereinafter referred as CI) defined by the following equation:

$$CI_x = \frac{ED_x^{1c}}{ED_x^{1a}} + \frac{ED_x^{2c}}{ED_x^{2a}}$$

wherein $ED_x$ is the dose of the first or respectively second drug used alone (1a, 2a), or in combination with the second or respectively first drug (1c, 2c), which is needed to produce a given effect. The said first and second drug have synergistic or additive or antagonistic effects depending upon CI<1, CI=1, or CI>1, respectively.

Synergistic activity of the pharmaceutical compositions or combined preparations of this invention against viral infection may also be readily determined by means of one or more tests such as, but not limited to, the isobologram method, as previously described by Elion et al. in *J. Biol. Chem.* (1954) 208:477-488 and by Baba et al. in *Antimicrob. Agents Chemother.* (1984) 25:515-517, using $EC_{50}$ for calculating the fractional inhibitory concentration (hereinafter referred as FIC). When the minimum FIC index corresponding to the FIC of combined compounds (e.g., $FIC_x+FIC_y$) is equal to 1.0, the combination is said to be additive; when it is between 1.0 and 0.5, the combination is defined as subsynergistic, and when it is lower than 0.5, the combination is defined as synergistic. When the minimum FIC index is between 1.0 and 2.0, the combination is defined as subantagonistic and, when it is higher than 2.0, the combination is defined as antagonistic. This principle may be applied to a combination of different antiviral drugs of the invention or to a combination of the antiviral drugs of the invention with other drugs that exhibit anti-DNA-virus activity.

The invention thus relates to a pharmaceutical composition or combined preparation having synergistic effects against a viral infection and containing either:

A)
(a) a combination of two or more of the 5-azacytosine derivatives of the present invention, and
(b) optionally one or more pharmaceutical excipients or pharmaceutically acceptable carriers,
for simultaneous, separate or sequential use in the treatment or prevention of a viral infection, or
B)
(c) one or more antiviral agents, and
(d) at least one of the 5-azacytosine derivatives of the present invention, and
(e) optionally one or more pharmaceutical excipients or pharmaceutically acceptable carriers,
for simultaneous, separate or sequential use in the treatment or prevention of a viral infection.

Suitable antiviral agents for inclusion into the synergistic antiviral compositions or combined preparations of this invention include anti-DNA-virus compounds such as but not limited to Acyclovir and its prodrug valacyclovir (e.g. active against alpha-herpesviruses HSV and VZV), Ganciclovir and its prodrug valganciclovir (e.g. active against beta-herpesviruses HHV-6 and HCMV and alpha herpesviruses HSV and VZV), Foscavir (e.g. active against alpha- and beta-herpesviruses), Brivudin (e.g. active against HSV-1 and VZV), Cidofovir (e.g. active against all DNA viruses except hepatitis B), Adefovir (e.g. active against all herpesviruses and hepatitis B) or Lamivudine (e.g. active against hepatitis B).

The pharmaceutical composition or combined preparation with synergistic activity against viral infection according to this invention may contain 5-azacytosine derivative of the present invention, compounds according to the formulas of the application like (I) or (II), over a broad content range depending on the contemplated use and the expected effect of the preparation. Generally, the content of the 5-azacytosine derivatives of the present invention of the combined preparation is within the range of 0.1 to 99.9% by weight, preferably from 1 to 99% by weight, more preferably from 5 to 95% by weight.

According to a particular embodiment of the invention, the compounds of the invention may be employed in combination with other therapeutic agents for the treatment or prophylaxis of viral infections or cell proliferative disorders. The invention therefore relates to the use of a composition comprising:
(a) one or more compounds of formula (I) or (II), and
(b) one or more viral replication inhibitors or cell proliferation inhibitors as biologically active agents for instance in the form of a combined preparation for simultaneous, separate or sequential use in viral infection or cell proliferative disorder therapy.

The present invention further provides veterinary compositions comprising at least one active ingredient as above defined together with a veterinary carrier therefore. Veterinary carriers are materials useful for the purpose of administering the composition and may be solid, liquid or gaseous materials which are otherwise inert or acceptable in the veterinary art and are compatible with the active ingredient. These veterinary compositions may be administered orally, parenterally or by any other desired route.

More generally, the invention relates to the compounds according to the formulas of the application like (I) or (II) being useful as agents having biological activity (particularly antiviral activity) or as diagnostic agents. Any of the uses mentioned with respect to the present invention may be restricted to a non-medical use, a non-therapeutic use, a non-diagnostic use, or exclusively an in vitro use, or a use related to cells remote from an animal.

The compounds of the invention optionally are bound covalently to an insoluble matrix and used for affinity chromatography (separations, depending on the nature of the groups of the compounds, for example compounds with aryl are useful in hydrophobic affinity separations.

Those of skill in the art will also recognize that the compounds of the invention may exist in many different protonation states, depending on, among other things, the pH of their environment. While the structural formulae provided herein depict the compounds in only one of several possible protonation states, it will be understood that these structures are illustrative only, and that the invention is not limited to any particular protonation state, any and all protonated forms of the compounds are intended to fall within the scope of the invention.

The term "pharmaceutically acceptable salts" as used herein means the therapeutically active non-toxic salt forms which the compounds according to the formulas of the application like (I) or (II) are able to form. Therefore, the compounds of this invention optionally comprise salts of the compounds herein, especially pharmaceutically acceptable non-toxic salts containing, for example, $Na^+$, $Li^+$, $K^+$, $Ca^{+2}$ and $Mg^{+2}$. Such salts may include those derived by combination of appropriate cations such as alkali and alkaline earth metal ions or ammonium and quaternary amino ions with an acid anion moiety, typically a carboxylic acid. The compounds of the invention may bear multiple positive or negative charges. The net charge of the compounds of the invention may be either positive or negative. Any associated counter ions are typically dictated by the synthesis and/or isolation methods by which the compounds are obtained. Typical counter ions include, but are not limited to ammonium, sodium, potassium, lithium, halides, acetate, trifluoroacetate, etc., and mixtures thereof. It will be understood that the identity of any associated counter ion is not a critical feature of the invention, and that the invention encompasses the compounds in association with any type of counter ion. Moreover, as the compounds can exist in a variety of different forms, the invention is intended to encompass not only forms of the compounds that are in association with counter ions (e.g., dry salts), but also forms that are not in association with counter ions (e.g., aqueous or organic solutions). Metal salts typically are prepared by reacting the metal hydroxide with a compound of this invention. Examples of metal salts which are prepared in this way are salts containing $Li^+$, $Na^+$, and $K^+$. A less soluble metal salt can be precipitated from the solution of a more soluble salt by addition of the suitable metal compound. In addition, salts may be formed from acid addition of certain organic and inorganic acids to basic centers, typically amines, or to acidic groups. Examples of such appropriate acids include, for instance, inorganic acids such as hydrohalic acids, e.g. hydrochloric or hydrobromic acid, sulfuric acid, nitric acid, phosphoric acid and the like; or organic acids such as, for example, acetic, propanoic, hydroxyacetic, 2-hydroxypropanoic, 2-oxopropanoic, lactic, pyruvic, oxalic (i.e. ethanedioic), malonic, succinic (i.e. butanedioic acid), maleic, fumaric, malic, tartaric, citric, methanesulfonic, ethanesulfonic, benzenesulfonic, p-toluenesulfonic, cyclohexanesulfamic, salicylic (i.e. 2-hydroxybenzoic), p-aminosalicylic and the like. Furthermore, this term also includes the solvates which the compounds according to the formulas of the application like (I) or (II) as well as their salts are able to form, such as for example hydrates, alcoholates and the like. Finally, it is to be understood that the compositions herein comprise compounds of the invention in their unionized, as well as zwitterionic form, and combinations with stoichiometric amounts of water as in hydrates.

Also included within the scope of this invention are the salts of the parental compounds with one or more amino acids, especially the naturally-occurring amino acids found as protein components. The amino acid typically is one bearing a side chain with a basic or acidic group, e.g., lysine, arginine or glutamic acid, or a neutral group such as glycine, serine, threonine, alanine, isoleucine, or leucine.

The compounds of the invention also include physiologically acceptable salts thereof. Examples of physiologically acceptable salts of the compounds of the invention include salts derived from an appropriate base, such as an alkali metal (for example, sodium), an alkaline earth (for example, magnesium), ammonium and $NX_4^+$ (wherein X is $C_1$-$C_4$ alkyl). Physiologically acceptable salts of an hydrogen atom or an amino group include salts of organic carboxylic acids such as acetic, benzoic, lactic, fumaric, tartaric, maleic, malonic, malic, isethionic, lactobionic and succinic acids; organic sulfonic acids, such as methanesulfonic, ethanesulfonic, benzenesulfonic and p-toluenesulfonic acids; and inorganic acids, such as hydrochloric, sulfuric, phosphoric and sulfamic acids. Physiologically acceptable salts of a compound containing a hydroxy group include the anion of said compound in combination with a suitable cation such as $Na^+$ and $NX_4^+$ (wherein X typically is independently selected from H or a $C_1$-$C_4$ alkyl group). However, salts of acids or bases which are not physiologically acceptable may also find use, for example, in the preparation or purification of a physiologically acceptable compound. All salts, whether or not derived form a physiologically acceptable acid or base, are within the scope of the present invention.

As used herein and unless otherwise stated, the term "enantiomer" means each individual optically active form of a compound of the invention, having an optical purity or enantiomeric excess (as determined by methods standard in the art) of at least 80% (i.e. at least 90% of one enantiomer and at most 10% of the other enantiomer), preferably at least 90% and more preferably at least 98%.

The term "isomer" as used herein means all possible isomeric forms, including tautomeric and stereochemical forms, which the compounds according to the formulas of the application like (I) or (II) may possess, but not including position isomers. Typically, the structures shown herein exemplify only one tautomeric or resonance form of the compounds, but the corresponding alternative configurations are contemplated as well. Unless otherwise stated, the chemical designation of compounds denotes the mixture of all possible stereochemically isomeric forms, said mixtures containing all diastereomers and enantiomers (since the compounds according to the formulas of the application like (I) or (II) may have at least one chiral center) of the basic molecular structure, as well as the stereochemically pure or enriched compounds. More particularly, stereogenic centers may have either the R- or S-configuration, and multiple bonds may have either cis- or trans-configuration. Pure isomeric forms of the said compounds are defined as isomers substantially free of other enantiomeric or diastereomeric forms of the same basic molecular structure. In particular, the term "stereoisomerically pure" or "chirally pure" relates to compounds having a stereoisomeric excess of at least about 80% (i.e. at least 90% of one isomer and at most 10% of the other possible isomers), preferably at least 90%, more preferably at least 94% and most preferably at least 97%. The terms "enantiomerically pure" and "diastereomerically pure" should be understood in a similar way, having regard to the enantiomeric excess, respectively the diastereomeric excess, of the mixture in question. Separation of stereoisomers is accomplished by standard methods known to those in the art. One enantiomer of a compound of the invention can be separated substantially free of its opposing enantiomer by a method such as formation of diastereomers using optically active resolving agents ("Stereochemistry of Carbon Compounds" (1962) by E. L. Eliel, McGraw Hill; or Lochmuller (1975) *J. Chromatogr.*, 113:(3) 283-302). Separation of isomers in a mixture can be accomplished by any suitable method, including: (1) formation of ionic, diastereomeric salts with chiral compounds and separation by fractional crystallization or other methods, (2) formation of diastereomeric compounds with chiral derivatizing reagents, separation of the diastereomers, and conversion to the pure enantiomers, or (3) enantiomers can be separated directly under chiral conditions. Under method (1), diastereomeric salts can be formed by reaction of enantiomerically pure chiral bases such as brucine, quinine, ephedrine, strychnine, a-methyl-b-phenylethylamine (amphetamine), and the like with asymmetric compounds bearing acidic functionality, such as carboxylic acid and sulfonic acid. The diastereomeric salts may be induced to separate by fractional crystallization or ionic chromatography. For separation of the optical isomers of amino compounds, addition of chiral carboxylic or sulfonic acids, such as camphorsulfonic acid, tartaric acid, mandelic acid, or lactic acid can result in formation of the diastereomeric salts. Alternatively, by method (2), the substrate to be resolved may be reacted with one enantiomer of a chiral compound to form a diastereomeric pair (Eliel, E. and Wilen, S. (1994) Stereochemistry of Organic Compounds, John Wiley & Sons, Inc., p. 322). Diastereomeric compounds can be formed by reacting asymmetric compounds with enantiomerically pure chiral derivatizing reagents, such as menthyl derivatives, followed by separation of the diastereomers and hydrolysis to yield the free, enantiomerically enriched compounds of the invention. A method of determining optical purity involves making chiral esters, such as a menthyl ester or Mosher ester, a-methoxy-a-(trifluoromethyl)phenyl acetate (Jacob III. (1982) J. Org. Chem. 47:4165), of the racemic mixture, and analyzing the NMR spectrum for the presence of the two atropisomeric diastereomers. Stable diastereomers can be separated and isolated by normal- and reverse-phase chromatography following methods for separation of atropisomeric naphthyl-isoquinolines (Hoye, T., WO 96/15111). Under method (3), a racemic mixture of two asymmetric enantiomers is separated by chromatography using a chiral stationary phase. Suitable chiral stationary phases are, for example, polysaccharides, in particular cellulose or amylose derivatives. Commercially available polysaccharide based chiral stationary phases are ChiralCel™ CA, OA, OB5, OC5, OD, OF, OG, OJ and OK, and Chiralpak™ AD, AS, OP(+) and OT(+). Appropriate eluents or mobile phases for use in combination with said polysaccharide chiral stationary phases are hexane and the like, modified with an alcohol such as ethanol, isopropanol and the like. ("Chiral Liquid Chromatography" (1989) W. J. Lough, Ed. Chapman and Hall, New York; Okamoto, (1990) "Optical resolution of dihydropyridine enantiomers by High-performance liquid chromatography using phenylcarbamates of polysaccharides as a chiral stationary phase", J. of Chromatogr. 513:375-378).

The terms cis and trans are used herein in accordance with Chemical Abstracts nomenclature and include reference to the position of the substituents on a ring moiety. The absolute stereochemical configuration of the compounds according to the formulas of the application like (I) or (II) may easily be determined by those skilled in the art while using well-known methods such as, for example, X-ray diffraction or NMR.

The compounds of the invention may be formulated with conventional carriers and excipients, which will be selected in accordance with ordinary practice. Tablets will contain excipients, glidants, fillers, binders and the like. Aqueous formulations are prepared in sterile form, and when intended for delivery by other than oral administration generally will be isotonic. Formulations optionally contain excipients such as those set forth in the "Handbook of Pharmaceutical Excipients" (1986) and include ascorbic acid and other antioxidants, chelating agents such as EDTA, carbohydrates such as dextrin, hydroxyalkylcellulose, hydroxyalkylmethylcellulose, stearic acid and the like.

Subsequently, the term "pharmaceutically acceptable carrier" as used herein means any material or substance with which the active ingredient is formulated in order to facilitate its application or dissemination to the locus to be treated, for instance by dissolving, dispersing or diffusing the said composition, and/or to facilitate its storage, transport or handling without impairing its effectiveness. The pharmaceutically acceptable carrier may be a solid or a liquid or a gas which has been compressed to form a liquid, i.e. the compositions of this invention can suitably be used as concentrates, emulsions, solutions, granulates, dusts, sprays, aerosols, suspensions, ointments, creams, tablets, pellets or powders.

Suitable pharmaceutical carriers for use in the said pharmaceutical compositions and their formulation are well known to those skilled in the art, and there is no particular restriction to their selection within the present invention. They may also include additives such as wetting agents, dispersing agents, stickers, adhesives, emulsifying agents, solvents, coatings, antibacterial and antifungal agents (for example phenol, sorbic acid, chlorobutanol), isotonic agents (such as sugars or sodium chloride) and the like, provided the same are consistent with pharmaceutical practice, i.e. carriers and additives which do not create permanent damage to mammals. The pharmaceutical compositions of the present invention may be prepared in any known manner, for instance by homogeneously mixing, coating and/or grinding the active ingredients, in a one-step or multi-steps procedure, with the selected carrier material and, where appropriate, the other additives such as surface-active agents may also be prepared by inicronisation, for instance in view to obtain them in the form of microspheres usually having a diameter of about 1 to 10 gm, namely for the manufacture of microcapsules for controlled or sustained release of the active ingredients.

Suitable surface-active agents, also known as emulgent or emulsifier, to be used in the pharmaceutical compositions of the present invention are non-ionic, cationic and/or anionic materials having good emulsifying, dispersing and/or wetting properties. Suitable anionic surfactants include both water-soluble soaps and water-soluble synthetic surface-active agents. Suitable soaps are alkaline or alkaline-earth metal salts, unsubstituted or substituted ammonium salts of higher fatty acids ($C_{10}$-$C_{22}$), e.g. the sodium or potassium salts of oleic or stearic acid, or of natural fatty acid mixtures obtainable form coconut oil or tallow oil. Synthetic surfactants include sodium or calcium salts of polyacrylic acids; fatty sulphonates and sulphates; sulphonated benzimidazole derivatives and alkylarylsulphonates. Fatty sulphonates or sulphates are usually in the form of alkaline or alkaline-earth metal salts, unsubstituted ammonium salts or ammonium salts substituted with an alkyl or acyl radical having from 8 to 22 carbon atoms, e.g. the sodium or calcium salt of lignosulphonic acid or dodecylsulphonic acid or a mixture of fatty alcohol sulphates obtained from natural fatty acids, alkaline or alkaline-earth metal salts of sulphuric or sulphonic acid esters (such as sodium lauryl sulphate) and sulphonic acids of fatty alcohol/ethylene oxide adducts. Suitable sulphonated benzimidazole derivatives preferably contain 8 to 22 carbon atoms. Examples of alkylarylsulphonates are the sodium, calcium or alcanolamine salts of dodecylbenzene sulphonic acid or dibutyl-naphtalenesulphonic acid or a naphtalenesulphonic acid/formaldehyde condensation product. Also suitable are the corresponding phosphates, e.g. salts of phosphoric acid ester and an adduct of p-nonylphenol with ethylene and/or propylene oxide, or phospholipids. Suitable phospholipids for this purpose are the natural (originating from animal or plant cells) or synthetic phospholipids of the cephalin or lecithin type such as e.g. phosphatidylethanolamine, phosphatidylserine, phosphatidylglycerine, lysolecithin, cardiolipin, dioctanylphosphatidyl-choline, dipalmitoylphoshatidyl-choline and their mixtures.

Suitable non-ionic surfactants include polyethoxylated and polypropoxylated derivatives of alkylphenols, fatty alcohols, fatty acids, aliphatic amines or amides containing at least 12 carbon atoms in the molecule, alkylarenesulphonates and dialkylsulphosuccinates, such as polyglycol ether derivatives of aliphatic and cycloaliphatic alcohols, saturated and unsaturated fatty acids and alkylphenols, said derivatives preferably containing 3 to 10 glycol ether groups and 8 to 20 carbon atoms in the (aliphatic) hydrocarbon moiety and 6 to 18 carbon atoms in the alkyl moiety of the alkylphenol. Further suitable non-ionic surfactants are water-soluble adducts of polyethylene oxide with poylypropylene glycol, ethylenediaminopolypropylene glycol containing 1 to 10 carbon atoms in the alkyl chain, which adducts contain 20 to 250 ethyleneglycol ether groups and/or 10 to 100 propyleneglycol ether groups. Such compounds usually contain from 1 to 5 ethyleneglycol units per propyleneglycol unit. Representative examples of non-ionic surfactants are nonylphenol-polyethoxyethanol, castor oil polyglycolic ethers, polypropylene/polyethylene oxide adducts, tributylphenoxypolyethoxyethanol, polyethyleneglycol and octylphenoxypolyethoxy-ethanol. Fatty acid esters of polyethylene sorbitan (such as polyoxyethylene sorbitan trioleate), glycerol, sorbitan, sucrose and pentaerythritol are also suitable non-ionic surfactants.

Suitable cationic surfactants include quaternary ammonium salts, particularly halides, having 4 hydrocarbon radicals optionally substituted with halo, phenyl, substituted phenyl or hydroxy; for instance quaternary ammonium salts containing as N-substituent at least one C8C22 alkyl radical (e.g. cetyl, lauryl, palmityl, myristyl, oleyl and the like) and, as further substituents, unsubstituted or halogenated lower alkyl, benzyl and/or hydroxy-lower alkyl radicals.

A more detailed description of surface-active agents suitable for this purpose may be found for instance in "McCutcheon's Detergents and Emulsifiers Annual" (MC Publishing Crop., Ridgewood, N.J., 1981), "Tensid-Taschenbucw', 2 d ed. (Hanser Verlag, Vienna, 1981) and "Encyclopaedia of Surfactants, (Chemical Publishing Co., New York, 1981).

Compounds of the invention and their physiologically acceptable salts (hereafter collectively referred to as the active ingredients) may be administered by any route appropriate to the condition to be treated, suitable routes including oral, rectal, nasal, topical (including ocular, buccal and sublingual), vaginal and parenteral (including subcutaneous, intramuscular, intravenous, intradermal, intrathecal and epidural). The preferred route of administration may vary with for example the condition of the recipient.

While it is possible for the active ingredients to be administered alone it is preferable to present them as pharmaceutical formulations. The formulations, both for veterinary and for human use, of the present invention comprise at least one active ingredient, as above described, together with one or more pharmaceutically acceptable carriers therefore and optionally other therapeutic ingredients. The carrier(s) optimally are "acceptable" in the sense of being compatible with the other ingredients of the formulation and not deleterious to the recipient thereof. The formulations include those suitable for oral, rectal, nasal, topical (including buccal and sublingual), vaginal or parenteral (including subcutaneous, intramuscular, intravenous, intradermal, intrathecal and epidural) administration. The formulations may conveniently be presented in unit dosage form and may be prepared by any of the methods well known in the art of pharmacy. Such methods include the step of bringing into association the active ingredient with the carrier which constitutes one or more accessory ingredients. In general the formulations are prepared by uniformly and intimately bringing into association the active ingredient with liquid carriers or finely divided solid carriers or both, and then, if necessary, shaping the product.

Formulations of the present invention suitable for oral administration may be presented as discrete units such as capsules, cachets or tablets each containing a predetermined amount of the active ingredient; as a powder or granules; as solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, preservative, surface active or dispersing agent. Molded tablets may be made by molding in a suitable machine a mixture of the powdered compound moistened with an inert liquid diluent. The tablets may optionally be coated or scored and may be formulated so as to provide slow or controlled release of the active ingredient therein. For infections of the eye or other external tissues e.g. mouth and skin, the formulations are optionally applied as a topical ointment or cream containing the active ingredient(s) in an amount of, for example, 0.075 to 20% w/w (including active ingredient(s) in a range between 0.1% and 20% in increments of 0.1% w/w such as 0.6% w/w, 0.7% w/w, etc), preferably 0.2 to 15% w/w and most preferably 0.5 to 10% w/w. When formulated in an ointment, the active ingredients may be employed with either a paraffinic or a water-miscible ointment base. Alternatively, the active ingredients may be formulated in a cream with an oil-in-water cream base. If desired, the aqueous phase of the cream base may include, for example, at least 30% w/w of a polyhydric alcohol, i.e. an alcohol having two or more hydroxyl groups such as propylene glycol, butane 1,3-diol, mannitol, sorbitol, glycerol and polyethylene glycol (including PEG400) and mixtures thereof. The topical formulations may desirably include a compound which enhances absorption or penetration of the active ingredient through the skin or other affected areas. Examples of such dermal penetration enhancers include dimethylsulfoxide and related analogs. The oily phase of the emulsions of this invention may be constituted from known ingredients in a known manner. While the phase may comprise merely an emulsifier (otherwise known as an emulgent), it desirably comprises a mixture of at least one emulsifier with a fat or an oil or with both a fat and an oil. Optionally, a hydrophilic emulsifier is included together with a lipophilic emulsifier which acts as a stabilizer. It is also preferred to include both an oil and a fat. Together, the emulsifier(s) with or without stabilizer(s) make up the so-called emulsifying wax, and the wax together with the oil and fat make up the so-called emulsifying ointment base which forms the oily dispersed phase of the cream formulations. The choice of suitable oils or fats for the formulation is based on achieving the desired cosmetic properties, since the solubility of the active compound in most oils likely to be used in pharmaceutical emulsion formulations is very low. Thus the cream should optionally be a non-greasy, non-staining and washable product with suitable consistency to avoid leakage from tubes or other containers. Straight or branched chain, mono- or dibasic alkyl esters such as di-isoadipate, isocetyl stearate, propylene glycol diester of coconut fatty acids, isopropyl myristate, decyl oleate, isopropyl palmitate, butyl stearate, 2-ethylhexyl palmitate or a blend of branched chain esters known as Crodamol CAP may be used, the last three being preferred esters. These may be used alone or in combination depending on the properties required. Alternatively, high melting point lipids such as white soft paraffin and/or liquid paraffin or other mineral oils can be used.

Formulations suitable for topical administration to the eye also include eye drops wherein the active ingredient is dissolved or suspended in a suitable carrier, especially an aqueous solvent for the active ingredient. The active ingredient is optionally present in such formulations in a concentration of 0.5 to 20%, advantageously 0.5 to 10% particularly about 1.5% w/w. Formulations suitable for topical administration in the mouth include lozenges comprising the active ingredient in a flavored basis, usually sucrose and acacia or tragacanth; pastilles comprising the active ingredient in an inert basis such as gelatin and glycerin, or sucrose and acacia; and mouthwashes comprising the active ingredient in a suitable liquid carrier.

Formulations for rectal administration may be presented as a suppository with a suitable base comprising for example cocoa butter or a salicylate. Formulations suitable for nasal administration wherein the carrier is a solid include a coarse powder having a particle size for example in the range 20 to 500 microns (including particle sizes in a range between 20 and 500 microns in increments of 5 microns such as 30 microns, 35 microns, etc), which is administered in the manner in which snuff is taken, i.e. by rapid inhalation through the nasal passage from a container of the powder held close up to the nose. Suitable formulations wherein the carrier is a liquid, for administration as for example a nasal spray or as nasal drops, include aqueous or oily solutions of the active ingredient. Formulations suitable for aerosol administration may be prepared according to conventional methods and may be delivered with other therapeutic agents.

Formulations suitable for vaginal administration may be presented as pessaries, tampons, creams, gels, pastes, foams or spray formulations containing in addition to the active ingredient such carriers as are known in the art to be appropriate.

Formulations suitable for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The formulations may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets of the kind previously described.

Preferred unit dosage formulations are those containing a daily dose or unit daily sub-dose, as herein above recited, or an appropriate fraction thereof, of an active ingredient.

It should be understood that in addition to the ingredients particularly mentioned above the formulations of this invention may include other agents conventional in the art having regard to the type of formulation in question, for example those suitable for oral administration may include flavoring agents.

Compounds of the invention can be used to provide controlled release pharmaceutical formulations containing as active ingredient one or more compounds of the invention ("controlled release formulations") in which the release of the active ingredient can be controlled and regulated to allow less frequency dosing or to improve the pharmacokinetic or toxicity profile of a given invention compound. Controlled release formulations adapted for oral administration in which discrete units comprising one or more compounds of the invention can be prepared according to conventional methods.

Additional ingredients may be included in order to control the duration of action of the active ingredient in the composition. Control release compositions may thus be achieved by selecting appropriate polymer carriers such as for example polyesters, polyamino acids, polyvinyl pyrrolidone, ethylene-vinyl acetate copolymers, methylcellulose, carboxymethylcellulose, protamine sulfate and the like. The rate of drug release and duration of action may also be controlled by incorporating the active ingredient into particles, e.g. microcapsules, of a polymeric substance such as hydrogels, polylactic acid, hydroxymethylcellulose, polymethyl methacrylate and the other above-described polymers. Such methods include colloid drug delivery systems like liposomes, microspheres, microemulsions, nanoparticles, nanocapsules and so on. Depending on the route of administration, the pharmaceutical composition may require protective coatings. Pharmaceutical forms suitable for injectionable use include sterile aqueous solutions or dispersions and sterile powders for the extemporaneous preparation thereof. Typical carriers for this purpose therefore include biocompatible aqueous buffers, ethanol, glycerol, propylene glycol, polyethylene glycol and the like and mixtures thereof.

In view of the fact that, when several active ingredients are used in combination, they do not necessarily bring out their joint therapeutic effect directly at the same time in the mammal to be treated, the corresponding composition may also be in the form of a medical kit or package containing the two ingredients in separate but adjacent repositories or compartments. In the latter context, each active ingredient may therefore be formulated in a way suitable for an administration route different from that of the other ingredient, e.g. one of them may be in the form of an oral or parenteral formulation whereas the other is in the form of an ampoule for intravenous injection or an aerosol.

The survey of biological activity against representative viruses, description of activity on selected animal models in vivo, methods of preparation of the title compound 3 according to the invention as well as of the necessary synthetic intermediates and derivatives are described in the following examples. The compounds according to the formulas of the application like (I) or (II) can be prepared while using a series of chemical reactions known to those skilled in the art, altogether making up the process for preparing said compounds and exemplified further. The following examples are provided for the purpose of illustrating the present invention and by no means are meant and in no way should be interpreted to limit the scope of the present invention.

Example 1

Synthesis of (S)-1-[3-hydroxy-2-(Phosphonomethoxy)propyl]-5-azacytosine (3) with the use of (2S)-2-[(trityloxy]methyl]oxirane (a) Synthesis of (S)-1-[2-Hydroxy-3-(triphenylmethoxy)propyl]-5-azacytosine (1)

A suspension of 5-azacytosine (2 g, 17.8 mmol) and (2S)-2-[(trityloxy]methyl]oxirane (5.63 g, 17.8 mmol) in dry dimethylsulfoxide (20 ml) was heated to 120° C. One pellet of sodium hydroxide (60 mg, 1.5 mmol) was added, the heating under stirring continued till dissolution and then for additional 10 h. The reaction mixture was cooled to room temperature and poured onto a column of neutral alumina (150 ml) equilibrated in toluene. Elution was performed with a mixture of toluene-ethyl acetate (1:1) till the drop of UV absorption followed by ethyl acetate (200 ml) and then a system ethyl acetate-acetone-ethanol-water (18:3:1:1). The purity of product was controlled by TLC in the same system. All product containing fractions (still containing dimethylsulfoxide) were taken down, the residue codistilled with dimethylformamide (2×100 ml) and then with toluene (100 ml). The semisolid residue was crystallized from toluene-acetone (2:1) mixture, the crystalline material was collected by suction, washed with diethyl ether and dried on the air. Yield 6.5 g of 1 (83%), white crystals, m.p. 130-132° C., for $C_{25}H_{24}N_4O_3.0.5H_2O$ (437.5) calculated: 68.63% C, 5.76% H, 12.81% N. Found: 68.82% C, 5.87% H, 12.25% N.

FAB MS, m/z (%): 429 (2) [M+H], 243 (100) [trityl], 113 [5-azacytosine+H].

$^1$H NMR (DMSO-$d_6$): 8.08 s, 1H (H-6); 7.42 m, 6H (H-arom.); 7.40 br s, 1H (NH$_2$); 7.36 m, 6H (H-arom.); 7.30 br s, 1H (NH$_2$); 7.27 m, 3H (H-arom); 4.04 dd, 1H, J (1'a, 2')=3.2, J(gem)=13.4 (H-1'a); 3.92 m, 1H (H-2'); 3.41 dd, 1H, J (1'b, 2')=9.1 (H-1'b); 2.97 dd, 1H, J (3'a, 2')=5.0, J(gem)=9.4 (H-3'a); 2.88 dd, 1H, J (3'b, 2')=5.5 (H-3'b).

$^{13}$C NMR (DMSO-$d_6$): 166.70 (C-4); 159.89 (C-6); 154.26 (C-2); 143.88, 3 C (trityl); 128.43, 6 C (trityl); 128.10, 6 C (trityl); 127.23, 3 C (trityl); 86.07 (O—C); 66.77 (C-2'); 66.15 (C-3'); 50.55 (C-1').

(b) Synthesis of (S)-1-[2-(Diisopropylphosphorylmethoxy)-3-(trityloxy)propyl]-5-azacytosine (2)

Method A. A suspension of 1 (785 mg, 1.8 mmol) in dry dioxane (4 ml) was stirred with sodium tert-butoxide (220 mg, 2.3 mmol). After a complete dissolution of starting material (approx. 15 min) diisopropyl bromomethylphosphonate (700 mg, 2.7 mmol) was added and the mixture heated at 80° C. for 6 h, then cooled to ambient temperature, neutralized dropwise with acetic acid to pH 7 and taken down. The residue was chromatographed on silica gel (300 ml) in the system chloroform-methanol-triethylamine (100:5:1). After elution of a mixture of by-products ($R_F$ 0.40), the desired product ($R_F$ 0.35) was eluted; the rest of unreacted starting compound was eluted with $R_F$ 0.30 (215 mg, 27%). The product containing fractions were evaporated to give 400 mg of 2 (36%) as a white foam, $[\alpha]_D$-36.3 (c 0.715, $CHCl_3$), for $C_{32}H_{39}N_4O_6P$ (606.6) calculated: 63.36% C, 6.50% H, 9.24% N, 5.11% P. Found: 63.18% C, 6.57% H, 9.04% N, 5.32% P, FAB MS, m/z (%): 629 (0.6) [M+Na], 365 (0.2) [M-trityl+2H]; 243 (100) [trityl], $^1$H NMR (DMSO-$d_6$): 8.08 s, 1H (H-6); 7.41 d, 6H (H-arom.); 7.36 br s, 2H ($NH_2$); 7.35 t, 6H and 7.27 t, 3H (H-arom.); 4.54 m, 2H (P—OCH); 3.93 dd, 1H, J (1'a, 2')=3.7, J(gem)=13.8 (H-1'a); 3.85 m, 1H (H-2'); 3.77 d, 1H, J (P, CH)=8.3 ($PCH_a$); 3.75 d, 1H, J (P, CH)=8.4 ($PCH_b$); 3.64 dd, 1H, J (1'b, 2')=9.5 (H-1'b); 3.23 dd, 1H, J (3'a, 2')=3.5, J(gem)=10.6 (H-3'a); 2.92 dd, 1H, J (3'b, 2')=4.4 (H-3'b); 1.22 d, 3H, 1.21 d, 3H, 1.20 d, 3H and 1.17 d, 3H, J ($CH_3$, CH)=6.1 ($CH_3$).

$^{13}$C NMR (DMSO-$d_6$): 166.615 (C-4); 159.665 (C-6); 154.09 (C-2); 143.65, 3 C, 128.47, 6 C, 128.10, 6 C, 127.13, 3 C and 86.36 (trityl); 77.87 d, J (P, C)=12.2 (C-2'); 70.40 d and 70.38 d, J (P, C)=6.4 (P—O—C); 63.97 d, J (P, C)=165.05 (P—C); 63.31 (C-3'); 48.04 (C-1'); 23.93 d, 23.91 d, 23.89 d and 23.77 d, J (P, C)=3.9 ($CH_3$).

Method B. Sodium hydride (60% suspension in mineral oil, 100 mg, 2.5 mmol) was added to a suspension of 1 (830 mg, 2.0 mmon dioxane (5 ml). The mixture was stirred for 30 min at room temperature, then diisopropyl bromomethylphosphonate (674 mg, 2.6 mmol) was added and the reaction mixture stirred at 100° C. for 5 h. After cooling to room temperature, the whole mixture was applied onto a column of silica gel (150 ml) and chromatographed in system chloroform-methanol-triethylamine (100:5:1). After elution of chromatographically faster by-products, the desired phosphonate 2 ($R_F$ 0.35) was obtained in yield 500 mg (41%), followed by regenerated starting compound (250 mg, 30%).

(c) Synthesis of (S)-1-[3-Hydroxy-2-(phosphonomethoxy)propyl]-5-azacytosine (3)

A suspension of the preceding diisopropyl ester 2 (2.27 g, 6.23 mmol) in dry acetonitrile (60 ml) was stirred with bromotrimethylsilane (4.75 ml, 35 mmol) in dark at room temperature for 24 h. The mixture was taken down at 30° C. and the residue coevaporated with acetonitrile (2×100 ml). 0.2M Solution of triethylammonium hydrogencarbonate (100 ml) was added, the resulting solution (pH=7.5) set aside for 10 min and then Dowex 50 (pyridinium form) was added to neutral reaction (pH ≈7.0). The solid was filtered off, a filtrate concentrated to approx. 25 ml and applied onto a column of Dowex 1 (acetate form, 150 ml). Elution was performed with water (1 l), then with a linear gradient of acetic acid (0.5-1 M, 500 ml) and finally, the pure product 3 was eluted with 1 M formic acid. Product containing fractions were taken down, the residue coevaporated with water to a complete removal of formic acid (4×50 ml) and the residue crystallized from water. Crystals were collected by suction, washed with ethanol and ether and dried in vacuo. Yield 930 mg of 3 (53%), m.p. 175-178° C., $[\alpha]_D$-43.7 (c 0.308, $H_2O$).

UV, $\lambda_{max}$: 245 nm (pH 7), 254 nm (pH 2).

For $C_7H_{13}N_4O_6P.H_2O$ (298.2) calculated: 28.20% C, 5.07% H, 18.79% N, 10.39% P. Found: 28.29% C, 4.76% H, 18.55% N, 10.36% P.

FAB MS, m/z (%): 281.1 (4) [M+H]. HR MS (FAB): For $C_7H_{14}N_4O_6P$ [M+H] calculated: 281.0651. Found: 281.0657.

$^1$H NMR ($D_2O$): 8.30 s (H-8); 4.13 dd, 1H, J (1'a, 2')=3.3, J(gem)=14.3 (H-1'a); 3.835 dd, 1H, J (1'b, 2')=8.1 (H-1'b); 3.85 dd, 1H, J (3'a, 2')=3.7, J(gem)=12.6 (H-3'a); 3.76 dd, 1H, J (P, CH)=9.3, J(gem)=12.9 ($PCH_a$); 3.74 m, 1H (H-2'); 3.62 dd, 1H, J (3'b, 2')=4.2 (H-3'b); 3.56 dd, 1H, J (P, CH)=9.8, J(gem)=12.9 ($PCH_b$).

$^{13}$C NMR ($D_2O$): 166.20 (C-4); 160.77 (C-6); 156.64 (C-2); 79.18 d, J (P, C)=12.2 (C-2'); 66.36 d, J (P, C)=156.25 (P—C); 48.24 (C-1').

Example 2

Synthesis of (S)-1-[3-hydroxy-2-(phosphonomethoxy)propyl]-5-azacytosine (3) with the use of the HPMP-synthon (8)

(a) Synthesis of (R)-1-O-Benzyl-3-O-tritylglycerol (4)

Trityl chloride (56 g) was added portionswise to a solution of 1-O-benzyl-(R)-glycerol (36.4 g, 0.2 mol) and 4-diethylaminopyridine (1 g) in pyridine (300 mL) under stirring and cooling with ice. After 20 h stirring methanol (50 mL) was added, the mixture was stirred for 30 min and concentrated in vacuo to half of the original volume. Ethyl acetate (500 mL) was added and the mixture extracted with water (3×250 mL). The organic layer was briefly dried with MgSO4, filtered and evaporated in vacuo. The residue 4 was codistilled with toluene (200 ml portions) to remove the residual pyridine and used for further synthesis.

(b) Synthesis of (R)-1-O-Benzyl-2-(diisopropylphosphorylmethyl)-3-O-tritylglycerol (5)

Method A. Sodium hydride (3.0 g, 128 mmol) was added to the solution of 4 (49.2 g, 0.112 mol) in dry tetrahydrofuran (120 mL) and the suspension stirred for 20 min at rt and refluxed for 1 h. The mixture was cooled down and diisopropyl p-tolylsulfonyloxymethylphosphonate (45 g) was added in one portion. The mixture was stirred at rt for three days and neutralized by acetic acid. Methanol (100 mL) was added and the solvents were taken down in vacuo. The residue in ethyl acetate (800 mL) was washed with water (3×200 mL), dried and evaporated in vacuo. The chromatographically pure residue 5 (70 g) was used for further steps.

Method B. Sodium hydride (1.8 g, 75 mmol) was added to the solution of 4 (20 g, 47 mmol) in dry dimethylformamide (200 mL). After 30 min stirring at rt diisopropyl bromomethylphosphonate (16 g, 62 mmol) was added to the reaction mixture which was then heated 90 min at 60° C. Further workup was identical with that described in Method A. Yield of 5 was 31 g.

(c) Synthesis of (R)-1-O-Benzyl-2-(diisopropylphosphorylmethyl)glycerol (6)

Compound 5 (31 g) was stirred 4 h with a mixture of dioxane (250 mL) and 1 M HCl (250 mL) till the starting material disappeared (approx. 3 h). Ethyl acetate (500 mL) was added, and the aqueous phase after extraction washed twice more with ethyl acetate (250 mL each). The combined extracts were washed with saturated $NaHCO_3$ solution (2×300 mL) dried with $MgSO_4$ and evaporated in vacuo to give the chromatographically pure material 6 which was directly used for further steps.

(d) Synthesis of (2S)-2-[(Diisopropylphosphoryl)methoxy]-3-benzyloxy-propyl p-tolylsulfonate (7)

p-Tolylsulfonyl chloride (38.8 g, 204 mmol) was added to a solution of compound 6 (31 g) in dry pyridine (200 mL) cooled to 0° C. After 1 h stirring at 0° C. the mixture was stirred at room temperature (rt) for additional 24 h and evaporated in vacuo. The syrupy residue was chromatographed on a column of silica gel (1000 mL) in system toluene-ethyl acetate (5:1). After removal of rests of p-tolylsulfonyl chloride ($R_F$ 0.9) the compound 7 was eluted with system toluene-ethyl acetate (1:2), ($R_F$ 0.5). Product containing fractions were evaporated to give 18.7 g (77%) of 7 as a colorless syrup.

$^1$H NMR (DMSO-$d_6$): 7.79 d, 2H, 7.47 d, 2H and 7.35-7.20 m, 5H (H-arom.); 4.56 m, 2H (P—OCH); 4.46 m, 1H (OCH); 4.17 dd, 1H, J ($CH_a$, CH)=3.2, J(gem)=10.6 and 4.03 dd, 1H, J ($CH_b$, CH)=5.4 ($OCH_2$); 3.83 dd, 1H, J (P, $CH_a$)=9.1, J(gem)=13.8 ($PCH_a$); 3.77 dd, 1H, J (P, $CH_b$)=8.8 ($PCH_b$); 3.50 dd, 1H, J ($CH_a$, CH)=5.1, J(gem)=10.4 and 3.47 dd, 1H, J ($CH_b$, CH)=5.4 ($OCH_2$); 2.40 s, 3H ($CH_3$); 1.22 d, 3H, 1.21 d, 3H, 1.19 d, 3H and 1.185 d, 3H, J ($CH_3$, CH)=6.1 ($CH_3$).

$^{13}$C NMR (DMSO-$d_6$): 145.17 (tosyl); 138.175 (benzyl); 132.18 and 130.34, 2 C (tosyl); 128.32, 2 C, 127.82, 2C and 127.67 (benzyl); 127.53, 2 C (tosyl); 77.42 d, J (P, C)=12.2 (OCH); 72.48 ($OCH_2$); 70.43 d and 70.41 d, J (P, C)=6.3 (P—OCH); 69.22 and 67.89 ($OCH_2$); 63.94 d, J (P, C)=165.0 (P—C); 23.96, 2C, J (P, C)=3.9 ($CH_3$); 23.79 d, 2 C, J (P, C)=4.4 ($CH_3$); 21.25 ($CH_3$).

(e) Synthesis of (2S)-2-[(Diisopropylphosphoryl)methoxy]-3-hydroxypropyl p-tolylsulfonate (8)

10% Palladium on carbon (1.05 g) was added to a solution of 7 (11.5 g, 22.4 mmol) in methanol (150 ml) and the mixture was hydrogenated at room temperature under atmospheric pressure for 24 h. The solid was filtered off through Celite, washed with methanol (2×100 ml) and combined filtrates were concentrated in vacuo. The syrupy residue was chromatographed on a column of silica gel (400 ml) in ethyl acetate. Product containing fractions were evaporated to give 7.7 g (81%) of compound 8 as a colorless syrup, $[\alpha]_D$+21.4 (c 0.337, $CHCl_3$).

For $C_{17}H_{29}O_8SP$ (424.5) calculated: 48.11% C, 6.89% H, 7.55% S, 7.30% P. Found: 47.71% C, 6.99% H, 7.80% S, 7.48% P.

FAB MS, m/z (%): 425 (39) [M+H].

$^1$H NMR (DMSO-$d_6$): 7.79 d, 2H and 7.49 d, 2H (H-arom.); 4.82 t, 1H, J (OH, $CH_2$)=5.5 (OH); 4.56 m, 2H (P—OCH); 4.15 dd, 1H, J ($CH_2$, CH)=3.1, J(gem)=10.6 and 3.98 dd, 1H, J ($CH_2$, CH)=6.0, J(gem)=10.6 ($OCH_2$); 3.81 dd, 1H and 3.71 dd, 1H, J (P, CH)=8.8, J(gem)=13.9 ($PCH_2$); 3.62 m, 1H (OCH); 3.45 dt, 1H, J ($CH_2$, OH)=J ($CH_2$, CH)=5.0, J(gem)=11.2 and 3.37 dt, 1H, J ($CH_2$, OH)=J ($CH_2$, CH)=6.0, J(gem)=11.2 ($OCH_2$); 2.42 s, 3H ($CH_3$); 1.225 d, 6H, 1.205 d, 3H and 1.20 d, 3H, J ($CH_3$, CH)=6.2 ($CH_3$).

$^{13}$C NMR (DMSO-$d_6$): 145.12, 132.32, 130.34, 2 C and 127.80, 2 C (arom.); 79.28 d, J (P, C)=11.2 (OCH); 70.41 d and 70.39 d, J (P, C)=6.3 (P—OCH); 69.73 and 59.13 ($OCH_2$); 23.97 d, J (P, C)=4.4 and 23.81 d, J (P, C)=4.4 ($CH_3$); 21.26 ($CH_3$).

(f) Synthesis of diisopropyl(S)-1-[3-Hydroxy-2-(phosphonomethoxy)propyl]-5-azacytosine (9)

A mixture of a sodium salt of 5-azacytosine (1.34 g, 10 mmol) and the tosylate synthon 8 (4.2 g, 9.9 mmol) in dimethylformamide (30 ml) was heated to 90° C. with exclusion of moisture for 5 h. Additional portion of the tosylate (1.2 g, 2.8 mmol) was added together with a catalytic amount of cesium carbonate (10 mg) and the heating continued at 120° C. for 2 h. During that time, a complete dissolution occurred. The reaction mixture was taken down, the residue coevaporated with toluene (2×50 ml) and xylene (50 ml) and applied onto a column of silica gel (400 ml) in system chloroform-methanol (95:5). The column was eluted first with this system, after elution of approx. 1.5 l volume, the polarity of system was increased to the ratio chloroform-methanol (85:15). The elution afforded the main reaction product with $R_F$ 0.33 (system chloroform-methanol 85:15). The product containing fractions were taken down and coevaporated with absolute ethanol. Yield of the diisopropyl ester 9 was 2.4 g (62%): colourless oil which crystallized on standing, $[\alpha]_D$–43.0 (c 0.49, ethanol).

For $C_{13}H_{25}N_4O_6P$. ½$C_2H_5OH$ (387.4) calculated: 43.40% C, 7.29% H, 14.46% N, 8.00% P. Found: 43.58% C, 6.99% H, 14.45% N, 8.22% P.

FAB MS, m/z (%): 365 (100) [M+H], 281 (70) [free phosphonic acid+H], 113 (84) [5-azacytosine+H].

$^1$H NMR (DMSO-$d_6$): 8.06 s, 1H (H-6); 7.38 br s, 2H ($NH_2$); 4.83 t, 1H, J (OH, 3')=5.5 (OH); 4.54 m, 2H (P—OCH); 3.96 dd, 1H, J (1'a, 2')=2.4, J(gem)=14.1 (H-1'a); 3.89 dd, 1H, J (1'b, 2')=8.1, J (gem)=14.1 (H-1'b); 3.70 dd, 1H, J (P, $CH_a$)=9.4, J(gem)=14.0 ($PCH_a$); 3.63 m, 1H (H-2'); 3.59 dd, 1H J (P, $CH_b$)=8.2, J(gem)=14.0 ($PCH_b$); 3.51 tt, 1H, J (3'a, OH)=J (3'a, 2')=4.8, J(gem)=12.0 (H-3'a); 3.45 ddd, 1H, J (3'b, 2')=4.4, J (3'b, OH)=5.8, J(gem)=12.0 (H-3'b); 1.23 d, 3H, 1.22 d, 3H, 1.21 d, 3H and 1.19 d, 3H, J ($CH_3$, CH)=6.2.

Proton-coupled $^{13}$C NMR (DMSO-$d_6$): 166.63 d, J (C-4, H-6)=12.7 (C-4); 159.785 dt, $^1$J=204.1, J (C-6, H-1'a)=J (C-6, H-1'b)=3.9 (C-6); 154.29 dt, J (C-2, H-6)=4.9, J (C-2, H-1'a)=J (C-2, H-1'b)=2.9 (C-2); 79.28 d, J (P, C)=10.7 (C-2'); 70.33 d, 2 C, J (P, C)=6.4 (P—O—C); 63.61 d, J (P, C)=165.0 (P—C); 60.34 (C-3'); 47.70 (C-1'); 23.95 d and 23.91 d, J (P, C)=4.9 ($CH_3$); 23.87 d and 23.78 d, J (P, C)=4.4 ($CH_3$).

(g) Synthesis of (S)-1-[3-hydroxy-2-(phosphonomethoxy)propyl]-5-azacytosine (3)

Bromotrimethylsilane (4.7 ml, 35 mmol) was added to a solution of 9 (1.34 g, 3.13 mmol) in acetonitrile (30 ml) and the mixture was set aside at ambient temperature for 20 h. The mixture was evaporated at 30° C., the residue coevaporated with acetonitrile (2×30 ml) and 90% aqueous methanol (50 ml) was added. The solution was neutralized with 1 M triethylammonium hydrogencarbonate to pH 7 and evaporated. The residue was partitioned between water (100 ml) and ether (100 ml), an aqueous layer evaporated to a volume 5 ml and applied onto a column of Dowex 1 ($AcO^-$ form, 100 ml). Elution was performed with water (500 ml), then with a linear gradient of acetic acid (0.1-1 M, 1.5 l) and finally, the product was eluted with 1 M formic acid. UV absorbing fractions were taken down in vacuo and the residue coevaporated with water (4×20 ml). The residue was crystallized from water.

Yield 350 mg (37%) of compound 3, identical with the product described in Example 1. M.p. 175-178° C.,

Example 3

Equilibrium with Sodium 3-formyl-2-{[(2S)-3-hydroxy-2-(phosphono-methoxy)propyl]carbamoyl}guanidine (3a)

A solution of compound 3 (100 mg, 0.34 mmol) in 0.25 M triethylammonium hydrogencarbonate (5 ml) was incubated at 37° C. for 72 h and then 12 h at 80° C. The reaction course was monitored by measurement of absorption maximum decrease in UV spectrum at $\lambda_{max}$ 245 nm. For each measurement 10 µl sample of reaction mixture was diluted with water to overall volume 3 ml and absorbance value at 245 nm determined. Equilibrium was reached when no more decrease of absorbance occurred. The reaction mixture was evaporated to dryness, coevaporated with water (5×3 ml) and then with methanol (2×3 ml). The residue in water (3 ml) was applied onto a column of Dowex 50 ($Na^+$ form, 20 ml) and the column eluted with water. UV absorbing eluate was evaporated and lyophilized to give 105 mg (92%) of a sodium salt of 3a as a colourless amorphous material.

$^1$H NMR ($D_2O$): 8.46 s, 1H (CH=O). $^{13}$C NMR ($D_2O$): 171.04 (CH=O); 155.29 and 154.64 (C-2, C-4); 80.33 d, J (C, P)=10.7 (C-2'); 66.72 d, J (C, P)=153.8 ($PCH_2$); 60.76 (C-3'); 39.96 (C-1').

Example 4

Decomposition into 2-{[(2S)-3-Hydroxy-2-(Phosphonomethoxy)propyl]carbamoyl}guanidine (10)

A solution of compound 3 (200 mg, 0.67 mmol) in 1 M aqueous ammonia (2.5 ml) was stirred at room temperature for 48 h, then evaporated in vacuo and coevaporated with water (5 ml). The crude product was purified by reverse phase HPLC, elution with water. The desired product (not absorbing in UV) was detected by TLC on silica gel plates in system isopropanol-25% $NH_4OH$-water 7:1:2 followed by spraying the plate with a mixture 5% NaOH-5% $K_3[Fe(CN)_6]$-5% $Na[Fe(CN)_5NO]$ (1:1:1) giving orange spots of product. The product containing fractions were evaporated and dried in vacuo. Yield 150 mg (83%) of 10, white foam, $[\alpha]_D$+31.2 (c 0.226, $H_2O$).

FAB MS, m/z (%): 271 (100) [M+H]. HR MS (FAB): For $C_6H_{16}N_4O_6P$ [M+H] calculated: 271.0807. Found: 271.0808.

$^1$H NMR ($D_2O$): 3.75 dd, 1H, J=3.2 and 11.2 (H-3'a); 3.73 dd, 1H, J=9.0 and 12.7 ($PCH_a$); 3.63 dd, 1H, J=9.4 and 12.7 ($PCH_b$); 3.61 m, 1H (H-2'); 3.59 dd, 1H, J=5.1 and 11.2 (H-3'b); 3.47 dd, 1H, J=3.2 and 14.3 (H-1'a); 3.29 dd, 1H, J=7.3 and 14.3 (H-1'b).

$^{13}$C NMR ($D_2O$): 155.25 and 154.60 (C-2, C-4); 80.25 d, J (P, C)=11.2 (C-2'); 66.78 d, J (P, C)=152.8 ($PCH_2$); 60.68 (C-3'); 40.01 (C-1').

Example 5

Synthesis of 1-{[(5S)-2-Hydroxy-2-oxido-1,4,2-dioxaphosphinan-5-yl]methyl}-5-azacytosine ("cyclic HPMP-5-azacytosine"-"cHPMP-5-azaC"-11)

A suspension of starting HPMP-5-azacytosine (200 mg, 0.71 mmol), N,N'-dicyclohexylcarbodiimide (DCC, 155 mg, 0.75 mmol) and N,N'-dicyclohexyl-4-morpholinecarboxamidine (220 mg, 0.75 mmol) in DMF (5 ml) was stirred at 85° C. for 3 h, then additional portions of DCC (20 mg) and N,N'-dicyclohexyl-4-morpholinecarboxamidine (20 mg) were added and the heating continued for 2 h (till conversion was complete). The reaction course was monitored by TLC in system 2-propanol-25% aqueous ammonia-water (7:1:2), $R_F$ of the product: 0.45. The reaction mixture was cooled to room temperature, diluted with water (5 ml) and applied onto a column of Dowex 1 (acetate form, 50 ml). Elution was performed with water (500 ml), followed by 1 M acetic acid (200 ml) and finally, the product was eluted with 1 M formic acid. A product containing fraction was evaporated, the residue coevaporated with water (4×30 ml). The crude product was finally purified by reverse phase HPLC: preparative column 21×250 mm (Luna Phenomenex® C-18), isocratic elution with 2% aqueous methanol (12 ml/min), retention time: 10 min. The product containing fraction was evaporated and dried in vacuo. Yield: 180 mg (97%), white solid.

$[\alpha]_D$-46.6 (c 0.172, $H_2O$).

ESI MS: 263 $[M+H]^+$ (70), 525 $[2M+H]^+$ (100).

HR MS (Q TOF): For $C_7H_{12}N_4O_5P$ [M+H] calculated: 263.0545. Found: 263.0543.

$^1$H NMR ($D_2O$): 8.46 s, 1H (H-6); 4.25 m, 2H (H-3'); 4.18 dd, 1H, J (1'a, 2')=2.9, J(gem)=14.6 (H-1'a); 4.02 m, 1H (H-2'); 3.97 dd, 1H, J (P, $CH_a$)=9.3, J(gem)=14.2 ($PCH_a$); 3.86 dd, 1H, J (1'b, 2')=8.3 (H-1'b); 3.83 dd, 1H, J (P, $CH_b$)= 1.7 ($PCH_b$).

$^{13}$C NMR ($D_2O$): 162.30 (C-6); 159.52 (C-4); 147.41 (C-2); 72.83 d, J (P, C)=4.4 (C-2'); 69.48 d, J (P, C)=6.8 (C-3'); 65.12 d, J (P, C)=143.6 (P—C); 46.57 (C-1').

Example 6

Synthesis of hexadecyloxyethyl ester of 1-{[(5S)-2-Hydroxy-2-oxido-1,4,2-dioxaphosphinan-5-yl]methyl}-5-azacytosine (12)

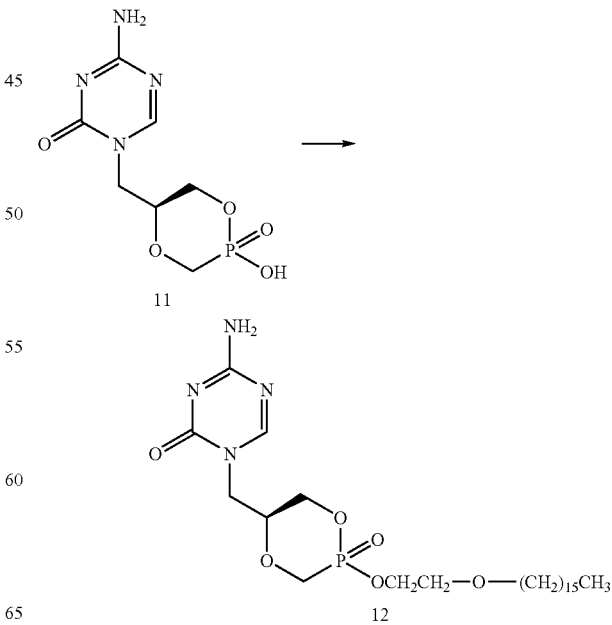

A suspension of starting 1-{[(5S)-2-Hydroxy-2-oxido-1,4,2-dioxaphosphinan-5-yl]methyl}-5-azacytosine (i.e. cyclic HPMP-5-azacytosine, 230 mg, 0.87 mmol), hexadecyloxyethanol (260 mg, 0.9 mmol), DCC (300 mg, 1.5 mmol) and dimethylaminopyridine (5 mg) in dry DMF (5 ml) was stirred at 110° C. for 20 h. After cooling to room temperature, the mixture was diluted with water (10 ml) and applied onto a column of Dowex 1 (AcO⁻ form, 25 ml). The column was eluted with acetone (200 ml), followed by water (200 ml). The combined UV absorbing elutes were evaporated and the residue chromatographed on preparative silica gel plate (12×25 cm) in system chloroform-methanol (85:15). Yield: 30 mg (6.5%), white solid. The product was obtained as a mixture of two diastereoisomers (ratio 3:2).

¹H NMR (CDCl₃): Diastereoisomer A (major component): 7.93 s, 1H (H-6); 6.82 brs, 1H and 5.80 brs, 1H (NH); 4.42-3.37 m, 13H (H-1', H-2', H-3', PCH₂, OCH₂); 1.96 m, 4H, 1.54 m, 2H and 1.25 m, 22H (CH₂); 0.88 t, 3H, J (CH₃, CH₂)=7.1 (CH₃). Diastereoisomer B (minor): 7.96 s, 1H (H-6); 6.69 brs, 1H and 5.87 brs, 1H (NH); other signals identical.

¹³C NMR (CDCl₃): Diastereoisomer A (major component): 166.40 (C-4); 159.10 (C-6); 154.11 (C-2); 73.27 d, J (P,C)=5.4 (C-2'); 71.64 d, J (P, C)=8.3 (C-3'); 71.24, 66.31 and 64.63 d, J (P, C)=7.3 (OCH₂); 63.57 d, J (P, C)=145.0 (P—C); 46.73 (C-1'); 31.95, 30.78, 30.74, 29.64, 8 C, 29.33, 26.16 and 22.66 (CH₂); 14.10 (CH₃). Diastereoisomer B (minor): 166.40 (C-4); 159.10 (C-6); 154.04 (C-2); 72.96 d, J (P, C)=3.9 (C-2'); 71.22 (OCH₂); 70.33 d, J (P, C)=6.8 (C-3'); 66.14 (OCH₂); 63.57 d, J (P, C)=145.0 (P—C); 63.40 d, J (P, C)=5.9 (OCH₂); 46.89 (C-1'); 31.89, 30.88, 30.84, 29.64, 8 C, 29.60, 26.11 and 22.66 (CH₂); 14.10 (CH₃).

The unreacted starting cyclic HPMP-5-azacytosine can be recovered from Dowex 1. The column was eluted first with 1 M acetic acid (250 ml) to remove some impurities and degradation products. The pure cyclic phosphonate was eluted with 1 M formic acid, appropriate fractions were evaporated, coevaporated with water (4×30 ml) and with absolute ethanol (50 ml) and dried in vacuo to give 150 mg (65%) of cyclic HPMP-5-azacytosine.

Example 7

Synthesis of pivaloyloxymethyl ester of 1-{[(5S)-2-Hydroxy-2-oxido-1,4,2-dioxaphosphinan-5-yl]methyl}-5-azacytosine (cyclic POM-HPMP-azaC-13) and of Bis(pivaloyloxymethyl) ester of 1-(S)-[3-hydroxy-2-(phosphonomethoxy)propyl]-5-azacytosine (Bis(POM)-HPMP-azaC-14).

Scheme 8

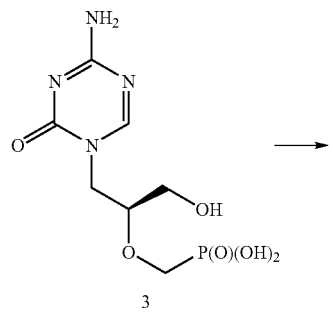

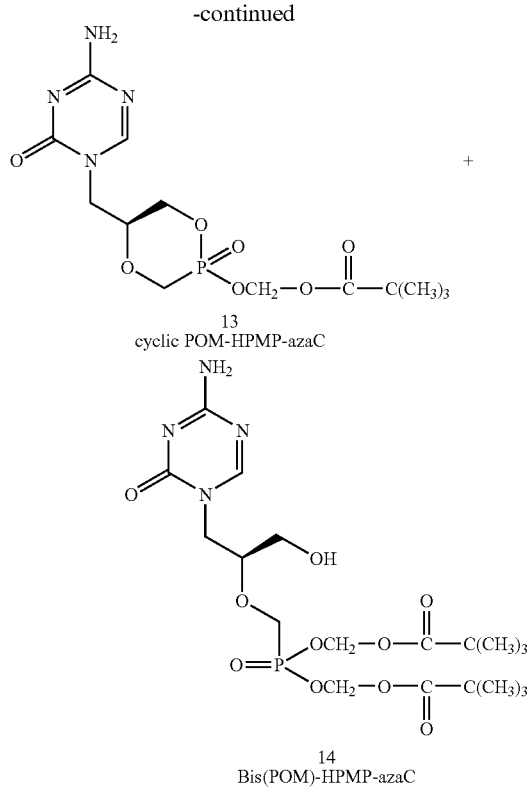

13
cyclic POM-HPMP-azaC

14
Bis(POM)-HPMP-azaC

A suspension of starting 1-(S)-[3-hydroxy-2-(phosphonomethoxy)propyl]-5-aza-cytosine 3 (100 mg; 0.36 mmol) in dry DMF (4 ml) was evaporated to/2 of its original volume. N,N'-dicyclohexyl-4-morpholinecarboxamidine (200 mg, 0.68 mmol) followed by chloromethyl pivalate (275 mg; 1.83 mmol) were added and the mixture was stirred for 72 h at 25° C. The mixture was evaporated, the residue coevaporated with xylene (4 ml) and chromatographed on preparative TLC silica gel plate (40×17 cm) in system ethyl acetate-acetone-ethanol-water (15:3:4:3). An appropriate band of silica gel ($R_F$ 0.75) was separated, eluted with methanol and filtered through Celite pad followed by filtration through nylon membrane filter (Whatman® 0.2 μm). The filtrate was evaporated to give 38 mg of a mixture of POM esters as a white foam.

FAB MS, m/z (%): 509 (0.5) [M+H of bis(POM)-HPMP-azaC], 377 (1) [M+H of cyclic POM-HPMP-azaC], 294.2 (80) [M-pivaloyl+2H, cyclic phosphonate], 86 (10) [pivaloyl].

HR MS (FAB, cyclic POM-HPMP-azaC): For $C_{13}H_{22}N_4O_7P$ [M+H] calculated: 377.1226. Found: 377.1218. HR MS (FAB, bis(POM)-HPMP-azaC): For $C_{19}H_{34}N_4O_{10}P$ [M+H] calculated: 509.2012. Found: 509.2004.

Example 8

Methods for In Vitro Determination of Antiviral Activity

Cells

Human embryonic lung (HEL) fibroblasts (ATCC CCL137) or E₆SM (human diploid fibroblasts) were used at low passages (10 to 17). They were maintained in minimum essential medium (MEM) supplemented with 10% heat-inactivated fetal calf serum (FCS), 1% L-glutamine and 0.3% sodium bicarbonate.

HeLa cells were used. They were maintained in minimum essential medium (MEM) supplemented with 10% heat-inactivated fetal calf serum (FCS), 1% L-glutamine and 0.3% sodium bicarbonate.

Vero cells were used. They were maintained in minimum essential medium (MEM) supplemented with 10% heat-inactivated fetal calf serum (FCS), 1% L-glutamine and 0.3% sodium bicarbonate.

Primary human keratinocytes (PHKs) were isolated from neonatal foreskins. Tissue fragments were incubated with trypsin-EDTA for 1 h at 37° C. The epithelial cells were detached and cultured with Serum-Free Keratinocyte Medium (Gibco, Invitrogen Corporation, UK) supplemented with 0.5 µg/ml hydrocortisone, 10 ng/ml epidermal growth factor, 10% fetal calf serum, 2 mmol/liter L-glutamine, 10 mmol/liter HEPES, 1 mmol/liter sodium pyruvate, $10^{-10}$ mol/liter cholera toxin, 5 µg:ml insulin, 5 µg/ml transferrine and $15 \times 10^{-4}$ mg/ml 3,3',5'-triiodo-L-thyronine.

Primary lamb keratinocytes (PLKs) were isolated from foreskin tissue of 3 to 12 month old lambs. Thin sheets of foreskin tissue were cut in small pieces and then incubated with trypsin-EDTA (Gibco, Invitrogen Corporation, UK) for 30 minutes at 37° C. Trypsinized cells were filtered and then centrifuged for 10 minutes at 1200 rpm. The cell pellet was resuspended in the growth medium (a mixture of Ham's F12 and Dulbecco's modified Eagle's medium (1:4), supplemented with 0.5 µg/ml hydrocortisone, 10 ng/ml epidermal growth factor, 10% fetal calf serum, 2 mmol/liter L-glutamine, 10 mmol/liter HEPES, 1 mmol/liter sodium pyruvate, 10-10 mol/liter cholera toxin, 5 µg:ml insulin, 5 µg/ml transferring, and 15×10-4 mg/ml 3,3',5'-triiodo-L-thyronine.

UC1-B and BS-C-1 cells: UC1-B cells (murine embryo fibroblasts, ATCC 6465-CRL) and BS-C-1 cells (African green monkey kidney cell line, ATCC CCL-26) were maintained in minimum essential medium (MEM) supplemented with 10% heat-inactivated fetal calf serum (FCS), 1% L-glutamine and 0.3% sodium bicarbonate.

Primary human keratinocytes: Primary human keratinocytes (PHKs) were isolated from neonatal foreskins. Tissue fragments were incubated with trypsin-EDTA for 1 h at 37° C. The epithelial cells were detached and cultured with Serum-Free Keratinocyte Medium (Gibco, Invitrogen Corporation, UK) supplemented with 0.5 µg/ml hydrocortisone, 10 ng/ml epidermal growth factor, 10% fetal calf serum, 2 mmol/liter L-glutamine, 10 mmol/liter HEPES, 1 mmol/liter sodium pyruvate, 10-10 mol/liter cholera toxin, 5 µg/ml insulin, 5 µg/ml transferring, and 15×10-4 mg/ml 3,3',5'-triiodo-L-thyronine.

Also other cell types were used in the experiments such as described herein, namely human T-lymphoblast HSB-2 and MOLT-3 cells.

Viruses

The Human Cytomegalovirus (HCMV) reference strains AD-169 (ATCC VR538) and Davis (ATCC VR 807) were used. Virus stocks were prepared as described previously. Virus stocks were prepared in HEL cells. When 100% cytopathogenic effect was obtained, the cells and supernatant were frozen. After one cycle freezing/thawing, the cell debris were removed by centrifugation and the supernatant stored in aliquots at −80° C.

The Varicella-Zoster Virus (VZV) reference strains Oka (ATCC VR-795) and YS were used as well as the thymidine kinase (TK)-deficient strains YS-R and 07-1. Virus stocks were prepared as described previously (Andrei G. et al., Eur. J. Clin. Microbiol. Infect. Dis. 1995, 14 (4), 318-329). Virus stocks were prepared in HEL cells. When 70% cytopathogenic effect was obtained, the cells were trypsinized and resuspended in medium containing 10% DMSO and stored in aliquots at −80° C.

The Herpes simplex virus (HSV) reference strains KOS (ATCC VR-1493), F (ATCC VR-733), McIntyre (ATCC VR-539), G (ATCC VR-734), 196, Lyons were used as well as the thymidine kinase (TK)-deficient strain KOS ACV$^r$.

Virus stocks were prepared as described previously. Virus stocks were prepared in E$_6$SM cells. When 100% cytopathogenic effect was obtained, the cells and supernatant were frozen. After one cycle freezing/thawing, the cell debris were removed by centrifugation and the supernatant stored in aliquots at −80° C.

Also human herpesvirus 6 strains were used, namely HHV-6A (strain GS) and HHV-6B (strain Z29).

Human adenovirus type 2: Ad2 as clinical isolate was used on HEL cells.

For the orthopoxviruses, the vaccinia virus strains Lederle chorioallantoic (ATCC CCL-137), Western Reserve (ATCC VR-119), Lister (VR-1549, Elstree), Copenhagen strain and the Cowpox virus strain Brighton (ATCC VR-302) were used. For the parapoxviruses, the orf virus strain NZ 2 (ATCC VR-1548) was used. Virus stocks were prepared as described previously. Virus stocks were prepared in HEL cells. When 100% cytopathogenic effect was obtained, the cells and supernatant were frozen. After one cycle freezing/thawing, the cell debris were removed by centrifugation and the supernatant stored in aliquots at −80° C. Also recombinant virus strains resistant against HPMPC were used to test the activity of the compounds of the present invention. These recombinant virus strains were prepared as known in the art.

Vesicular stomatitis virus, Coxsakie virus B4, parainfluenza-3 virus, respiratory syncytial virus, Reovirus-1, Sindbis virus and Punta Toro virus were taken as representative for the respective following families of viruses: rhabdoviruses, enteroviruses, paramyxoviruses (pneumovivuses/RSV), reoviruses, togaviruses and bunyaviruses. Virus stocks were prepared as described previously. Virus stocks were prepared in the appropriated cell line for each virus. When 100% cytopathogenic effect was obtained, the cells and supernatant were frozen. After one cycle freezing/thawing, the cell debris were removed by centrifugation and the supernatant stored in aliquots at −80° C.

Polyomavirus: Four murine polyomavirus strains [MN/RDE Toronto, PTA, 2PTA2, and LID-1] and three simian polyomavirus strains [SV40 (a vacuolating agent) strain A2895, SV40 PML-1 strain EK, and SV40 PML-2 strain DAR] were used. The polyomavirus strains and the SV40 strains were propagated and assessed in UC1-B and BS-C-1 cells, respectively.

Moluscum contagiosum virus (MCV): Fresh lesions obtained from preadolescent children were used to recover the clinical samples of molluscum contagiosum virus.

Antiviral Assays for VZV and HCMV in HEL Cells.

VZV- and HCMV-drug susceptibility assays were performed as previously described (Andrei G., et al, Eur. J. Clin. Microbiol. Infect. Dis. 1991, 10 (12), 1026-1033). Confluent HEL cells in 96-well microtiter plates were infected with 20 pfu of cell-associated virus per well (VZV) or 100 pfu of cell-free virus (HCMV). After 2 hours incubation, the inoculum was removed and replaced by the different dilutions (in duplicate) of the tested molecules. After 5 (VZV) or 7 (HCMV) days of incubation the cells were fixed and stained with Giemsa. The activity was determined by counting the number of plaques (VZV) or evaluating the CPE (HCMV) for each dilution. The activity is expressed as $EC_{50}$ or effective compound concentration required to reduce virus-induced cytopathicity (CPE) by 50%, as compared to the untreated control.

Antiviral Assays for HSV, VSV, Coxsackie, RSV, Para-Influenza-3, Reovirus, and Punta Toro Virus.

Confluent $E_6SM$ cells (HSV and VSV), HeLa cells (VSV, Coxsackie and RSV), Vero cells (Para-influenza, Reovirus, Sindbis, and Punta Toro viruses) grown in 96-well microtiter plates were infected with 100 $CCID_{50}$ of cell free viruses. After 1 hour incubation, (2 hours for RSV), the inoculum was removed and replaced by the different dilutions (in duplicate) of the tested molecules. After 2 to 3 days incubation the CPE was evaluated under the microscope. The activity is expressed as $EC_{50}$ or effective compound concentration required to reduce virus-induced cytopathicity (CPE) by 50%, as compared to the untreated control.

More specifically for anti-Coxsackie virus assay: Ninety-six-well cell culture plates can be seeded with Vero cells in DMEM medium containing 10 fetal calf serum (FCS) so that cells reach confluency 24-48 hr later. Medium can then be removed and serial 5-fold dilutions of the test compounds can be added in a total volume of 100 ul, after which the virus inoculum (100 µl) can be added to each well. The virus inoculum used results normally in a 90-100% destruction of the cell monolayer after 5 days incubation at 37° C. Uninfected cells and cells receiving virus without compound can be included in each assay plate. After 5 days, the medium can be removed and 90 µl of DMEM-FCS and 10 µl of MTS/PMS solution (Promega) was added to each well. Following a 2 h incubation period at 37° C., the optical density of the wells can be read at 498 nm in a microplate reader. The 50% effective concentration ($EC_{50}$) value can than be defined as the concentration of compound that protects 50% of the cell monolayer from the virus-induced cytopathic effect.

Antiviral Assay for Human Adenovirus Type 2

Human embryonic lung (HEL) fibroblast cells were seeded in 96-well plates at 10000 cells per well and incubated for 4-5 days until confluency. To each well, 50 µl of Ad2 (a clinical isolate of adenovirus type 2) was added, diluted in medium to obtain a virus input of 5 PFU per well. After 2 hr at 37° C., virus was aspirated and replaced by serial dilutions of the test compounds (200 µl per well). Mock-treated cultures receiving only the test compounds were included in each plate. After 10-12 days incubation at 37° C., microscopy was performed to score the virus-induced cytopathic effect (CPE), and compound toxicity, expressed as the Minimum Cytotoxic Concentration. The plates were then subjected to the MTS-based calorimetric assay for cell viability according to the Manufacturer's instructions (Promega, Leiden, The Netherlands). The A490 nm values, corrected for cytotoxicity exerted by the test compounds (as determined in mock-infected cultures), were used to calculate the percent cell viability. The 50% effective concentration ($EC_{50}$) was determined by extrapolation and defined as the compound concentration that produced 50% protection against the virus. (Naesens et al., Antimicrob. Agents Chemother. (2005), 49: 1010-1016).

Antiviral Assays for Human Herpesvirus 6

HHV-6 assays were performed in human T-lymphoblast HSB-2 (for HHV-6A, strain GS) and MOLT-3 (for HHV-6B, strain Z29) cells. Virus stocks were added to concentrated cell suspensions at a multiplicity of infection of 100 $CCID_{50}$ (50% cell culture infective dose) per $10^6$ cells. After 2 hr, cells were centrifuged to remove unadsorbed virus, resuspended in medium containing serial dilutions of the compounds, and transferred to 48-well plates. After 10-12 days incubation, viral CPE and compound cytotoxicity were scored by microscopy, and total DNA was extracted from the cells for quantitation of the viral DNA by qPCR. Anti-HHV-6 activity was expressed as $EC_{50}$, i.e., the compound concentration that produces 50% inhibition of virus replication, as estimated from the CPE score, or the amount of viral DNA as measured in the PCR assay.

For qPCR analysis on the DNA extracts, the SYBR® Green qPCR method was used. The forward and reverse primers were chosen to amplify a 150-bp fragment of the HHV-6 U67 gene. A standard curve was obtained by amplification of known amounts of a pGEM T-vector in which a 511-bp fragment of the HHV-6 U67 gene was inserted using common cloning procedures. These standard curves were used to convert the cycle threshold ($C_t$) values for the cell extracts into the absolute number of HHV-6 DNA copies. The $EC_{50}$ value was calculated by extrapolation as the compound concentration at which the number of viral DNA copies at 10-12 days p.i. was 50% compared to the value obtained for the virus control. (De Bolle et al., Biochem. Pharmacol. (2004), 67: 325-336.)

Antiviral Assays for Ortho- and Parapoxviruses.

These susceptibility assays were performed as previously described. Confluent HEL (ortho- and parapoxviruses), PHK (orthopoxviruses) and PLK (parapoxviruses) cells in 96-well microtiter plates were infected with a viral inoculum with a titer ranging from 20 to 60 pfu/well. After 2 hours of incubation at 37° C. and 5% $CO_2$, residual virus was removed and the infected cells were further incubated with medium containing serial dilutions of the compounds (in duplicate). After 2 to 3 days of incubation at 37° C. and 5% $CO_2$, the viral cytopathic effect (CPE) was recorded. The activity is expressed as $EC_{50}$ or effective compound concentration required to reduce virus-induced cytopathicity (CPE) by 50%, as compared to the untreated control.

Antiviral Assays for (Primate or Murine) Polyomavirus

Confluent monolayers of UC1-B or BS-C-1 cells grown in 96-well microtiter plates were infected with 100 $CCID_{50}$ of cell-free viruses. After 2 hours incubation, the inoculum was removed and replaced by the different dilutions (in duplicate) of the tested molecules. After 4 to 5 days (polyomavirus strains) or 6 to 7 days (SV40 strains) of incubation virus induced cytopathic effect (CPE) was monitored microscopically. The activity is expressed as $EC_{50}$ or effective compound concentration required for reducing virus-induced cytopathicity (CPE) by 50%, as compared to the untreated control.

Cytotoxicity Assays.

Confluent monolayers of UC-B or BS-C-1 grown in 96-well microtiter plates were incubated with different concentrations of the compounds (in duplicate) for 5 to 6 days. The cells were then trypsinized and the cell number was determined with a Coulter Counter. The toxicity of the compounds is expressed as $CC_{50}$ or compound concentration required for reducing cell number by 50%, as compared to an untreated control. The selectivity index is the ratio of $CC_{50}$ for cell toxicity to $EC_{50}$ for viral CPE.

Antiviral Assays for Moluscum Contagiosum Virus (MCV)

Twenty-four hour-old monolayers of PHKs grown in 96-well microtiter plates were infected with 100 $CCID_{50}$ of cell-free viruses. After 2 hours incubation, the inoculum was removed and replaced by the different dilutions (in duplicate) of the tested molecules. After 6 to 7 days of incubation virus induced cytopathic effect (CPE), characterized by the appearance of large infected cells, with internal organelles dislocated and obliterated by a large intracytoplasmic inclusion, was monitored microscopically. The activity is expressed as $EC_{50}$ or effective compound concentration required for reducing virus-induced cytopathicity (CPE) by 50%, as compared to the untreated control.

Cytotoxicity Assays and Minimal Cytotoxic Concentration

Minimal cytotoxic concentration for the different cell lines: The minimal cytotoxic concentration (MCC) is the lowest concentration of the compound in the antiviral assay where morphological changes characteristic of cytotoxicity were recorded.

Cytotoxicity assay for HEL cells: Toxicity of the compounds for the host cells was based on inhibition of cell growth. The cells were seeded at $4 \times 10^3$ cells per well in a volume of 0.1 ml into 96-well microtiter plates and allowed to proliferate for 24 h in MEM containing 20% FCS, 0.1% L-glutamine, and 0.3% sodium bicarbonate. Twenty-four hours later, MEM (with 2% FCS, 0.1% L-glutamine, and 0.3% sodium bicarbonate) containing different concentrations (in duplicate) of the test compounds was added (0.1 ml/well). After three days of incubation at 37° C. in 5% $CO_2$ atmosphere, the cell number was determined with a Coulter counter. The toxicity of the compounds is expressed as $CC_{50}$ or compound concentration required to reduce cell growth by 50%, as compared to an untreated control.

Cytotoxicity assay for PHK cells: Toxicity of the compounds for the host cells was based on inhibition of cell growth. The cells were seeded at $4 \times 10^3$ cells per well in a volume of 0.1 ml into 96-well microtiter plates and allowed to proliferate for 24 h in MEM containing 20% FCS, 0.1% L-glutamine, and 0.3% sodium bicarbonate. Twenty-four hours later, MEM (with 2% FCS, 0.1% L-glutamine, and 0.3% sodium bicarbonate) containing different concentrations (in duplicate) of the test compounds was added (0.1 ml/well). After three days of incubation at 37° C. in 5% $CO_2$ atmosphere, the cell number was determined with a Coulter counter. The toxicity of the compounds is expressed as $CC_{50}$ or compound concentration required to reduce cell growth by 50%, as compared to an untreated control.

Selectivity Index

The selectivity index (SI) is defined as the ratio of the $CC_{50}$ (the 50% cytotoxic concentration, i.e. the concentration that reduces by 50% the viability of cultured cells) for cell growth to the $EC_{50}$ (50% effective concentration, i.e. the concentration required to inhibit the viral cytopathic effect by 50% in cell culture) for viral plaque formation.

Example 9

Methods for In Vivo Determination of Antiviral Activity and Toxicity

Mice

The animals used throughout the experiments were adult NMRI (Naval Medical Research Institute) mice or athymic-nude (BALB/C nu/nu) mice of 18-20 g weight.

HSV Infection of NMRI Mice.

Animals were inoculated intraperitoneally (i.p.) with HSV-1 (KOS strain) or HSV-2 (Lyons strain) at $1 \times 10^3$ to $2 \times 10^3$ PFU/0.2 ml per mouse. The mice were treated for 5 days once a day (starting 1 h after infection) with the test compounds, which were administered subcutaneously (s.c.) at the indicated doses.

Vaccinia Virus and Cowpox Virus Infection of NMRI Mice.

Animals were inoculated intranasally (i.n.) with Vaccinia virus (Western Reserve) or cowpox virus (Brighton strain) with $4 \times 10^4$ PFU/20 µl per mouse. The mice were treated for 5 days once a day (starting 1 h after infection) with the test compounds, which were administered subcutaneously (s.c.) at the indicated doses. adult athymic nude (nu/nu).

Human Cervical Carcinoma (SiHa) Xenografts in Athymic Nude Mice.

Adult animals were injected s.c. with $5 \times 106$ SiHa cells, a human cervical carcinoma cell line which harbors integrated human papillomavirus (HPV-16). Once the tumors were established (approximately after 1 week), the mice were divided in several groups, the tumor size for each mouse was determined, and treatment with placebo (PBS) or the test compounds was started. The test solutions were administered intratumorally (i.t.) at a volume of 50 µl. Mice were treated once a day, 5 times a week for a period of 5 weeks. Every week, the tumor size for each animal was measured with a caliper in two perpendicular dimensions and tumor size was calculated by multiplying the two measured diameters.

Example 10

Antiviral Activity and Activity Against Virus Induced Cell Proliferation Disorders The compound (S)-1-[3-hydroxy-2-(phosphonomethoxy)propyl]-5-azacytosine and its equilibrium and deformylated product and its 6-aza analog, (S)-1-[3-hydroxy-2-(phosphonomethoxy)propyl]-6-azacytosine, were evaluated for their potential to inhibit the replication of different viruses in vitro and in vivo. Approximate values are shown which are average values taken from multiple experiments (mostly around 3).

For all the tables in this application showing antiviral activities, the following abbreviations have been used:

[a]$EC_{50}$: Effective concentration required to reduce virus-induced cytopathicity by 50%.

[b]MCC: Minimum cytotoxic concentration required to cause a microscopically detectable alteration of cell morphology.

[c]$CC_{50}$: Cytotoxic concentration required to reduce cell growth by 50%.

N.D.: not determined.

In Vitro

The compound (S)-1-[3-hydroxy-2-(phosphonomethoxy)propyl]-5-azacytosine has shown significant activity against:

- CMV (AD-169 and Davis), VZV (Oka, YS, YS-R and 07-1) and Poxviruses like Vaccinia virus (Lederle, Lister, W R and Copenhagen), Cowpox virus (Brighton) and Orf virus (NZ2) in HEL cells
- Herpes simplex virus-1 (KOS and TK⁻ KOS ACV'), Herpes simplex virus-2 (G) and Vaccinia virus in $E_6$SM cell cultures
- Poxviruses like Vaccinia virus (Lederle, Lister, W R and Copenhagen), Cowpox virus (Brighton) and Orf virus (NZ2) in PHKs.

Table 1 shows the results of the determination of the activity of the compounds of the invention against members of the Herpesviridae together with HPMPC as a point of comparison. Table 1

TABLE 1

| Compound (No) | EC$_{50}$ (μg/ml)$^a$ ||||||| Cytotoxicity ||
| | VZV |||| HCMV || Cell morphology (MCC)$^b$ HEL cells | Cell growth (CC50)$^c$ HEL cells |
| | YS strain (HEL cells) | OKA strain (HEL cells) | 07/1 strain (HEL cells) | YS-R strain (HEL cells) | AD-169 strain (HEL cells) | Davis strain (HEL cells) | | |
|---|---|---|---|---|---|---|---|---|
| 12 | <0.00002 | <0.00002 | <0.00002 | <0.00002 | <0.00002 | <0.00002 | >5 | 6.0 |
| 3 | 0.039 | 0.027 | 0.019 | 0.015 | 0.078 | 0.054 | >50 | >31.1 |
| 15 | N.D. | 0.063 | N.D. | N.D. | 0.0037 | 0.0014 | ≧100 | >100 |
| HPMP-6-azaC analogue | 42 | 38.2 | 18.4 | 17 | 30.0 | 37.3 | >100 | >50 |
| 11 | N.D. | 0.08 | 0.05 | N.D. | 0.093 | 0.061 | >100 | >50 |
| 3a | N.D. | 0.042 | 0.046 | N.D. | 0.10 | 0.12 | 100 | >50 |
| Cyclic HPMPC | N.D. | 0.18 | 0.08 | N.D. | 0.36 | 0.36 | >100 | >50 |
| HPMPC | N.D. | 0.2 | 0.05 | N.D. | 0.20 | 0.30 | 400 | 68.6 |

Table 2 shows the results of the determination of the activity of the compounds of the invention against members of the Poxyiridae in Hel cells together with HPMPC as a point of comparison.

TABLE 2

| Compound | EC$_{50}$ (μg/ml)$^a$ |||||| Cytotoxicity (μg/ml) ||
| | Vaccinia Virus |||| Cowpox virus Brighton | Orf virus NZ2 | Morphology (MCC)$^b$ | Growth (CC$_{50}$)$^c$ |
| | Lederle | Lister | WR | Copenhagen | | | | |
|---|---|---|---|---|---|---|---|---|
| 3 | 1.70 | 1.69 | 2.45 | 2.26 | 4.72 | 0.15 | >100 | ≧31.1 |
| HPMP-6-azaC | ≧81.6 | ≧79.3 | >100 | >100 | >100 | ≧63.8 | >100 | >50 |
| 11 | 3.1 | 1.38 | 2.08 | 1.76 | 5.64 | 0.09 | >100 | >50 |
| 3a | 7.97 | 7.61 | 6.34 | 5.84 | 12.63 | 0.37 | >100 | N.D. |
| 12 | <0.032 | <0.032 | 0.072 | <0.032 | <0.032 | <0.032 | 20 | N.D. |
| HPMPC | 2.43 | 2.45 | 5.82 | 4.35 | 8.43 | 0.20 | >100 | 68.6 |
| Cyclic HPMPC | 7.61 | 2.19 | 4 | 3.06 | 8.94 | 0.21 | >100 | 68.6 |

Table 3 shows the drug-susceptibility profile of Vaccinia virus (Western Reserve) and recombinant viruses harboring the A314T, A684V or A314T+A684V mutations. These mutations were found in viral mutants selected after about 40 passages in increasing concentrations of HPMPC and HPMP-5-azaC.

(EC50 in μg/mL)

TABLE 3

| Virus type | HPMPC | HPMP-5-azaC (3) |
|---|---|---|
| wild-type | 3.1 | 1.58 |
| A314T | 22.2 | 4.1 |
| 684 | 14.8 | 6.88 |
| 314 + 684 | 39.5 | 10.8 |

Table 4 shows antiviral activity of a prodrug of cHPMP-5-azaC against herpes simplex virus type 1 (HSV-1) and type 2 (HSV-2) in HEL cells

TABLE 4

| | $EC_{50}$ (μg/ml)[a] | | Cytotoxicity (μg/ml) | |
|---|---|---|---|---|
| Compound | HSV-1 (Kos strain) | HSV-2 (G strain) | Morphology (MCC)[b] | Growth $(CC_{50})$[c] |
| 3 | 0.61 | 0.54 | >100 | N.D. |
| HPMPC | 0.16 | 0.54 | >100 | N.D. |
| Cyclic HPMPC | 0.16 | 0.58 | >100 | N.D. |
| 11 | 0.017 | 0.58 | >100 | N.D. |
| 12 | 0.072 | 0.36 | >20 | N.D. |
| Acyclovir | 0.032 | 0.032 | >100 | N.D. |

Table 5 shows the antiviral activity of (S)-HPMP-5-azaC and cHPMP-5-azaC and esters thereof (HDE-cHPMP-5-azaC=hexadecyloxyethyl ester of cHPMP-5-aza-C) against primate polyomavirus in BS-C-1 cells

| compound | antiviral activity (EC$_{50}$)$^a$ | | | cytotoxicity CC$_{50}$$^b$ | selectivity index$^c$ | | |
|---|---|---|---|---|---|---|---|
| | SV40 strain A2895 | SV40 PML-1 strain EK | SV40 PML-2 strain DAR | | SV40 strain A2895 | SV40 PML-1 strain EK | SV40 PML-2 strain DAR |
| (S)-HPMPC | 4.72 | 5.56 | 5.87 | 79.39 | 17 | 14 | 14 |
| 3 | 3.22 | 3.19 | 3.81 | 128.75 | 40 | 40 | 34 |
| Cyclic HPMPC | 5.72 | 5.25 | 5.19 | 98.22 | 17 | 19 | 19 |
| 11 | 4.39 | 4.60 | 5.05 | 36.44 | 8 | 8 | 7 |
| 3a | 5.92 | 10.00 | 8.24 | >200 | >34 | >20 | >24 |
| 10 | >200 | >200 | >200 | >200 | 1 | 1 | 1 |
| HDE-cHPMP-5-azaC (12) | 0.16 | 0.15 | 0.18 | 7.10 | 44.5 | 57.6 | 38.7 |

Table 6 shows the antiviral activity of (S)-HPMP-5-azaC, cHPMP-5-azaC and esters thereof (HDE-cHPMP-5-azaC=hexadecyloxyethyl ester of cHPMP-5-aza-C) against murine polyomavirus in UC1-B cells

| compound | antiviral activity (EC$_{50}$)$^a$ | | | | cytotoxicity CC$_{50}$$^b$ | selectivity index$^c$ | | | |
|---|---|---|---|---|---|---|---|---|---|
| | MN/RDE Toronto | PTA | 2PTA2 | LID-1 | | MN/RDE Toronto | PTA | 2PTA2 | LID-1 |
| (S)-HPMPC | 2.76 | 6.54 | 5.78 | 5.89 | 84.34 | 31 | 13 | 15 | 14 |
| 3 | 1.94 | 3.89 | 3.35 | 4.98 | 109.46 | 56 | 28 | 33 | 22 |
| Cyclic HPMPC | 12.28 | 16.22 | 18.60 | 21.17 | 71.02 | 6 | 4 | 4 | 3 |
| 11 | 3.43 | 8.59 | 4.39 | 8.05 | 58.44 | 17 | 7 | 13 | 7 |
| 3a | 7.57 | N.D. | 14.84 | N.D. | >200 | >26 | N.D. | >13 | N.D. |
| 10 | >200 | >200 | >200 | >200 | >200 | 1 | 1 | 1 | 1 |
| HDE-cHPMP-5-azaC (12) | 0.29 | 0.28 | 0.30 | 0.47 | 10.0 | 34.9 | 35.6 | 33.8 | 21.3 |

Table 7 shows the Activity of (S)-HPMP-5-azaC compared to (S)-HPMPC against clinical isolates of Molluscum contagiosum virus (MCV) in primary human keratinocytes.

TABLE 7

| | EC$_{50}$ (µg/ml) | | | | |
|---|---|---|---|---|---|
| Compound | MCV 06/02 | MCV 06/03 | MCV 06/04 | MCV 06/06 | MCC (µg/ml) |
| (S)-HPMPC | 0.76 | 0.55 | 0.55 | 0.6 | 50 |
| 3 | 0.4 | 0.23 | 0.4 | 1.26 | 50 |

Table 8 shows the long lasting activity of (S)-HPMPC compared to (S)-HPMP-5-azaC (3). HEL cells were infected with HSV-1 (Kos strain) or vaccinia virus (Lederle strain) and the compounds were added before or after infection and remained in contact with the cells for the indicated period of time. The cultures were washed then 3× to remove residual compound. Time of infection is considered as 0 h.

TABLE 8

| | EC$_{50}$ (µg/ml) | | | |
|---|---|---|---|---|
| | Vaccinia (Lederle strain) | | HSV-1 (Kos strain) | |
| Incubation time | (S)-HPMPC | (S)-HPMP-5-azaC (3) | (S)-HPMPC | (S)-HPMP-5-azaC (3) |
| Pretreatment (−16 hours) | 5 | 1.59 | 1 | 0.25 |
| Treatment 2-4 hours | 20 | 5 | 2.51 | 1 |
| Treatment 2-6 hours | 9.06 | 3.98 | 1.1 | 0.37 |
| Treatment 2-8 hours | 10 | 6.3 | 1 | 0.32 |
| Treatment from 2 h till end of experiment | 3.98 | 2 | 0.43 | 0.16 |

Table 9 shows anti-adenovirus activity of compounds of the invention in human embryonic lung fibroblast HEL cells infected with human adenovirus type 2. The results show that compound 3 (5-aza-HPMPC) is clearly more active against Ad2 than cidofovir.

TABLE 9

| | Antiviral activity (µg/mL) | | Toxicity (µg/mL) | |
|---|---|---|---|---|
| Product | EC$_{50}$ (CPE) | EC$_{50}$ (MTS) | MCC (microscop) | CC$_{50}$ (MTS) |
| HPMPC | 1.4 | 3.2 | >79 | >79 |
| 3 | 0.6 | 1.1 | >100 | >100 |
| 3a | 11.3 | 31.8 | >100 | >100 |

TABLE 10 anti-HHV-6 results

| Product | Antiviral activity (μg/ml) $EC_{50}$ (CPE) | $EC_{50}$ (qPCR) | Toxicity (μg/ml) MCC (microscopy) |
|---|---|---|---|
| A) Anti-HHV-6A activity in HSB-2 cells infected with HHV-6A, strain GS. | | | |
| HPMPC | 3.9 | 2.1 | 19 |
| 3 | 0.55 | 0.56 | 16 |
| 3a | 5.8 | 20.8 | >200 |
| 10 | >200 | ND | >200 |
| B) Anti-HHV-6B activity in MOLT-3 cells infected with HHV-6B, strain Z29. | | | |
| HPMPC | 0.84 | 0.56 | 32 |
| 3 | 0.23 | 0.34 | 16 |
| 3a | 3.6 | 5.5 | 200 |

In Vivo

The subcutaneous administration of the compound (1/day) yielded a 100% survival rate in a HSV-1 (KOS) mice in vivo experiment during 20 weeks, while in the control group 80% didn't survive. For the HSV-2 (Lyons) model, the survival rate with the compound was 100% after 20 days, while it was 40% in the control group.

Also the subcutaneous administration of the compound yielded a 100% survival in a Cowpox virus (Brighton) mice model after 20 days while in the control group there was a 0% survival after 10 days.

In a Vaccinia Virus (WR) mice model, administration of the compound yielded a 100% survival after 20 days, while not any mouse survived day 7 in the control group. Also the number of lesions on day 7 was reduced to 0 in a pox tail lesion model compared to an average of 17 lesions in the control group.

In the experiments with human cervical carcinoma (SiHa) xenografts in athymic nude mice, the tumor size did not increase during a 5 weeks intratumoral treatment with the compound, while in the untreated control group the tumor size increased with 600%. In all the in vivo experiments, the mean body weights of the mice have been investigated and yielded a normal pattern.

FIGS. 2 to 12 show the results of the in vivo experiments in more detail.

The results of the investigations of the effects of (S)-HPMP-5-azaC on human cervical carcinoma are clearly visible from FIG. 12 and it is shown that 5 and 10 mg/mL doses of (S)-HPMP-5-azaC inhibit the growth of tumors.

Example 11

Renal Toxicity

These experiments relates to the investigation of the cytostatic activity of the compounds of the invention for primary cultures of human renal cells, compared to HPMPC.

Materials and methods: Two different primary human renal cells were used: RPTEC (renal proximal tubule epithelial cells) and human renal cortex epithelial (HRCE) cells. Cytostatic activity of the compounds was measured on growing cells (cells in exponentially phase of growth) or resting cells (confluent monolayers).

Cells grown in 96-well microtiter plates were incubated with different concentrations of the compounds (in duplicate) for the indicated period of time. The cells were then trypsinized and the cell number was determined with a Coulter Counter. Percentage of control was calculated as the number of cells in the treated samples divided by the number of cells in the untreated controls. The cytostatic activity of the compounds is expressed as $CC_{50}$ or compound concentration required for reducing cell number by 50%, as compared to an untreated control.

The results of these experiments are as following:

Table 11: A, B, C, D, E and F show the cytostatic activity on human renal cells under different conditions A) Cytostatic activity for growing human renal proximal tubule epithelial cells (RPTEC) #4 after 7 days of incubation with or without medium refreshing.

| | $CC_{50}$ (μg/ml) | |
|---|---|---|
| Compounds | No medium refreshing | Medium refreshing |
| 3 | >50 | >50 |
| 3a | >50 | >50 |
| 10 | >50 | >50 |
| (S)-HPMPC | 44.23 | 45.94 |

B) Cytostatic activity for resting human renal proximal tubule epithelial cells (RPTEC) #4 after 16 days of incubation without medium refreshing.

| Compound | $CC_{50}$ (μg/ml) |
|---|---|
| 3 | >50 |
| 3a | >50 |
| 10 | >50 |
| (S)-HPMPC | 12.7 |

C) Cytostatic activity for growing human renal proximal tubule epithelial cells (RPTEC) #6 after 6 or 8 days of incubation without medium refreshing.

| | $CC_{50}$ (μg/ml) | |
|---|---|---|
| Compounds | 6 days | 8 days |
| 3 | ≧200 | 149.4 |
| 3a | >200 | >200 |
| 10 | >200 | >200 |
| (S)-HPMPC | 42.2 | 14.2 |

D) Cytostatic activity for growing human renal proximal tubule epithelial cells (RPTEC) #6 after 5 or 7 days of incubation without medium refreshing.

| | $CC_{50}$ (μg/ml) | |
|---|---|---|
| Compounds | 5 days | 7 days |
| 3 | ≧200 | 135.8 |
| 3a | >200 | >200 |
| 10 | >200 | >200 |
| (S)-HPMPC | 42.2 | 55.6 |

E) Cytostatic activity for resting renal proximal tubule epithelial cells (RPTEC) #7 after 6 or 8 days of incubation without medium refreshing.

| Compounds | CC$_{50}$ (μg/ml) | |
|---|---|---|
| | 5 days | 7 days |
| 3 | ≧200 | ≧200 |
| 3a | >200 | >200 |
| 10 | >200 | >200 |
| (S)-HPMPC | 94.6 | 86.8 |

Example 12

Synthesis of (S)-1-[3-hydroxy-2-(Phosphonomethoxy)propyl]-5-azacytosine (HPMP-5-azaC)

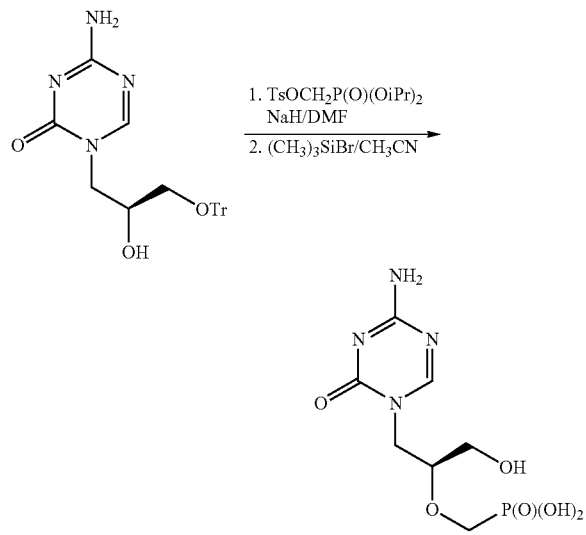

A solution of 1-[(2S)-2-hydroxy-3-(triphenylmethoxy)propyl]-5-azacytosine (934 mg, 2.18 mmol) and diisopropyl tosyloxymethylphosphonate (1.05 g, 3 mmol) in DMF (30 ml) was cooled to −20° C. and 60% oil dispersion of NaH (240 mg, 6 mmol) was added. The mixture was stirred at −20° C. for 15 min, then the temperature was let to rise to approx. 25° C. (room temperature) and the stirring continued for additional 15 h. Acetic acid was added drop wise to pH 7, the mixture evaporated and the residue coevaporated with toluene (2×50 ml). Acetonitrile (30 ml) was added, followed by bromotrimethylsilane (2.7 ml, 20 mmol), the resulting suspension stirred in dark at room temperature for 48 h and evaporated. The residue was coevaporated with acetonitrile (3×50 ml). 90% Aqueous solution of methanol (50 ml) was added and the solution neutralized to pH 7.0 with 0.2 M triethylammonium hydrogencarbonate. The solution was concentrated to minimal volume (approx. 5 ml) and partitioned between water (100 ml) and ether (100 ml). An aqueous layer was concentrated to a volume 5 ml and applied onto a column of Dowex 1 (AcO⁻ form, 60 ml). Elution was performed with water (300 ml), then with a linear gradient of acetic acid (0.5-1 M, 1 l) and lastly, the pure product was eluted with 1 M formic acid. UV absorbing fractions were taken down in vacuo and the residue coevaporated several times with water till a complete removal of acid. The residue was crystallized from aqueous ethanol, crystals collected by suction, washed with ethanol and ether and dried in vacuo. Yield: 200 mg (33%) of pure HPMP-5-azaC.

Example 13

Synthesis of hexadecyloxyethyl ester of 1-{[(5S)-2-hydroxy-2-oxido-1,4,2-dioxaphosphinan-5-yl]methyl}-5-azacytosine

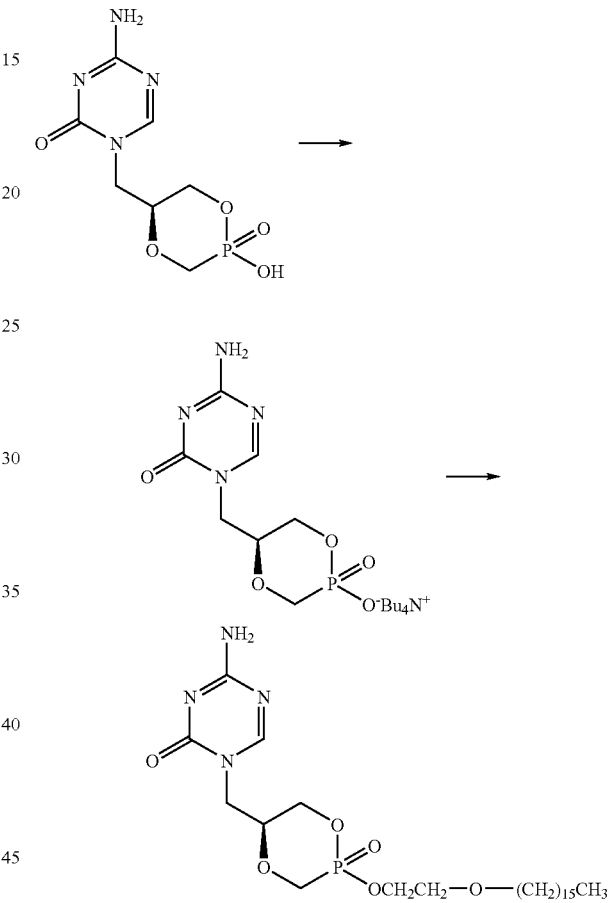

1 M Methanolic solution of tetrabutylammonium hydroxide (1.73 ml; 1.73 mmol) was added to a solution of cyclic HPMP-5-azaC (454 mg, 1.73 mmol) in absolute methanol (50 ml), the mixture stirred for 5 min, then evaporated and the residue coevaporated with toluene (2×40 ml). The residue was dissolved in DMF (5 ml) and heated with hexadecyloxyethyl bromide (1.4 g, 4.0 mmol) at 100° C. for 6 h. The reaction mixture was evaporated, the residue coevaporated with xylene (2×25 ml) and chromatographed on a column of silica gel (100 ml) in system chloroform-methanol (85:15) to give 1 g of a white solid, still containing rests of tetrabutyl ammonium salts (NMR control). The crude product was crystallized from methanol, crystals collected by suction, washed with methanol followed by diethyl ether and dried in vacuo. Yield of pure product: 450 mg (49%). Mother liquors were purified by reverse phase HPLC technique (Waters Delta 600 instrument with a Waters 2487 Dual λ Absorbance Detector, using preparative column Luna Phenomenex® C-18 (21×250 mm), flow rate 12 ml/min, gradient: 20-90% CH$_3$OH in water during 45 min). Overall yield of pure product: 485 mg (53%).

Example 14

Synthesis of octadecyl ester of 1-{[(5S)-2-hydroxy-2-oxido-1,4,2-dioxaphosphinan-5-yl]methyl}-5-azacytosine (15)

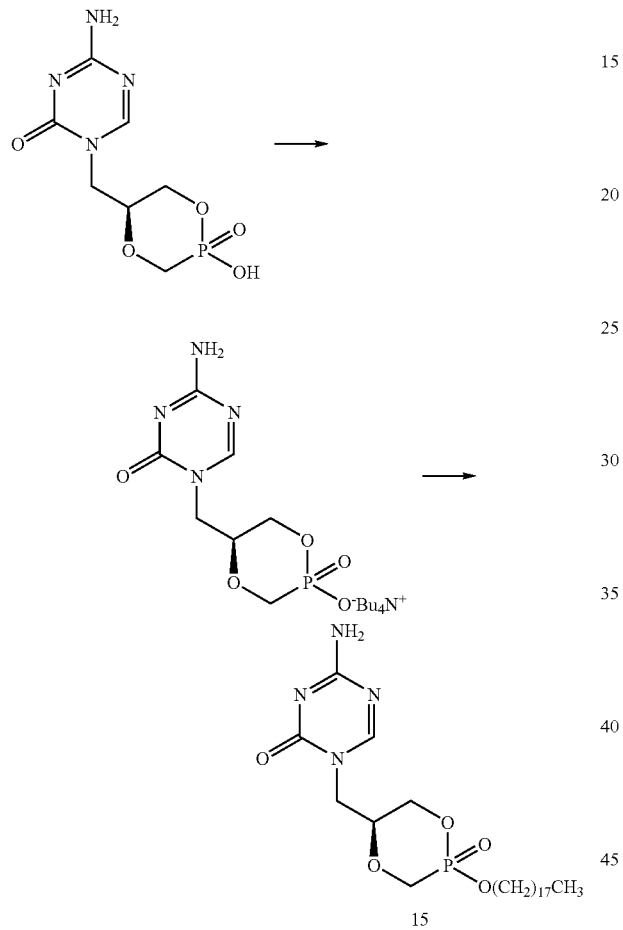

1 M Methanolic tetrabutylammonium hydroxide (0.61 ml; 0.61 mmol) was added to a solution of cyclic HPMP-5-azaC (161 mg, 0.61 mmol) in absolute methanol (50 ml), the mixture stirred for 5 min, then evaporated and the residue coevaporated with toluene (20 ml), followed by dry dioxane (20 ml). The residue was dissolved in dioxane (10 ml) and stirred with octadecyl bromide (500 mg, 1.5 mmol) at 95° C. for 3 h. The reaction mixture was evaporated, the residue chromatographed on a column of silica gel (30 ml) in system chloroform-methanol (85:15). Yield: 250 mg, 80%, white solid. ESI MS: 1051.0 (2M+Na)$^+$ (41), 537.3 (M+Na)$^+$ (64), 515.3 (23) (MH)$^+$. HRMS (ESI): For C$_{25}$H$_{48}$N$_4$O$_5$P (MH$^+$) calculated: 515.3362. Found: 515.3382. $^1$H NMR (DMSO-d$_6$): 8.11 s, 1H (H-6); 7.46 brs, 1H and 7.45 brs, 1H (NH$_2$); other signals not distinguished. $^{13}$C NMR (DMSO-d$_6$): 166.50 (C-4); 159.62 (C-6); 153.95 (C-2); 73.19 d, J (P, C)=4.9 (C-2'); 72.04 d, J (P, C)=12.4 (C-3'); 65.19 d, J (P, C)=5.9 (OCH$_2$); 62.70 d, J (P, C)=141.6 (P—C); 45.75 (C-1'); 31.44, 30.03, 29.18, 5 C, 29.09, 25.09, 23.24, 5 C, 22.24 and 19.37 (CH$_2$); 13.65 (CH$_3$).

Example 15

Pivaloyloxymethyl ester of 1-{[(5S)-2-hydroxy-2-oxido-1,4,2-dioxaphosphinan-5-yl]methyl}-5-azacytosine (cyclic POM-HPMP-azaC)

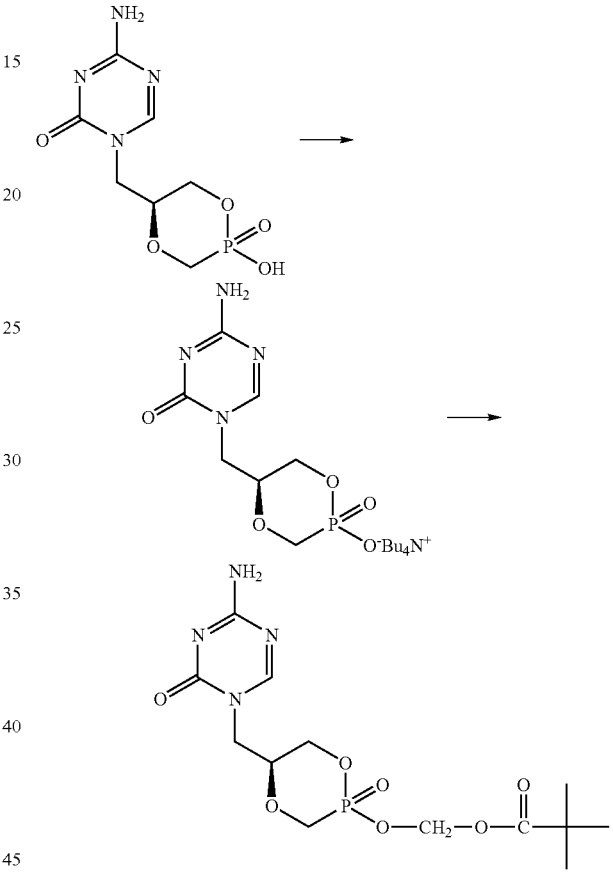

1 M Methanolic tetrabutylammonium hydroxide (1.022 ml; 1.022 mmol) was added to a solution of cyclic HPMP-5-azaC (268 mg, 1.022 mmol) in absolute methanol (50 ml), the mixture stirred for 5 min, then evaporated and the residue coevaporated with toluene (20 ml), followed by dry dioxane (20 ml). The residue was dissolved in dioxane (10 ml) and stirred with chloromethyl pivalate (1.5 ml, 10.4 mmol) at 100° C. for 2 h. After cooling to room temperature, the reaction was quenched with methanol (1 ml) and the mixture evaporated. The residue was chromatographed on a column of silica gel (50 ml) in system chloroform-methanol (85:15) to give 270 mg (70%) of cyclic POM-HPMP-5-azaC containing traces of tetrabutyl ammonium salts. The product was finally purified by reverse phase HPLC technique (Waters Delta 600 instrument with a Waters 2487 Dual A Absorbance Detector, using preparative column Luna Phenomenex® C-18 (21×250 mm), flow rate 12 ml/min, isocratic elution with 20% methanol, retention time 12 min). Yield: 200 mg (52%), white foam. The compound is a mixture of diastereoisomers ~5:2. HRMS (FAB): For $C_{13}H_{22}N_4O_7P$ (MH$^+$) calculated: 377.1226. Found: 377.1218. NMR data:

Major Diastereoisomer:

$^1$H NMR (500 MHz, CDCl$_3$): 1.25 (s, 8H, (CH$_3$)$_3$C); 3.51 (dd, 1H, J$_{gem}$=14.1, J$_{vic}$=7.8, CH$_a$H$_b$N); 3.97 (d, 1H, J$_{gem}$=14.8, CH$_a$H$_b$P); 4.09 (m, 1H, CHO); 4.10 (m, 1H, CH$_a$H$_b$N); 4.18 (dd, 1H, J$_{gem}$=14.8, J$_{H,P}$=11.2, CH$_a$H$_b$P); 4.27 (bt, 1H, J$_{gem}$~J$_{vic}$=10.7, CH$_a$H$_b$O); 4.42 (m, 1H, CH$_a$H$_b$O); 5.71 and 5.75 (2×dd, 2H, J$_{gem}$=11.9, J$_{vic}$=5.2, OCH$_2$O); 6.35 and 7.30 (2×bs, 2H, NH$_2$); 7.95 (s, 1H, H-6).

$^{13}$C NMR (125.7 MHz, CDCl$_3$): 26.76 ((CH$_3$)$_3$C); 38.69 (C(CH$_3$)$_3$); 46.61 (CH$_2$N); 64.07 (d, J$_{C,P}$=144, CH$_2$P); 72.24 (d, J$_{C,P}$=9, CH$_2$O); 73.23 (d, J$_{C,P}$=5, CHO); 81.44 (d, J$_{C,P}$=6, OCH$_2$O); 154.19 (C-2); 158.98 (CH-6); 166.43 (C-4); 176.94 (CO).

Minor Diastereoisomer:

$^1$H NMR (500 MHz, CDCl$_3$): 1.22 (s, 8H, (CH$_3$)$_3$C); 3.67 (dd, 1H, J$_{gem}$=13.8, J$_{vic}$=7.9, CH$_a$H$_b$N); 3.88 (dd, 1H, J$_{gem}$=14.1, J$_{H,P}$=1.9, CH$_a$H$_b$P); 4.11 (m, 1H, CHO); 4.13 (m, 1H, CH$_a$H$_b$N); 4.29 (dd, 1H, J$_{gem}$=14.1, J$_{H,P}$=9.4, CH$_a$H$_b$P); 4.45 (m, 2H, CH$_2$O); 5.60 and 5.77 (2×dd, 2H, J$_{gem}$=13.8, J$_{vic}$=5.2, OCH$_2$O); 6.45 and 7.19 (2×bs, 2H, NH$_2$); 8.04 (s, 1H, H-6).

$^{13}$C NMR (125.7 MHz, CDCl$_3$): 26.71 ((CH$_3$)$_3$C); 38.62 (C(CH$_3$)$_3$); 46.61 (CH$_2$N); 64.39 (d, J$_{C,P}$=147, CH$_2$P); 70.84 (d, J$_{C,P}$=6, CH$_2$O); 72.87 (d, J$_{C,P}$=4, CHO); 81.77 (d, J$_{C,P}$=5, OCH$_2$O); 154.27 (C-2); 159.16 (CH-6); 166.43 (C-4); 176.94 (CO).

Example 16

Synthesis of 6-alkyl substituted-5-azacytosine derivatives

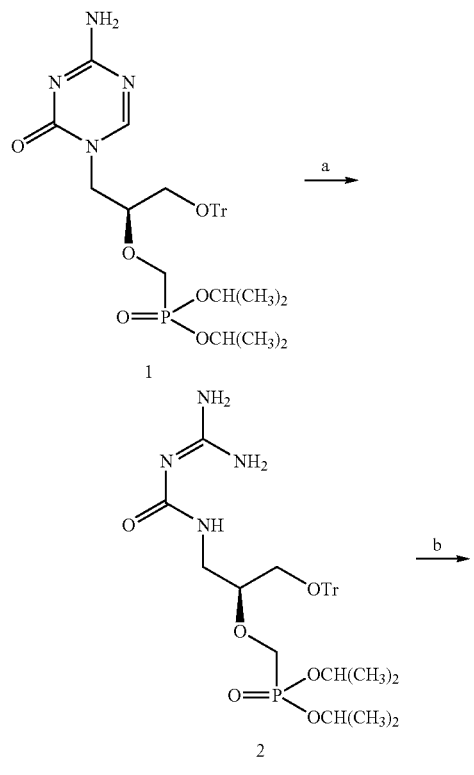

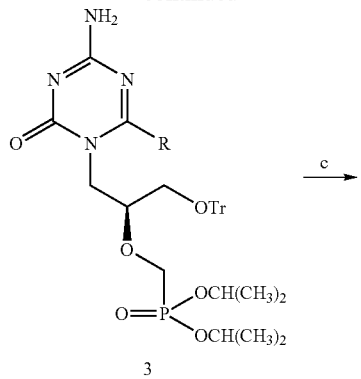

HPMP-6-alkyl-5-azacytosine

Conditions: (a) 25% aq. NH$_4$OH+CH$_3$OH 1:1, r.t., 5 days; (b) Orthoester, DMF, 150° C., 3 h; (c) (CH$_3$)$_3$SiBr, CH$_3$CN, r.t., 24 h Orthoesters: CH$_3$C(OC$_2$H$_5$)$_3$ for R=CH$_3$, CH$_3$CH$_2$CH$_2$CH$_2$C(OCH$_3$)$_3$ for R=butyl, C$_6$H$_5$C(OCH$_3$)$_3$ for R=phenyl.

A mixture of 1 (1.45 g, 2.39 mmol), methanol (30 ml) and 25% aqueous ammonia (30 ml) was stirred at room temperature for 5 days. TLC control was performed in system ethyl acetate-acetone-ethanol-water 18:3:1:1, the spot of 2 (lacking UV absorption) was detected by spraying with a mixture of 5% K$_3$-[Fe(CN)$_6$]+5% NaOH+5% Na$_2$[Fe(CN)$_5$NO] (orange spot). The mixture was evaporated and the residue coevaporated with absolute ethanol to give oily residue of 2 (1.4 g). This material was dissolved in DMF (15 ml) and heated with appropriate orthoester (1 ml) at 150° C. for 1.5-3 h (TLC control). The mixture was then evaporated, the residue chromatographed on a column of silica gel (200 ml) in system ethyl acetate-acetone-ethanol-water 18:3:1:1. Yield of 3: 50-70%. Deprotection of 3 to final 6-alkyl HPMP-5-azaC (4) was performed by the same procedure as described for HPMP-5-azaC.

Example 17

Synthesis of 6-Substituted azacytosine Derivatives with R=COOH, CONH$_2$, COOC$_2$H$_5$ These compounds are prepared from compound 2 from example 17 by cyclization reaction with oxalic acid esters, e.g. KOOC—COOC$_2$H$_5$, H$_2$NCO—COOC$_2$H$_5$, (COOC$_2$H$_5$)$_2$.

Example 18

Synthesis of 6-Substituted azacytosine Derivatives with R=OH or NH$_2$

6-Amino derivative and 6-hydroxy derivatives are prepared by condensation of a sodium salt of 6-amino-5-azacytosine (ammeline) or 6-hydroxy-5-azacytosine (with protected OH group) and HPMP synthon, i.e. (2S)-2-[(diisopropylphosphoryl)methoxy]-3-hydroxypropyl 4-methylbenzenesulfonate.

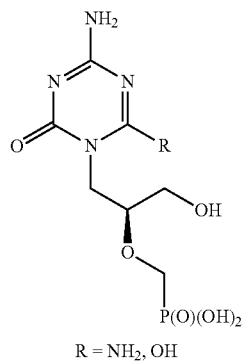

R = NH$_2$, OH

Example 19

Synthesis and activity of 5,6-dihydro derivatives of 5 azacytosine derivatives 5,6-dihydro derivative of HPMP-5-azaC, showed an activity against Herpesviruses with an EC50 ranging from 3 to 12 µg/mL and proved to be inhibitory to vaccinia virus (EC50=38 µg/mL). 5,6-dihydro derivative of HPMP-5-azaC was the only compound in this series to show activity against RNA-viruses, namely it was able to inhibit HCV subgenomic replicon replication in Huh-5-2 cells with an EC50 of 24 µg/mL and CC50 in Huh-5-2 cells of 120 µg/mL.
(S)-1-[3-Hydroxy-2-(phosphonomethoxy)propyl]-5,6-dihydro-5-azacytosine. A mixture of compound (S)-HPMP-5-azaC (110 mg, 0.39 mmol) in methanol (15 mL) and acetic acid (0.5 mL) was stirred till a complete dissolution (1 h, approx.) and then hydrogenated on 10% palladium on charcoal (20 mg) under atmospheric pressure at room temperature till UV absorption disappeared (48 h). The catalyst was filtered off through a Celite pad, the filtrate passed through Nylon membrane filter Whatman 0.2 µm, evaporated in vacuo and the product lyophilized. Yield: 80 mg, 73%. [α]$_D$ −2.9 (c 0.259, H$_2$O). FABMS: 283 (MH$^+$) (16). HRMS (FAB): For C$_7$H$_{16}$N$_4$O$_6$P (MH$^+$) calculated: 283.0807. Found: 283.0807. $^1$H NMR (D$_2$O): 4.88 d, 1H and 4.79 d, 1H, J$_{gem}$=10.5 (NCH$_2$N); 3.87 dd, 1H, J (P, CH$_a$)=9.2, J$_{gem}$=13.2 (PCH$_a$); 3.87 dd, 1H, J (3'a, 2')=3.8, J$_{gem}$=12.2 (H-3'a); 3.74 m, 2H (H-2', PCH$_b$); 3.67 dd, 1H, J (1'a, 2')=3.3, J(gem)=14.9 (H-1'a); 3.60 dd, 1H, J (3'b, 2')=4.0 (H-3'b); 3.46 dd, 1H, J (1'b, 2')=7.7 (H-1'b). $^{13}$C NMR (D$_2$O): 153.94 (C-4); 151.54 (C-2); 80.51 d, J (C, P)=11.7 (C-2'); 65.35 d, J (C, P)=159.7 (P—C); 60.99 (C-3'); 56.28 (C-6); 46.46 (C-1').

Example 20

Anti-HCV Assay/Replicon Assay

Huh-5-2 cells [a cell line with a persistent HCV replicon I389luc-ubi-neo/NS3-3'/5.1; replicon with firefly luciferase-ubiquitin-neomycin phosphotransferase fusion protein and EMCV-IRES driven NS3-5B HCV polyprotein] was cultured in RPMI medium (Gibco) supplemented with 10% fetal calf serum, 2 mM L-glutamine (Life Technologies), 1× non-essential amino acids (Life Technologies); 100 IU/ml penicillin and 100 ug/ml streptomycin and 250 ug/ml G418 (Geneticin, Life Technologies). Cells were seeded at a density of 7000 cells per well in 96 well View Plate™ (Packard) in medium containing the same components as described above, except for G418. Cells were allowed to adhere and proliferate for 24 hr. At that time, culture medium was removed and serial dilutions of the test compounds were added in culture medium lacking G418. Interferon alfa 2a (500 IU) was included as a positive control. Plates were further incubated at 37° C. and 5% CO$_2$ for 72 hours. Replication of the HCV replicon in Huh-5 cells results in luciferase activity in the cells. Luciferase activity is measured by adding 50 µl of 1× Glo-lysis buffer (Promega) for 15 minutes followed by 50 ul of the Steady-Glo Luciferase assay reagent (Promega). Luciferase activity is measured with a luminometer and the signal in each individual well is expressed as a percentage of the untreated cultures. Parallel cultures of Huh-5-2 cells, seeded at a density of 7000 cells/well of classical 96-well cell culture plates (Becton-Dickinson) are treated in a similar fashion except that no Glo-lysis buffer or Steady-Glo Luciferase reagent is added. Instead the density of the culture is measured by means of the MTS method (Promega).

Example 21

Synthesis of diisopropyl(S)-1-[3-Hydroxy-2-(phosphonomethoxy)propyl]-6-azacytosine A mixture of a sodium salt of 6-azacytosine (1 molar equivalent) and the tosylate synthon 8 (1 molar equivalent) in dimethylformamide is heated to 90° C. with exclusion of moisture for 5 h. Additional portion of the tosylate (0.3 molar equivalent) is added together with a catalytic amount of cesium carbonate and the heating continued at 120° C. until a complete dissolution occurs. The reaction mixture is taken down, the residue coevaporated with toluene and xylene and applied onto a column of silica gel in system chloroform-methanol. The product containing fractions were taken down and coevaporated with absolute ethanol.

Examples 22 to 24

Synthesis of 6-alkylsubstituted analogues of the 5-azacytosine compound 3

The method of example 1, i.e. following the principle of scheme 1, is repeated except that 4-amino-1,3,5-triazin-2 (1H)-one as a starting material is replaced respectively with:
4-amino-6-methyl-1,3,5-triazin-2(1H)-one (example 22),
4-amino-6-isopropyl-1,3,5-triazin-2(1H)-one (example 23), or
4-amino-6-(tert-butyl)-1,3,5-triazin-2(1H)-one (example 24).
The following compounds are obtained in similar yields:
(S)-1-[3-hydroxy-2-(phosphonomethoxy)propyl]-5-aza-6-methyl-cytosine (example 22),
(S)-1-[3-hydroxy-2-(phosphonomethoxy)propyl]-5-aza-6-isopropyl-cytosine (example 23), and
(S)-1-[3-hydroxy-2-(phosphonomethoxy)propyl]-5-aza-6-(tert-butyl)-cytosine (example 24).

Examples 25 to 27

Alternative Synthesis of 6-alkylsubstituted Analogues of the 5-azacytosine Compound 3

The method of example 2, i.e. following the principle of scheme 3, is repeated except that the sodium salt of 4-amino-1,3,5-triazin-2(1H)-one as a starting material in step (f) is replaced respectively with the sodium salts of:
4-amino-6-methyl-1,3,5-triazin-2(1H)-one (example 25),
4-amino-6-isopropyl-1,3,5-triazin-2(1H)-one (example 26), or
4-amino-6-(tert-butyl)-1,3,5-triazin-2(1H)-one (example 27).

The 6-alkyl substituted analogues of compound 3 are obtained in similar yields.

Example 28

Synthesis of the 6-azacytosine Analogue of Compound 3

The method of example 1, i.e. following the principle of scheme 1, is repeated except that 4-amino-1,3,5-triazin-2(1H)-one as a starting material is replaced with 4-amino-1,2,4-triazin-2(1H)-one. The 6-azacytosine analogue of compound 3 is obtained in similar yield.

The invention claimed is:

1. An azacytosine compound according to the structural formula (I), a stereochemically isomeric form thereof, or a salt thereof:

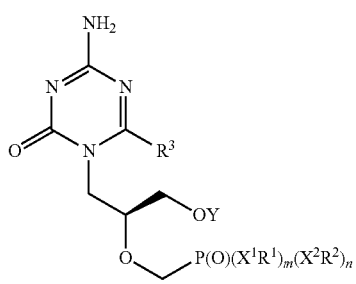

(I)

wherein
R$^1$ and R$^2$ are independently selected from the group consisting of hydrogen, C$_{1-30}$ alkyl, C$_{2-30}$ alkenyl, C$_{2-30}$ alkynyl, aryl, C$_{1-30}$ alkylphenyl and aryl-C$_{1-30}$ alkyl wherein each of said C$_{1-30}$ alkyl, C$_{2-30}$ alkenyl or C$_{2-30}$ alkynyl optionally contains one or more heteroatoms selected from the group consisting of oxygen, nitrogen and sulphur in the main chain and/or is optionally substituted with one or more substituents selected from the group consisting of hydroxy, oxo and halogen or R$^1$ and R$^2$ are linked by one or more bonds to form a five, six or seven membered ring comprising P, X$^1$ and X$^2$, said ring being optionally fused with a phenyl ring;
X$^1$ is selected from the group consisting of NR$^4$ and oxygen;
X$^2$ is selected from the group consisting of NR$^5$ and oxygen;
R$^4$ and R$^5$ are independently selected from the group consisting of hydrogen, C$_{1-30}$ alkyl, C$_{2-30}$ alkenyl and C$_{2-30}$ alkynyl, wherein each of said C$_{1-30}$ alkyl, C$_{2-30}$ alkenyl or C$_{2-30}$ alkynyl optionally contains one or more heteroatoms selected from the group consisting of oxygen, nitrogen and sulphur in the main chain and/or is optionally substituted with one or more substituents selected from the group consisting of hydroxy and halogen;
Y is hydrogen or is a bond linking oxygen to phosphorous to form a six-membered cyclic phosphonic acid ester;
each of m and n is 1 when Y is hydrogen, or one of m and n is 1 and the other one of m and n is 0 when Y is a bond linking oxygen to phosphorous to form a 6-membered cyclic phosphonic acid ester;
R$^3$ is selected from the group consisting of hydrogen, C$_{1-4}$ alkyl, aryl, aryl-C$_{1-4}$alkyl, amino, hydroxy, CO$_2$H, CO$_2$R, CONH$_2$, NR$_2$, CONR$_2$; and
R is a C$_{1-30}$ alkyl,
or a 5,6-dihydrotriazine of formula (I) wherein:
R$^1$ and R$^2$ are independently selected from the group consisting of hydrogen, C$_{1-30}$ alkyl, aryl, C$_{1-30}$ alkylphenyl and aryl-C$_{1-30}$ alkyl wherein each C$_{1-30}$ alkyl optionally contains one or more heteroatoms selected from the group consisting of oxygen, nitrogen and sulphur in the main chain and/or is optionally substituted with one or more hydroxyl groups or R$^1$ and R$^2$ are linked by one or more bonds to form a five, six or seven membered ring comprising P, X$^1$ and X$^2$, said ring being optionally fused with a phenyl ring;
X$^1$ is selected from the group consisting of NR$^4$ and oxygen;
X$^2$ is selected from the group consisting of NR$^5$ and oxygen;
R$^4$ and R$^5$ are independently selected from the group consisting of hydrogen and C$_{1-30}$ alkyl, wherein each C$_{1-30}$ alkyl optionally contains one or more heteroatoms selected from the group consisting of oxygen, nitrogen and sulphur in the main chain and/or is optionally substituted with one or more hydroxyl groups;
Y is hydrogen or is a bond linking oxygen to phosphorous to form a six-membered cyclic phosphonic acid ester;
each of m and n is 1 when Y is hydrogen, or one of m and n is 1 and the other one of m and n is 0 when Y is a bond linking oxygen to phosphorous to form a 6-membered cyclic phosphonic acid ester;
R$^3$ is selected from the group consisting of hydrogen, C$_{1-4}$ alkyl, aryl, aryl-C$_{1-4}$alkyl, amino, hydroxy, and NR$_2$; and
R is a C$_{1-30}$ alkyl.

2. A azacytosine compound according to claim 1, wherein R$^1$ and R$^2$ are independently selected from the group consisting of hydrogen and C$_{1-30}$ alkyl, said C$_{1-30}$ alkyl optionally containing one or more oxygen atoms in the main chain or R$^1$ and R$^2$ are linked by one or more bonds to form a six membered ring comprising P, X$_1$ and X$_2$, said ring being optionally fused with a phenyl ring, and R$^4$ and R$^5$ are independently selected from the group consisting of hydrogen and C$_{1-30}$ alkyl.

3. An azacytosine compound selected from the group consisting of:
Bis(hexadecyloxyethyl)ester of (S)-1-[3-hydroxy-2-(phosphonomethoxy)propyl]-5-azacytosine,
Bis(octadecyl)ester of (S)-1-[3-hydroxy-2-(phosphonomethoxy)propyl]-5-azacytosine,
Bis(pivaloyloxymethyl)ester of (S)-1-[3-hydroxy-2-(phosphonomethoxy)propyl]-5-azacytosine,
Mono(hexadecyloxyethyl)ester of (S)-1-[3-hydroxy-2-(phosphonomethoxy)propyl]-5-azacytosine,
Mono(octadecyl)ester of (S)-1-[3-hydroxy-2-(phosphonomethoxy)propyl]-5-azacytosine, Mono(pivaloyloxymethyl)ester of (S)-1-[3-hydroxy-2-(phosphonomethoxy)propyl]-5-azacytosine, Hexadecyloxyethyl ester of 1-{[(5S)-2-hydroxy-2-oxido-1,4,2-dioxaphosphinan-5-yl]methyl}-5-azacytosine, Octadecyl ester of 1-{[(5S)-2-hydroxy-2-oxido-1,4,2-dioxaphosphinan-5-yl]methyl}-5-azacytosine, and Pivaloyloxymethyl ester of 1-{[(5S)-2-hydroxy-2-oxido-1,4,2-dioxaphosphinan-5-yl]methyl}-5-azacytosine, (S)-1-[3-hydroxy-2-phosphonomethoxypropyl)-5-azacytosine, and stereochemically isomeric forms, salts, and 5,6-dihydrotriazines thereof.

4. An azacytosine compound according to claim 1, having the structural formula (IV), a stereochemically isomeric form, or a salt thereof:

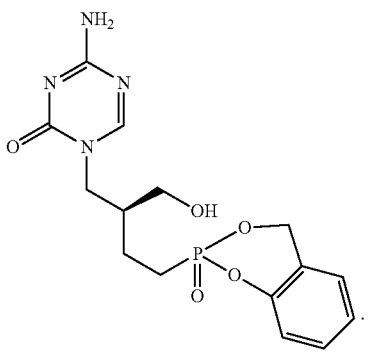

(IV)

5. A method of treating a DNA viral infection or a cell proliferative disorder induced by a DNA viral infection in a mammal by administering a compound according to claim 1 to said mammal in need for such treatment, wherein the viral infection is caused by a virus selected from the group consisting of Herpes simplex virus, Cytomegalovirus, Varicella-Zoster virus, Variola virus and Human Papilloma virus.

6. A pharmaceutical composition comprising a compound according to claim 1 in admixture with at least a pharmaceutically acceptable carrier.

7. An azacytosine compound according to the structural formula (I) of claim 1, wherein Y is a bond linking oxygen to phosphorous to form a 6-membered cyclic phosphonic acid ester, m is 1 and n is 0, being represented by the structural formula:

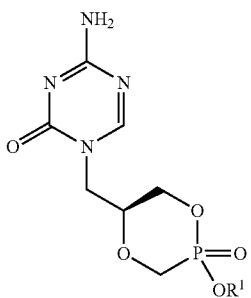

wherein $R^1$ is selected from the group consisting of hydrogen, $C_{1-30}$ alkyl, $C_{2-30}$ alkenyl and $C_{2-30}$ alkynyl, wherein each of said $C_{1-30}$ alkyl, $C_{2-30}$ alkenyl or $C_{2-30}$ alkynyl optionally contains one or more heteroatoms selected from the group consisting of oxygen, nitrogen and sulphur in the main chain and/or is optionally substituted with one or more substituents selected from the group consisting of hydroxy and halogen.

8. A pharmaceutical composition comprising a compound according to claim 1 in admixture with at least a pharmaceutically acceptable carrier, wherein said compound is represented by the structural formula:

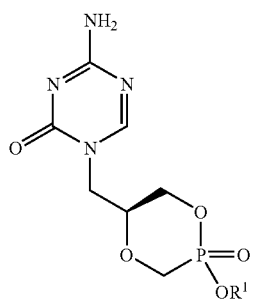

wherein $R^1$ is selected from the group consisting of hydrogen, $C_{1-30}$ alkyl, $C_{2-30}$ alkenyl and $C_{2-30}$ alkynyl, wherein each of said $C_{1-30}$ alkyl, $C_{2-30}$ alkenyl or $C_{2-30}$ alkynyl optionally contains one or more heteroatoms selected from the group consisting of oxygen, nitrogen and sulphur in the main chain and/or is optionally substituted with one or more substituents selected from the group consisting of hydroxy and halogen.

9. A ring-opening reaction product of an azacytosine compound according to claim 1 reacted with a trialkylammonium buffer.

10. The product according to claim 9, being 3-formyl-2-{[(2S)-3-hydroxy-2-(phosphonomethoxy)propyl]-carbamoyl}guanidine.

11. A pharmaceutical composition comprising the product of claim 9, in admixture with at least a pharmaceutically acceptable carrier.

12. A pharmaceutical composition comprising the product according to claim 10, in admixture with at least a pharmaceutically acceptable carrier.

13. A method of treating a DNA viral infection or a cell proliferative disorder induced by a DNA viral infection in a mammal by administering a product of claim 9 to said mammal in need for such prevention or treatment, wherein the viral infection is caused by a virus selected from the group consisting of Herpes simplex virus, Cytomegalovirus, Varicella-Zoster virus, Variola virus and Human Papilloma virus.

* * * * *